(12) United States Patent
Whitfield et al.

(10) Patent No.: US 8,357,171 B2
(45) Date of Patent: *Jan. 22, 2013

(54) ENDOSCOPIC SURGICAL CLIP APPLIER

(75) Inventors: Kenneth H. Whitfield, New Haven, CT (US); Gregory Sorrentino, Wallingford, CT (US)

(73) Assignee: Covidien LP, Mansfield, MA (US)

(*) Notice: Subject to any disclaimer, the term of this patent is extended or adjusted under 35 U.S.C. 154(b) by 300 days.

This patent is subject to a terminal disclaimer.

(21) Appl. No.: 12/764,226

(22) Filed: Apr. 21, 2010

(65) Prior Publication Data

US 2010/0204715 A1 Aug. 12, 2010

Related U.S. Application Data

(62) Division of application No. 11/245,493, filed on Oct. 7, 2005, now Pat. No. 7,717,926.

(60) Provisional application No. 60/617,104, filed on Oct. 8, 2004, provisional application No. 60/617,016, filed on Oct. 8, 2004.

(51) Int. Cl.
*A61B 17/10* (2006.01)

(52) U.S. Cl. ...................................... 606/143

(58) Field of Classification Search .............. 606/142, 606/143, 157, 158, 205–208, 219
See application file for complete search history.

(56) References Cited

U.S. PATENT DOCUMENTS

| 3,120,230 A | 2/1964 | Skold |
| 3,638,847 A | 2/1972 | Noiles et al. |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,480,640 A | 11/1984 | Becht |
| 4,480,641 A | 11/1984 | Failla et al. |

(Continued)

FOREIGN PATENT DOCUMENTS

EP 0 085 931 A2 8/1983

(Continued)

OTHER PUBLICATIONS

Extended European Search Report corresponding to EP 10252079.8, date of mailing is Mar. 17, 2011; date of completion of Search is Mar. 8, 2011 (3 Pages).

(Continued)

*Primary Examiner* — Tuan V Nguyen

(57) ABSTRACT

An apparatus for application of surgical clips to body tissue has a handle portion with a body extending distally from the handle portion defining a longitudinal axis and a plurality of surgical clips disposed within the body. The apparatus also has a jaw assembly mounted adjacent a distal end portion of the body with the jaw assembly including first and second jaw portions movable between a spaced-apart and an approximated position. The apparatus further has a wedge plate longitudinally movable between the first and the second jaw portions, and a clip pusher configured to individually distally advance a surgical clip to the jaw assembly while the jaw portions are in the spaced apart position with an actuator. The actuator is at least partially disposed within the body and longitudinally movable in response to actuation of the handle portion and has a cam link. The apparatus also has a jaw closure member positioned adjacent the first and second jaw portions to move the jaw portions to the approximated position. The cam link longitudinally moves wedge plate between the first and the second jaw portions.

9 Claims, 44 Drawing Sheets

U.S. PATENT DOCUMENTS

| | | |
|---|---|---|
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |

| | | | | | |
|---|---|---|---|---|---|
| 5,501,693 A | 3/1996 | Gravener | 5,846,255 A | 12/1998 | Casey |
| 5,509,920 A | 4/1996 | Phillips et al. | 5,849,019 A | 12/1998 | Yoon |
| 5,514,149 A | 5/1996 | Green et al. | 5,858,018 A | 1/1999 | Shipp et al. |
| 5,520,701 A | 5/1996 | Lerch | 5,861,005 A | 1/1999 | Kontos |
| 5,522,823 A | 6/1996 | Kuntz et al. | 5,861,018 A | 1/1999 | Feierbach |
| 5,527,318 A | 6/1996 | McGarry | 5,868,759 A | 2/1999 | Peyser et al. |
| 5,527,319 A | 6/1996 | Green et al. | 5,868,761 A | 2/1999 | Nicholas et al. |
| 5,527,320 A | 6/1996 | Carruthers et al. | 5,876,410 A | 3/1999 | Petillo |
| 5,542,949 A | 8/1996 | Yoon | 5,895,394 A | 4/1999 | Kienzle et al. |
| 5,547,474 A | 8/1996 | Kloeckl et al. | 5,897,565 A | 4/1999 | Foster |
| 5,569,274 A | 10/1996 | Rapacki et al. | 5,904,693 A | 5/1999 | Dicesare et al. |
| 5,571,121 A | 11/1996 | Heifetz | 5,913,862 A | 6/1999 | Ramsey et al. |
| 5,575,802 A | 11/1996 | McQuilkin et al. | 5,918,791 A | 7/1999 | Sorrentino et al. |
| 5,582,615 A | 12/1996 | Foshee et al. | 5,921,996 A | 7/1999 | Sherman |
| 5,584,840 A | 12/1996 | Ramsey et al. | 5,921,997 A | 7/1999 | Fogelberg et al. |
| 5,591,178 A | 1/1997 | Green et al. | 5,928,251 A | 7/1999 | Aranyi et al. |
| 5,593,414 A | 1/1997 | Shipp et al. | 5,938,667 A | 8/1999 | Peyser et al. |
| 5,593,421 A | 1/1997 | Bauer | 5,951,574 A | 9/1999 | Stefanchik et al. |
| 5,601,573 A | 2/1997 | Fogelberg et al. | 5,972,003 A | 10/1999 | Rousseau et al. |
| 5,601,574 A | 2/1997 | Stefanchik et al. | 5,976,159 A | 11/1999 | Bolduc et al. |
| 5,607,436 A | 3/1997 | Pratt et al. | 5,993,465 A | 11/1999 | Shipp et al. |
| 5,618,291 A | 4/1997 | Thompson et al. | 6,004,335 A | 12/1999 | Vaitekunas et al. |
| 5,618,306 A | 4/1997 | Roth et al. | 6,017,358 A | 1/2000 | Yoon et al. |
| 5,620,452 A | 4/1997 | Yoon | RE36,720 E | 5/2000 | Green et al. |
| 5,626,585 A | 5/1997 | Mittelstadt et al. | 6,059,799 A | 5/2000 | Aranyi et al. |
| 5,626,586 A | 5/1997 | Pistl et al. | 6,099,536 A | 8/2000 | Petillo |
| 5,626,592 A | 5/1997 | Phillips et al. | 6,099,537 A | 8/2000 | Sugai et al. |
| RE35,525 E | 6/1997 | Stefanchik et al. | 6,139,555 A | 10/2000 | Hart et al. |
| 5,634,930 A | 6/1997 | Thornton et al. | 6,210,418 B1 | 4/2001 | Storz et al. |
| 5,643,291 A | 7/1997 | Pier et al. | 6,217,590 B1 | 4/2001 | Levinson |
| 5,645,551 A | 7/1997 | Green et al. | 6,228,097 B1 | 5/2001 | Levinson et al. |
| 5,645,553 A | 7/1997 | Kolesa et al. | 6,241,740 B1 | 6/2001 | Davis et al. |
| 5,649,937 A | 7/1997 | Bito et al. | 6,258,105 B1 | 7/2001 | Hart et al. |
| 5,653,720 A | 8/1997 | Johnson et al. | 6,261,302 B1 | 7/2001 | Voegele et al. |
| 5,662,676 A | 9/1997 | Koninckx | 6,273,898 B1 | 8/2001 | Kienzle et al. |
| 5,662,679 A | 9/1997 | Voss et al. | 6,277,131 B1 | 8/2001 | Kalikow |
| 5,665,097 A | 9/1997 | Baker et al. | 6,306,149 B1 | 10/2001 | Meade |
| 5,676,676 A | 10/1997 | Porter | 6,318,619 B1 | 11/2001 | Lee |
| 5,681,330 A | 10/1997 | Hughett et al. | 6,322,571 B1 | 11/2001 | Adams |
| 5,683,405 A | 11/1997 | Yacoubian et al. | 6,350,269 B1 | 2/2002 | Shipp et al. |
| 5,695,502 A | 12/1997 | Pier et al. | 6,352,541 B1 | 3/2002 | Kienzle et al. |
| 5,695,505 A | 12/1997 | Yoon | 6,391,035 B1 | 5/2002 | Appleby et al. |
| 5,697,938 A | 12/1997 | Jensen et al. | 6,423,079 B1 | 7/2002 | Blake, III |
| 5,700,270 A | 12/1997 | Peyser et al. | 6,428,548 B1 | 8/2002 | Durgin et al. |
| 5,700,271 A | 12/1997 | Whitfield et al. | 6,440,144 B1 | 8/2002 | Bacher |
| 5,702,048 A | 12/1997 | Eberlin | 6,461,363 B1 | 10/2002 | Gadberry et al. |
| 5,709,706 A | 1/1998 | Kienzle et al. | 6,464,710 B1 | 10/2002 | Foster |
| 5,713,911 A | 2/1998 | Racenet et al. | 6,494,886 B1 | 12/2002 | Wilk et al. |
| 5,713,912 A | 2/1998 | Porter | 6,517,536 B2 | 2/2003 | Hooven et al. |
| 5,720,756 A | 2/1998 | Green et al. | 6,520,972 B2 | 2/2003 | Peters |
| 5,722,982 A | 3/1998 | Ferreira et al. | 6,527,786 B1 | 3/2003 | Davis et al. |
| 5,725,537 A | 3/1998 | Green et al. | 6,537,289 B1 | 3/2003 | Kayan et al. |
| 5,725,538 A | 3/1998 | Green et al. | 6,546,935 B2 | 4/2003 | Hooven |
| 5,725,542 A | 3/1998 | Yoon | 6,551,333 B2 | 4/2003 | Kuhns et al. |
| 5,733,295 A | 3/1998 | Back et al. | 6,569,171 B2 | 5/2003 | DeGuillebon et al. |
| 5,755,726 A | 5/1998 | Pratt et al. | 6,579,304 B1 | 6/2003 | Hart et al. |
| 5,766,189 A | 6/1998 | Matsuno | 6,599,298 B1 | 7/2003 | Forster et al. |
| 5,769,857 A | 6/1998 | Reztzov et al. | 6,602,252 B2 | 8/2003 | Mollenauer |
| 5,772,673 A | 6/1998 | Cuny et al. | 6,607,540 B1 | 8/2003 | Shipp |
| 5,776,146 A | 7/1998 | Sackier et al. | 6,613,060 B2 | 9/2003 | Adams et al. |
| 5,776,147 A | 7/1998 | Dolendo | 6,626,916 B1 | 9/2003 | Yeung et al. |
| 5,779,718 A | 7/1998 | Green et al. | 6,626,922 B1 | 9/2003 | Hart et al. |
| 5,779,720 A | 7/1998 | Walder-Utz et al. | 6,648,898 B1 | 11/2003 | Baxter |
| 5,782,844 A | 7/1998 | Yoon et al. | 6,652,538 B2 | 11/2003 | Kayan et al. |
| 5,788,698 A | 8/1998 | Savornin | 6,652,539 B2 | 11/2003 | Shipp et al. |
| 5,792,149 A | 8/1998 | Sherts et al. | 6,673,083 B1 | 1/2004 | Kayan et al. |
| 5,792,150 A | 8/1998 | Pratt et al. | 6,676,659 B2 | 1/2004 | Hutchins et al. |
| 5,797,922 A | 8/1998 | Hessel et al. | 6,679,894 B2 | 1/2004 | Damarati |
| 5,810,853 A | 9/1998 | Yoon | RE38,445 E | 2/2004 | Pistl et al. |
| 5,817,116 A | 10/1998 | Takahashi et al. | 6,695,854 B1 | 2/2004 | Kayan et al. |
| 5,824,547 A | 10/1998 | Hashino et al. | 6,706,057 B1 | 3/2004 | Bidoia et al. |
| 5,824,548 A | 10/1998 | Hearn | 6,716,226 B2 | 4/2004 | Sixto, Jr. et al. |
| 5,827,306 A | 10/1998 | Yoon | 6,723,109 B2 | 4/2004 | Solingen |
| 5,833,695 A | 11/1998 | Yoon | 6,743,240 B2 | 6/2004 | Smith et al. |
| 5,833,696 A | 11/1998 | Whitfield et al. | 6,773,438 B1 | 8/2004 | Knodel et al. |
| 5,833,700 A | 11/1998 | Fogelberg et al. | 6,773,440 B2 | 8/2004 | Gannoe et al. |
| 5,835,199 A | 11/1998 | Phillips et al. | 6,776,783 B1 | 8/2004 | Frantzen et al. |
| 5,843,097 A | 12/1998 | Mayenberger et al. | 6,776,784 B2 | 8/2004 | Ginn |
| 5,843,101 A | 12/1998 | Fry | 6,780,195 B2 | 8/2004 | Porat |

| | | |
|---|---|---|
| 6,793,663 B2 | 9/2004 | Kneifel et al. |
| 6,793,664 B2 | 9/2004 | Mazzocchi et al. |
| 6,793,666 B2 | 9/2004 | Hansen et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,966,981 B2 | 11/2005 | Binder et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,597 B2 | 1/2006 | Gellman et al. |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,320,692 B1 | 1/2008 | Bender et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,344,544 B2 | 3/2008 | Bender et al. |
| 7,357,805 B2 | 4/2008 | Masuda et al. |
| 7,357,806 B2 | 4/2008 | Rivera et al. |
| 7,407,074 B2 | 8/2008 | Ortiz et al. |
| 7,419,495 B2 | 9/2008 | Menn et al. |
| 7,431,724 B2 | 10/2008 | Manetakis et al. |
| 7,458,978 B1 | 12/2008 | Bender et al. |
| 7,473,258 B2 | 1/2009 | Clauson et al. |
| 7,485,124 B2 | 2/2009 | Kuhns et al. |
| 7,717,926 B2 * | 5/2010 | Whitfield et al. ............ 606/143 |
| 7,819,886 B2 * | 10/2010 | Whitfield et al. ............ 606/143 |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |

| Publication No. | Date | Inventor |
|---|---|---|
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santili et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes Jr et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045978 A1 | 2/2008 | Kuhns et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0114377 A1 | 5/2008 | Shibata et al. |
| 2008/0114378 A1 | 5/2008 | Matsushita |
| 2008/0125796 A1 | 5/2008 | Graham |
| 2008/0132915 A1 | 6/2008 | Buckman et al. |
| 2008/0140089 A1 | 6/2008 | Kogiso et al. |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0188872 A1 | 8/2008 | Duff |
| 2008/0207995 A1 | 8/2008 | Kortenbach et al. |
| 2008/0208217 A1 | 8/2008 | Adams |
| 2008/0228199 A1 | 9/2008 | Cropper et al. |
| 2008/0228202 A1 | 9/2008 | Cropper et al. |
| 2008/0243143 A1 | 10/2008 | Kuhns et al. |
| 2008/0243145 A1 | 10/2008 | Whitfield et al. |
| 2008/0255589 A1 | 10/2008 | Blakeney et al. |
| 2008/0294178 A1 | 11/2008 | Kortenbach et al. |
| 2008/0306491 A1 | 12/2008 | Cohen et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312666 A1 | 12/2008 | Ellingwood et al. |
| 2008/0312670 A1 | 12/2008 | Lutze et al. |
| 2008/0319456 A1 | 12/2008 | Hart |

FOREIGN PATENT DOCUMENTS

| | | |
|---|---|---|
| EP | 0 324 166 A2 | 7/1989 |
| EP | 0 392 750 A1 | 10/1990 |
| EP | 0 598 529 A2 | 5/1994 |
| EP | 0 769 275 A1 | 5/1994 |
| EP | 0 685 204 A1 | 12/1995 |
| EP | 0 732 078 | 9/1996 |
| EP | 0 755 655 | 1/1997 |
| EP | 0 769 275 | 4/1997 |
| EP | 0769274 A1 | 4/1997 |
| EP | 0 834 286 | 4/1998 |
| EP | 1 317 906 | 6/2003 |
| EP | 1 609 427 | 12/2005 |
| EP | 1 712 191 | 10/2006 |
| EP | 1 813 199 A1 | 8/2007 |
| EP | 1 908 423 | 4/2008 |
| EP | 1 908 423 A2 | 4/2008 |
| EP | 1 913 881 | 4/2008 |
| EP | 2 229 895 A1 | 9/2010 |
| JP | 2003 033361 A | 2/2003 |
| WO | WO 2005/091457 | 9/2005 |
| WO | WO 2006/042076 | 4/2006 |
| WO | WO 2006/042084 | 4/2006 |
| WO | WO 2006/042110 | 4/2006 |
| WO | WO 2008/118928 | 10/2008 |
| WO | WO 2008/127968 | 10/2008 |

OTHER PUBLICATIONS

The extended European Search Report corresponding to European Application No. EP 11250214.1, completed May 25, 2011; mailed Jun. 1, 2011; (3 Pages).

Extended European Search Report corresponding to EP 09252056.8. date of mailing is Feb. 5, 2010; date of completion of Search is Jan. 8, 2010 (3 Pages).

Extended European Search Report corresponding to EP 10250497.4, date of mailing is May 12, 2010; date of completion of Search is May 4, 2010 (6 Pages).

European Search Report corresponding to EP 05810218.7, mailed on May 20, 2011; completed on Apr. 18, 2011; 3 pages.

Extended European Search Report corresponding to EP 10251737.2, mailed on May 20, 2011; completed on May 9, 2011; 4 pages.

International Search Report corresponding to EP 07 25 3905; date of mailing is Feb. 7, 2008; date of completion of Search is Jan. 29, 2008 (7 Pages).

International Search Report corresponding to EP 07 25 3807; date of mailing is Aug. 1, 2008; date of completion of Search is Jul. 23, 2008 (3 Pages).

International Search Report corresponding to PCT/US08/58185; date of mailing is Sep. 9, 2008; date of completion of Search is Sep. 4, 2008 (2 Pages).

International Search Report corresponding to PCT/US08/59859; date of mailing is Sep. 18, 2008; date of completion of Search is Sep. 14, 2008 (2 Pages).

The extended European Search Report corresponding to EP 07 25 3807; date of mailing is Nov. 26, 2008; date of completion of Search is Nov. 7, 2008 (11 Pages).

European Search Report corresponding to EP 09252049; date of mailing is Jan. 12, 2010; date of completion of Search is Dec. 11, 2009 (3 Pages).

European Search Report corresponding to EP 09252050; date of mailing is Jan. 21, 2010; date of completion of Search is Dec. 23, 2009 (3 Pages).

European Search Report corresponding to EP 09252051; date of mailing is Jan. 28, 2010; date of completion of Search is Dec. 21, 2009 (3 Pages).

European Search Report corresponding to EP09252053.5, date of mailing is Dec. 1, 2009; date of completion of Search is Nov. 24, 2009 (3 Pages).

European Search Report corresponding to EP 09252054; date of mailing is Jan. 22, 2010; date of completion of Search is Jan. 7, 2010 (3 Pages).

Extended European Search Report corresponding to EP 09252056.8, date of mailing is Feb. 5, 2010; date of completion of Search is Jan. 8, 2010 (3 Pages).

"Salute II Disposable Fixation Device", Technique Guide—Laparoscopic and Open Inguinal and Ventral Hernia Repair; Davol, A Bard Company, 2006; 7 Pages.

European Search Report corresponding to European Application No. EP 05 80 2686.5, completed Jan. 9, 2012; mailed Jan. 18, 2012; (3 Pages).

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

\* cited by examiner

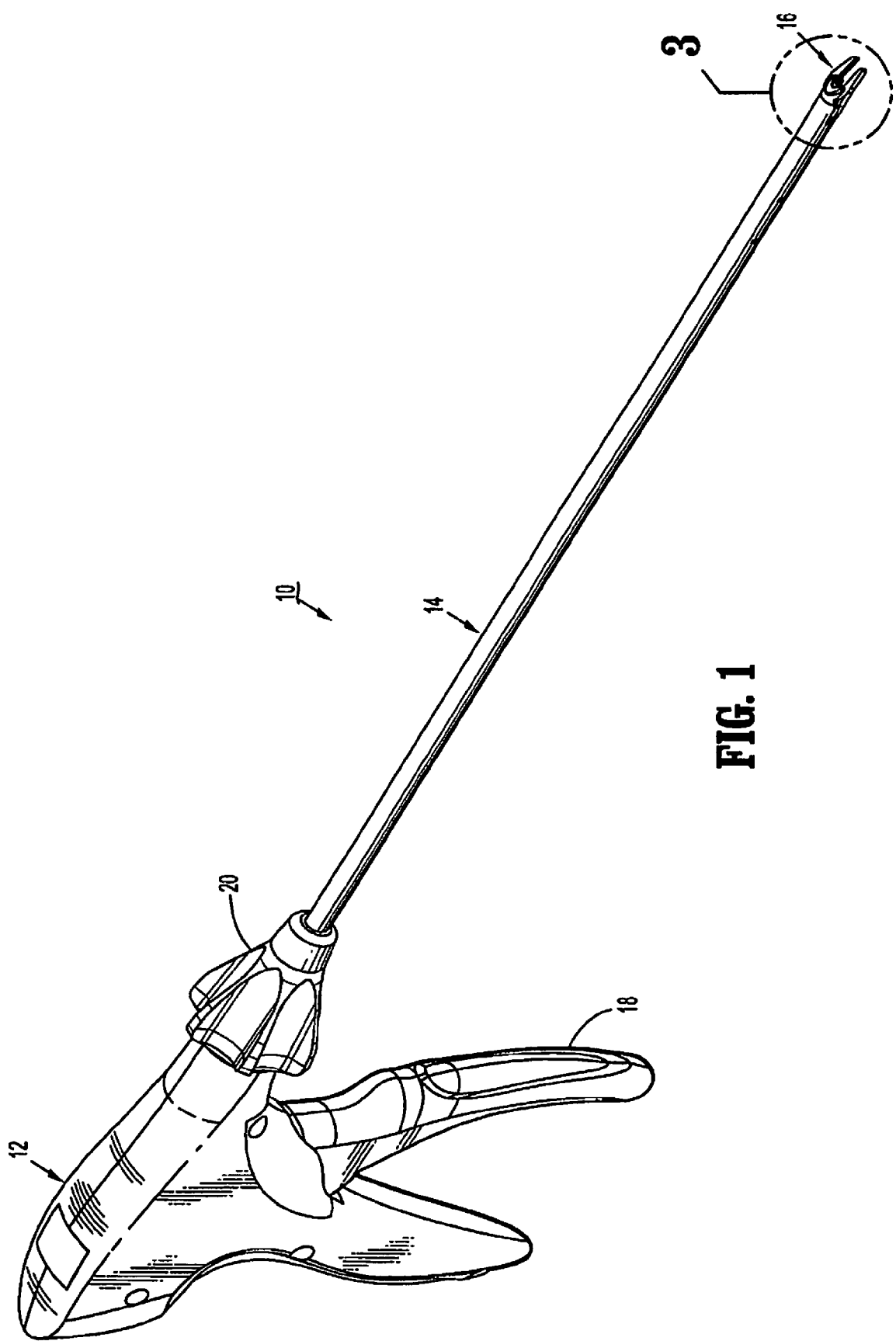

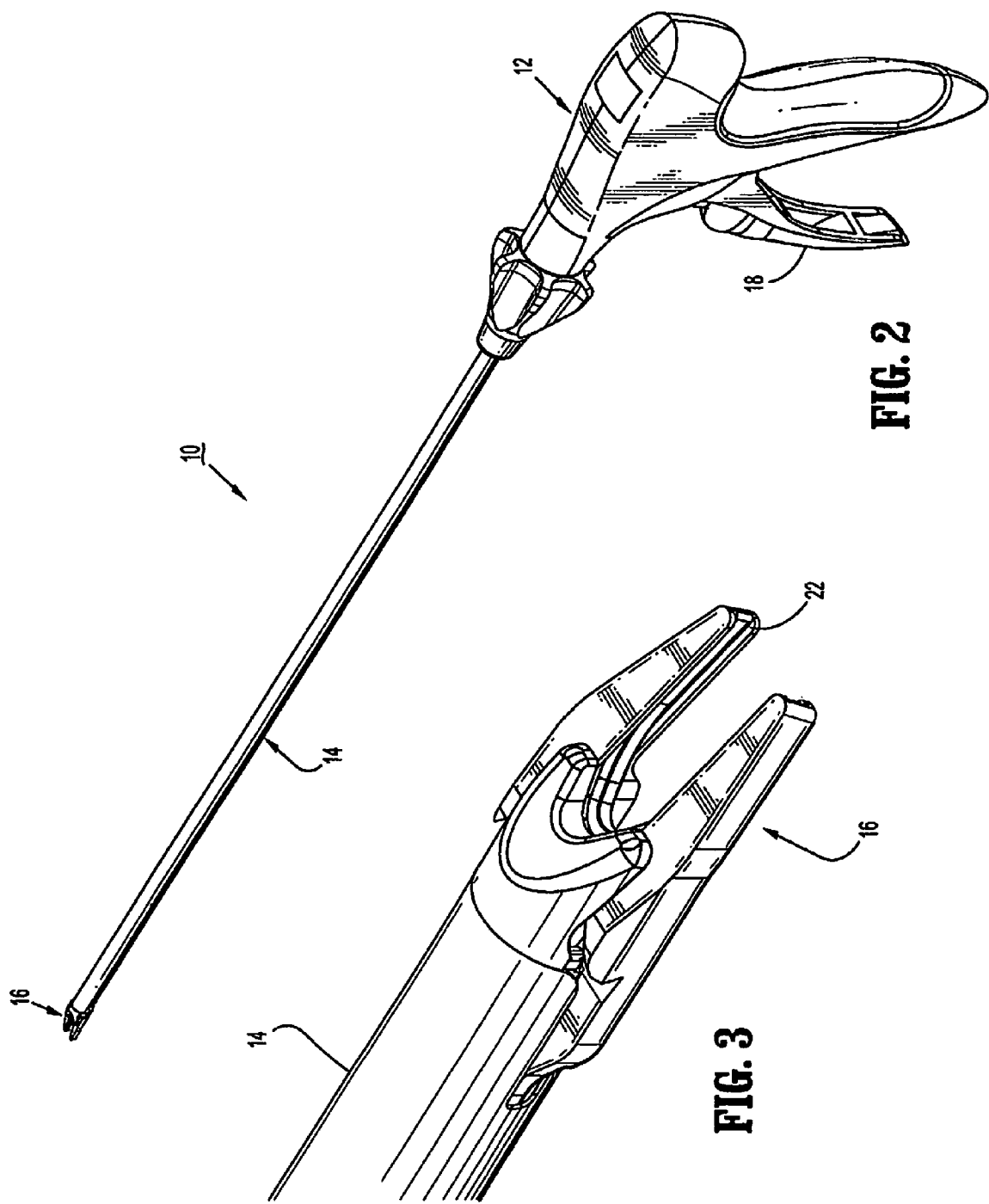

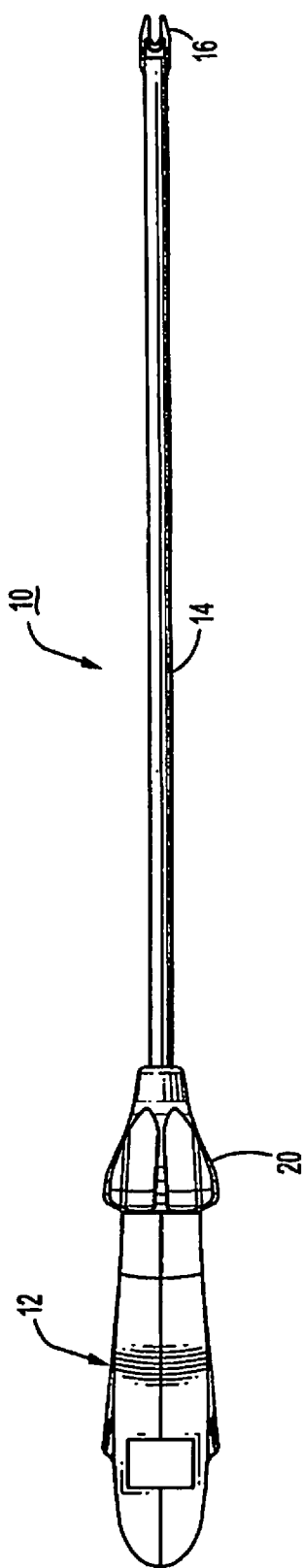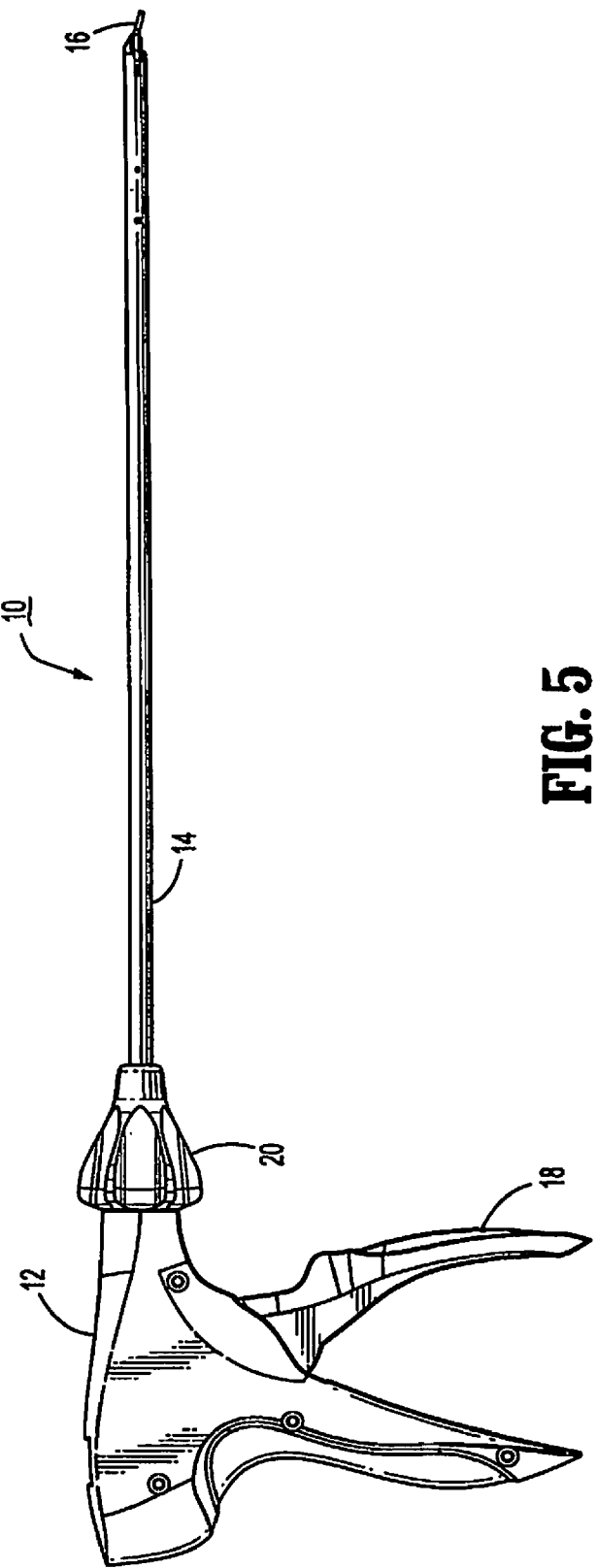

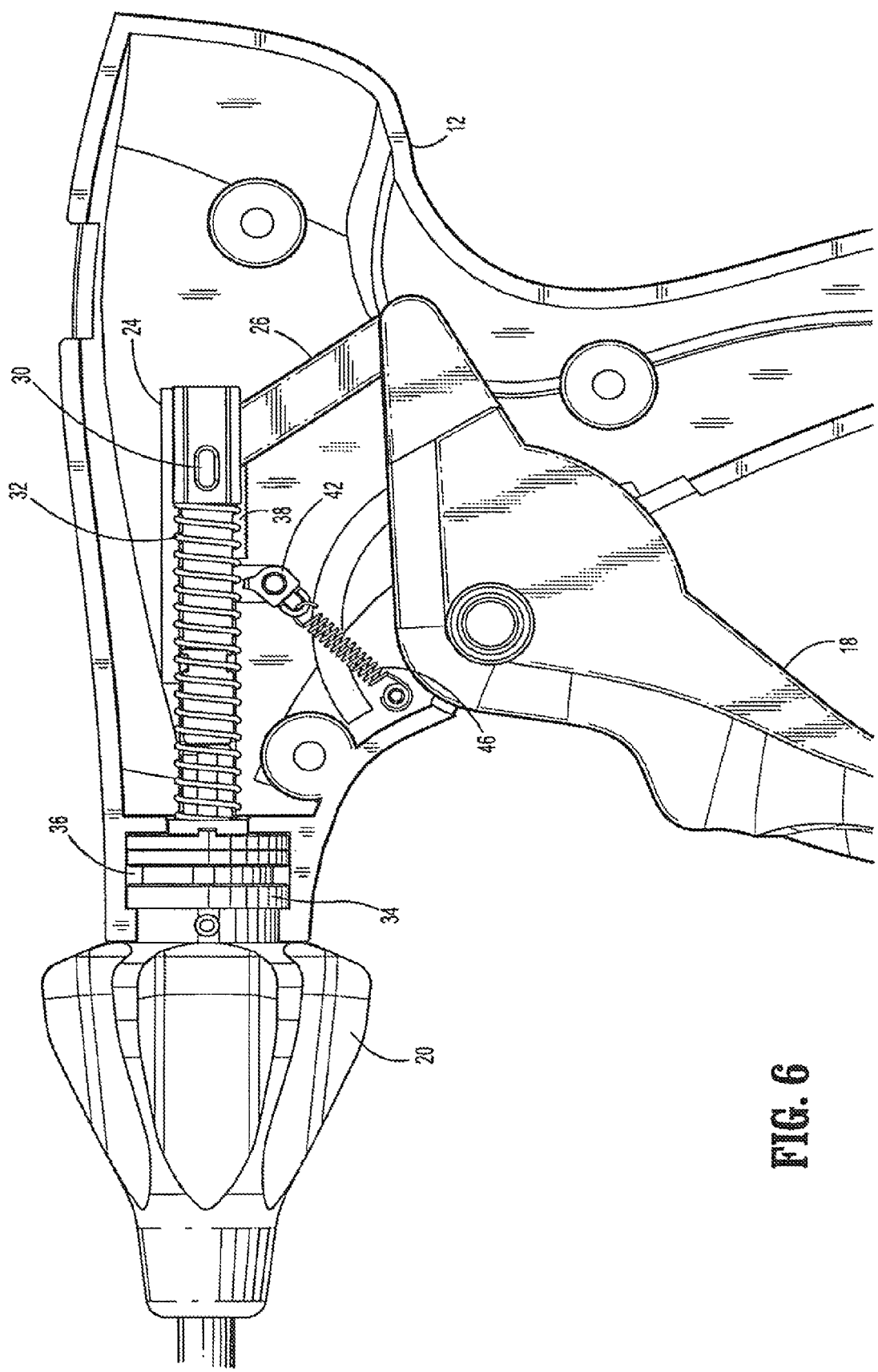

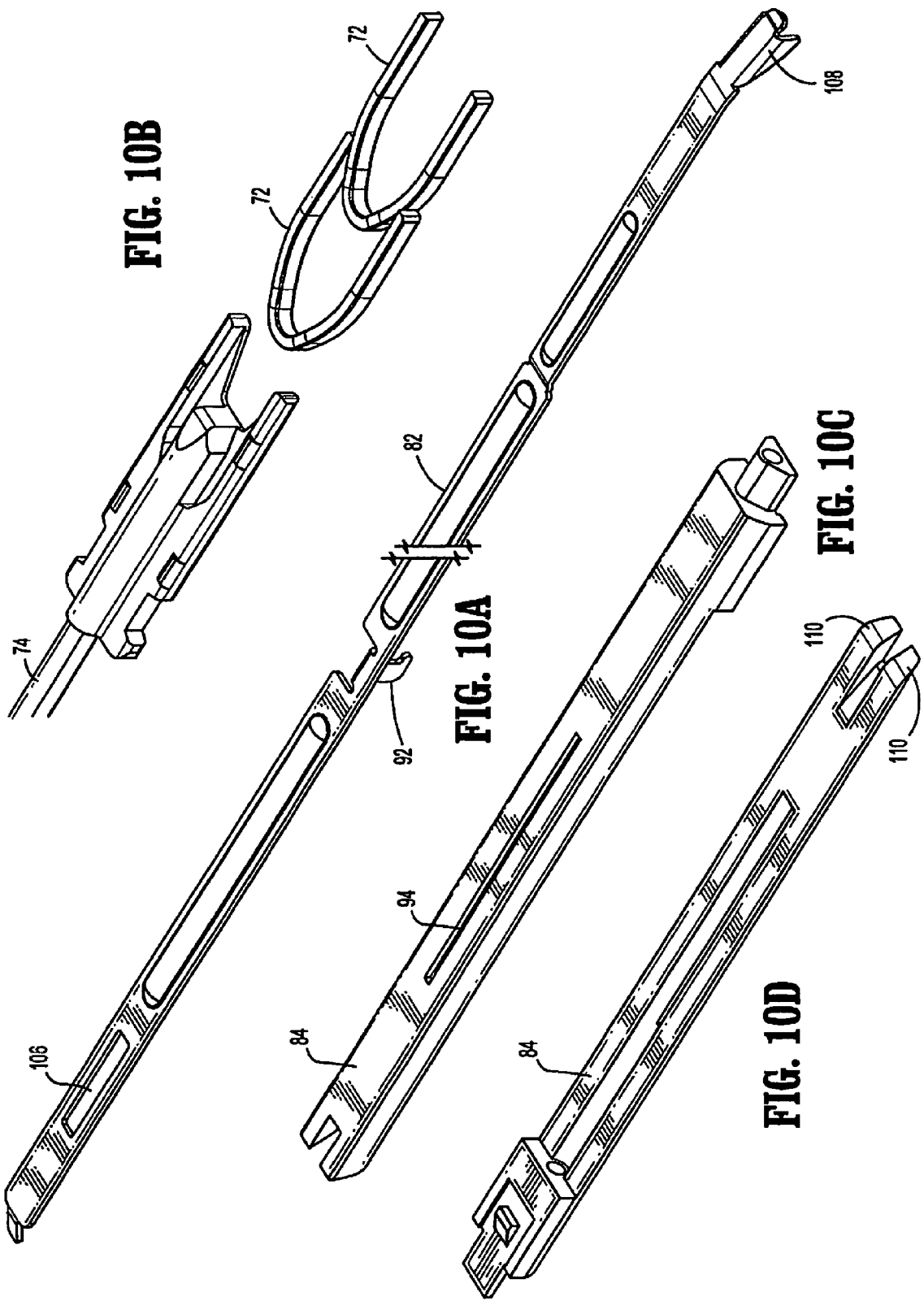

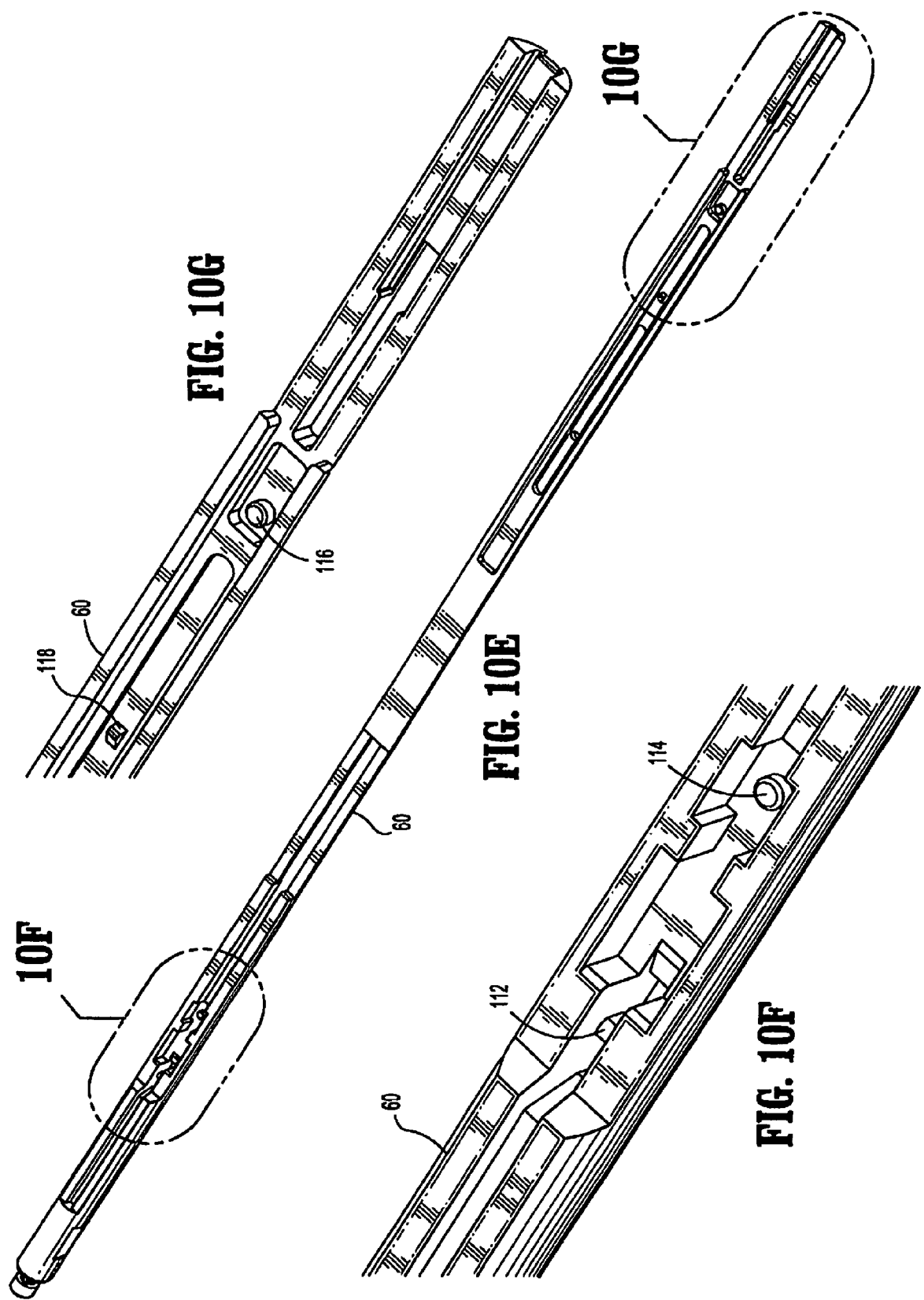

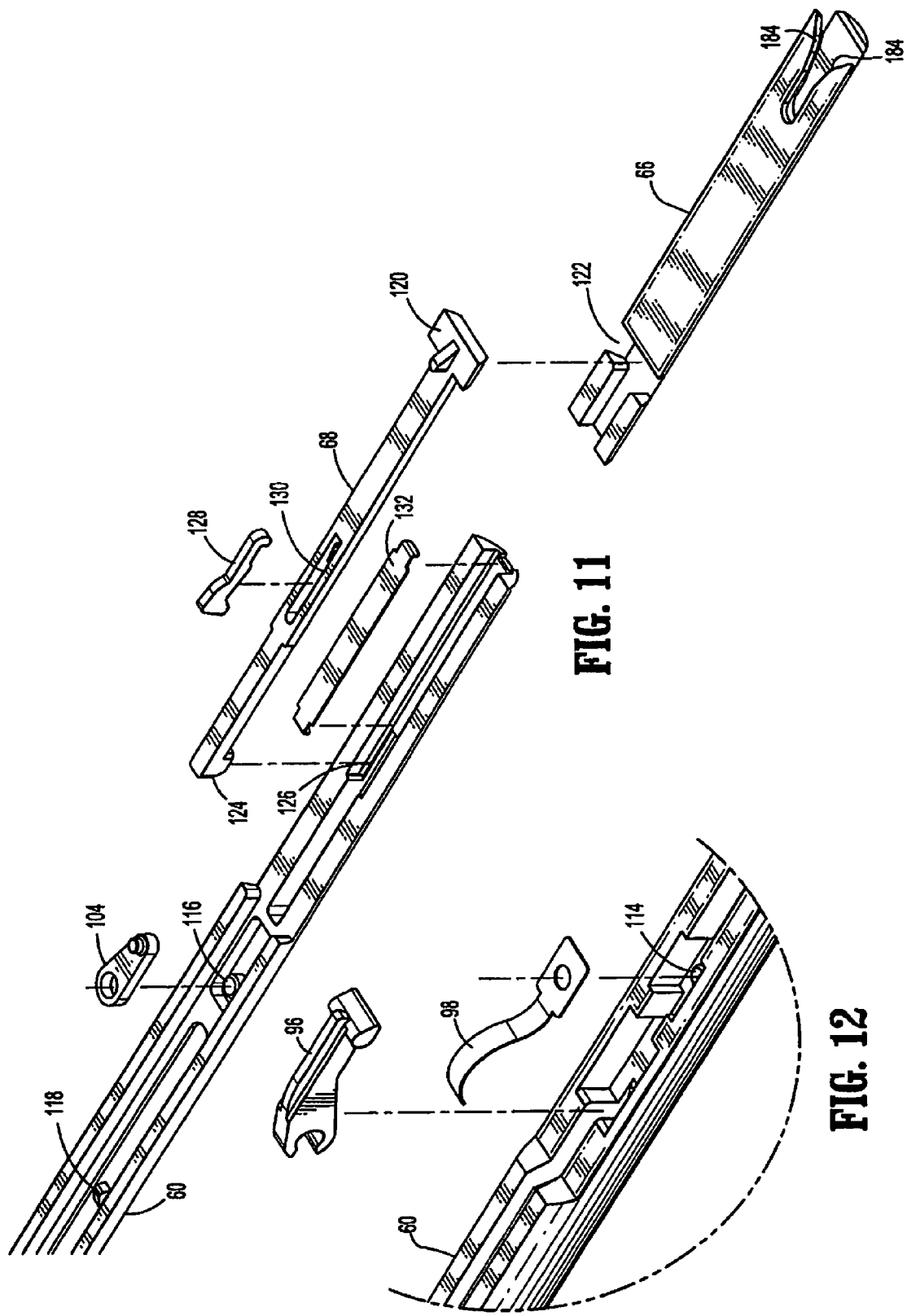

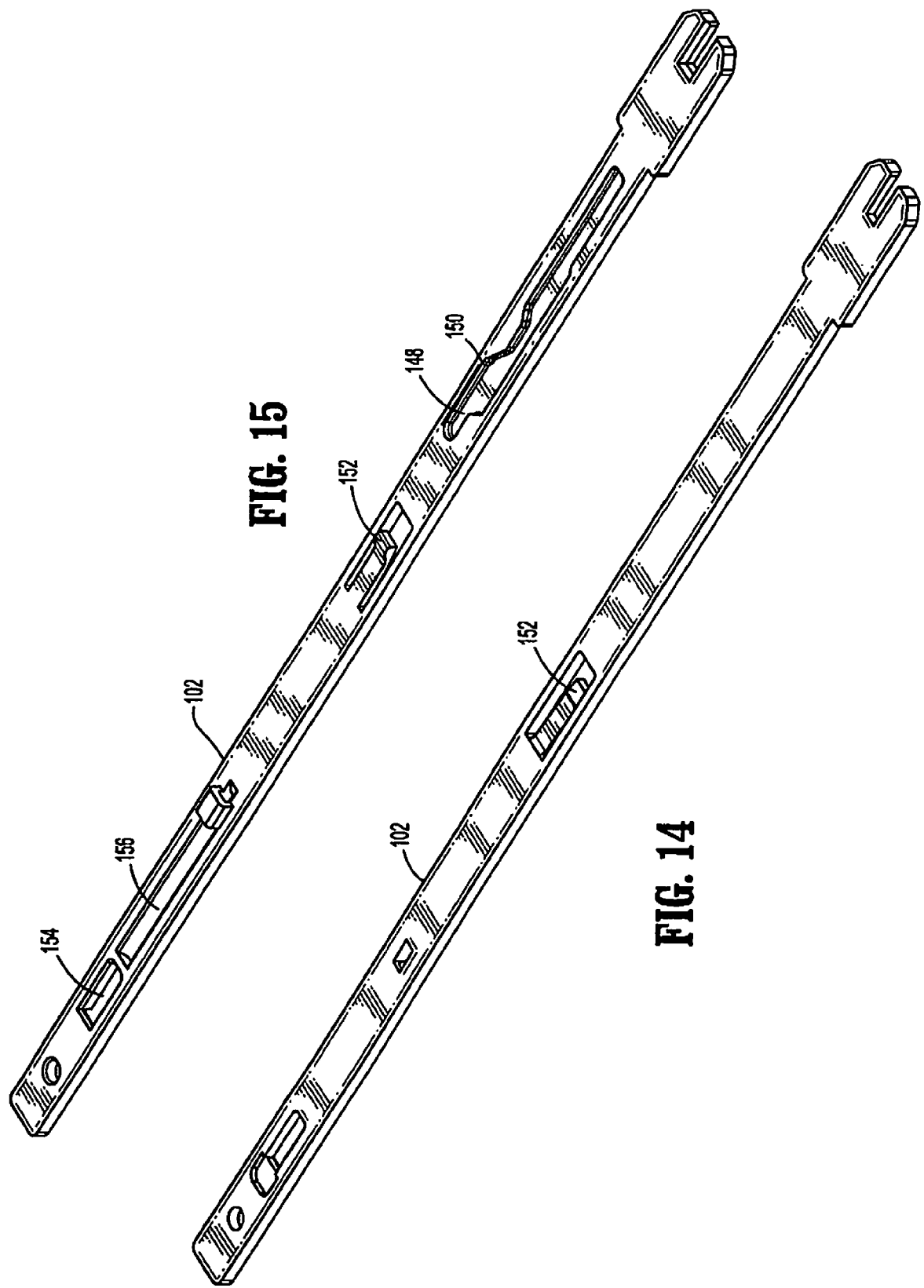

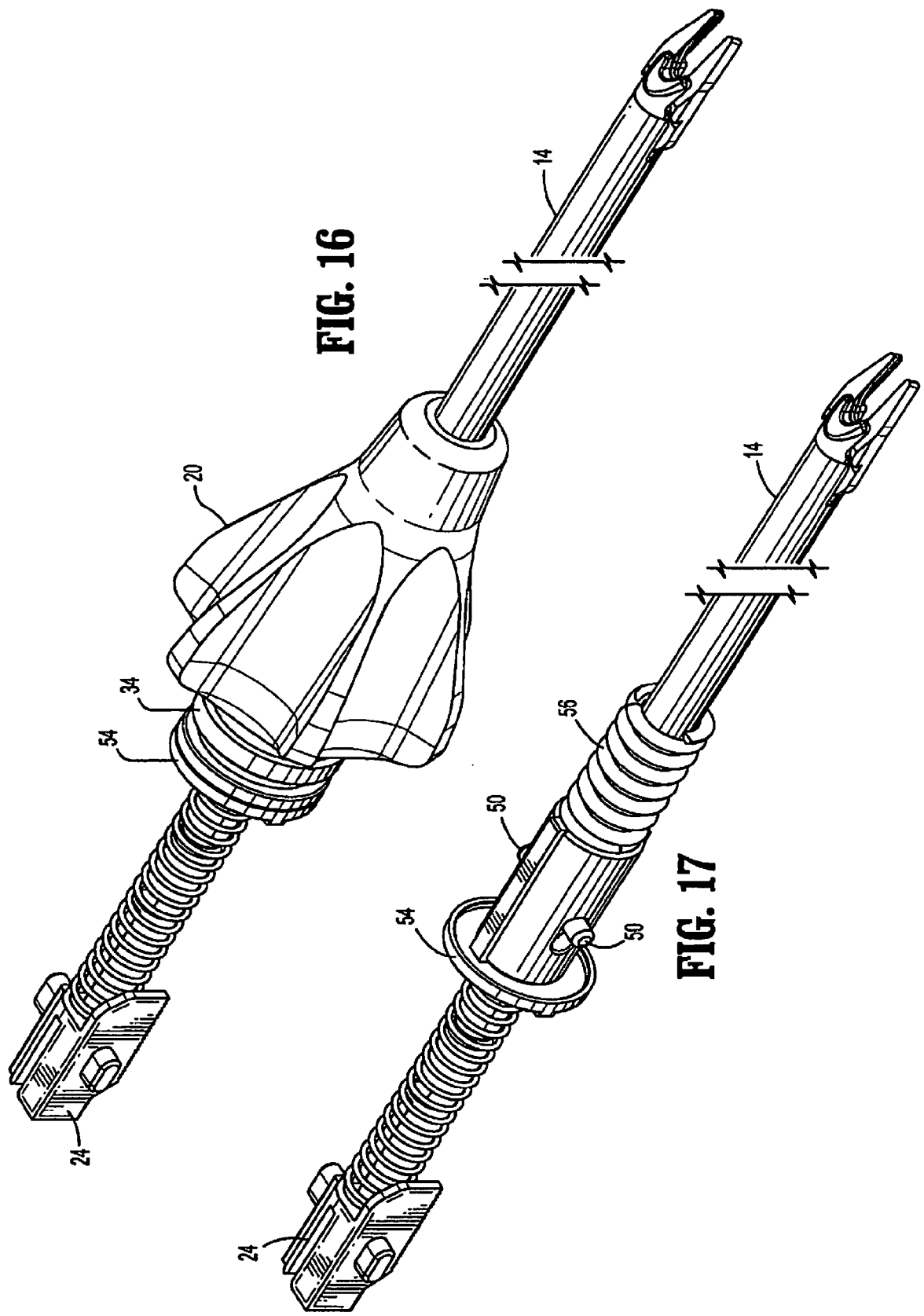

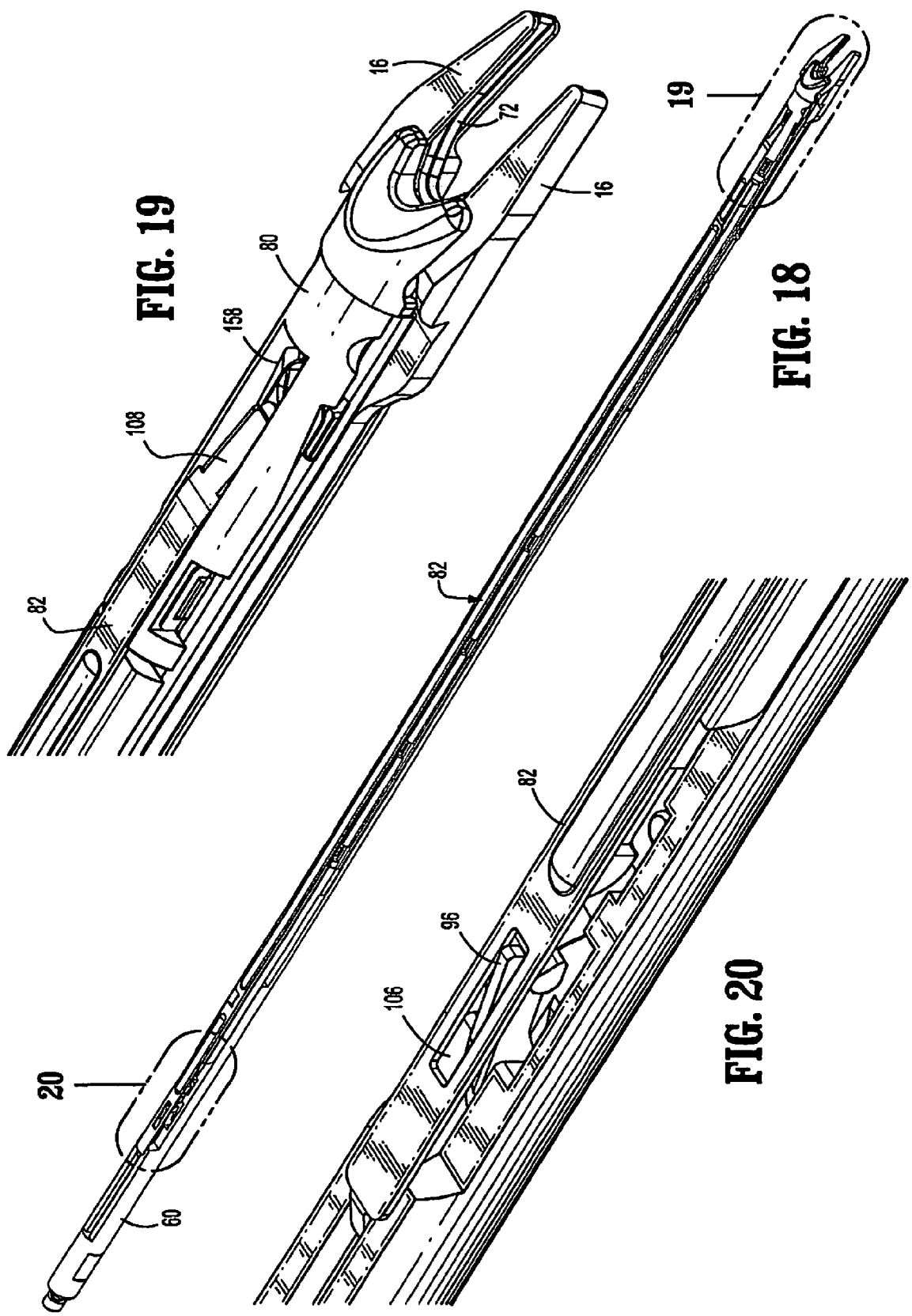

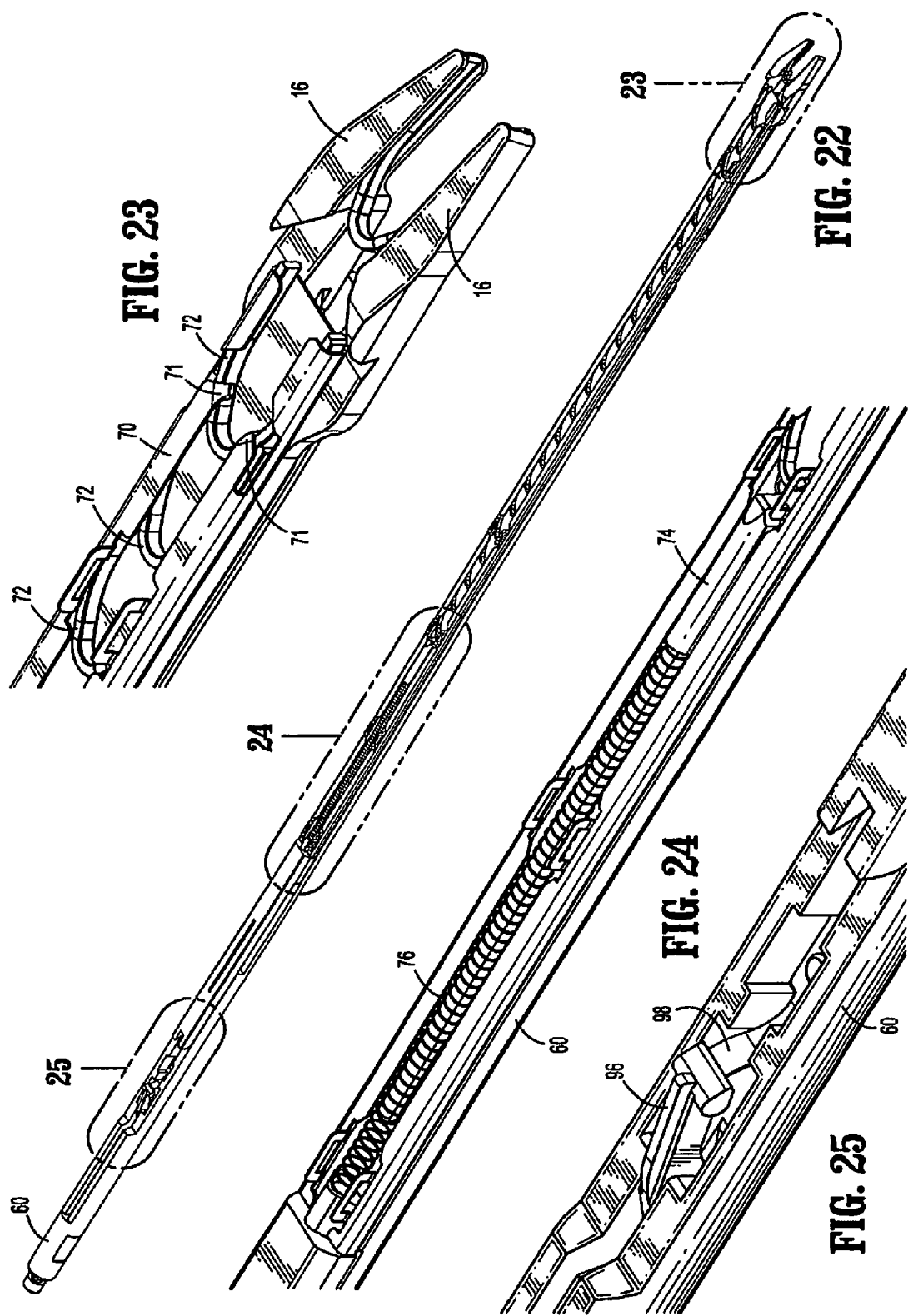

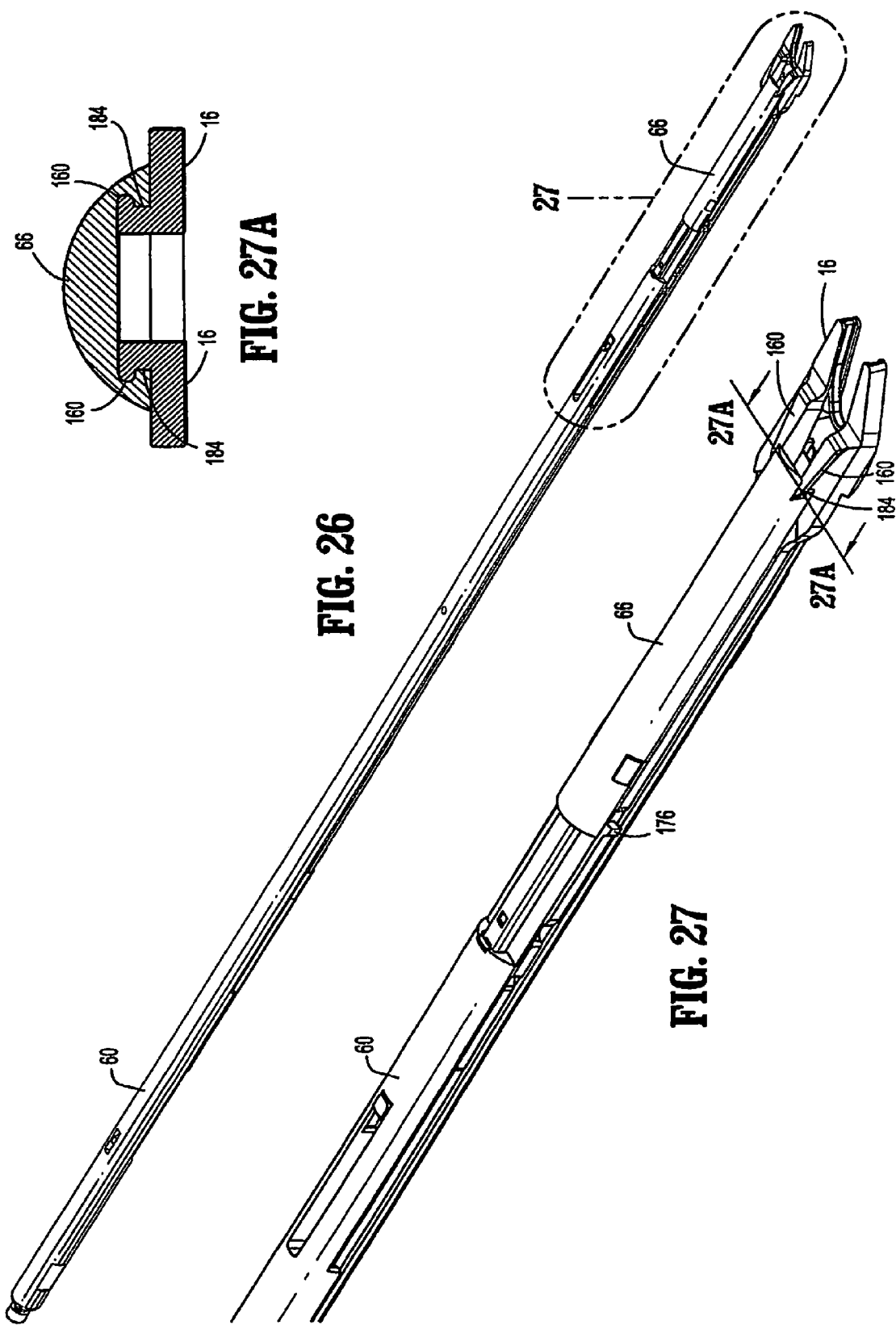

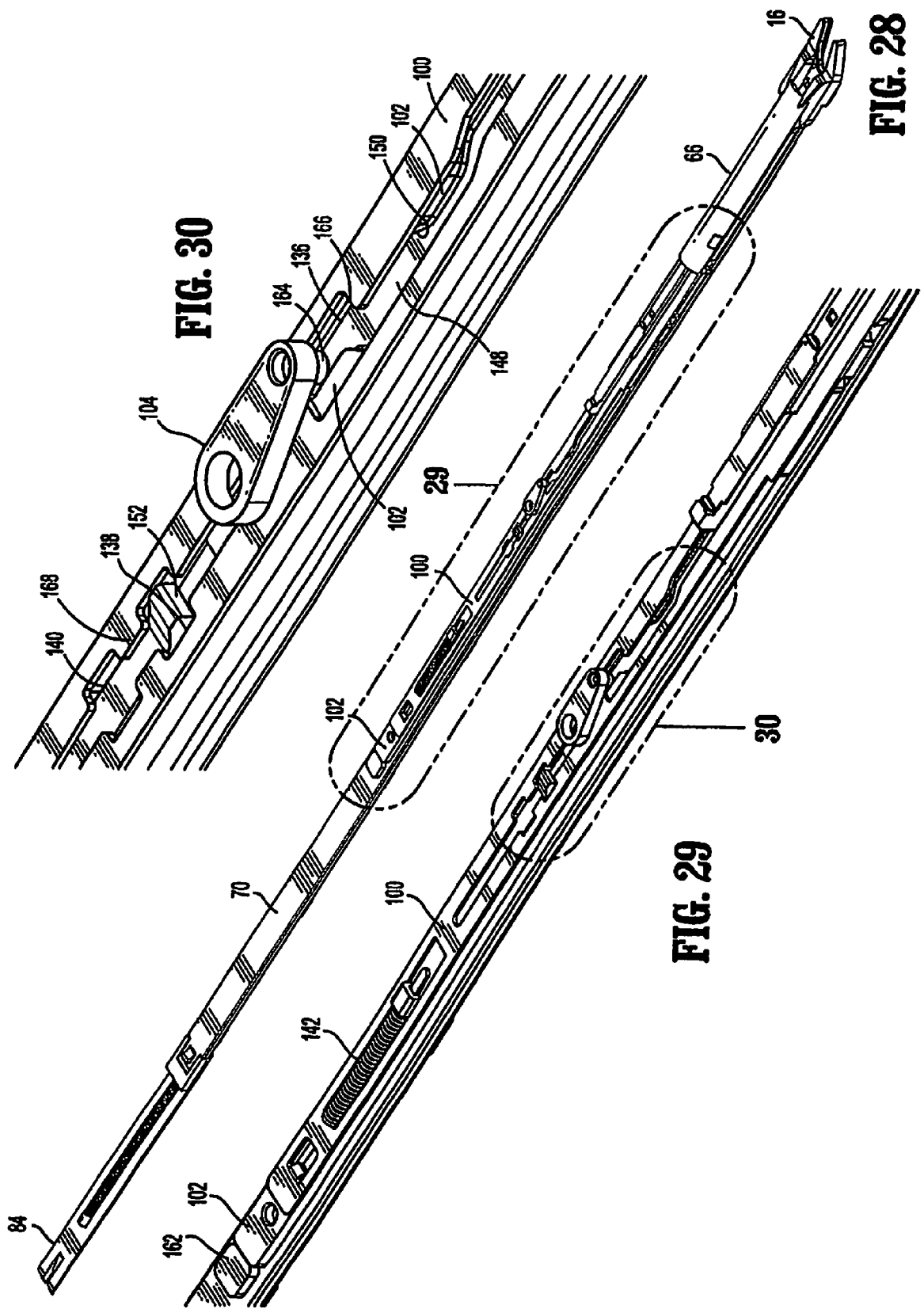

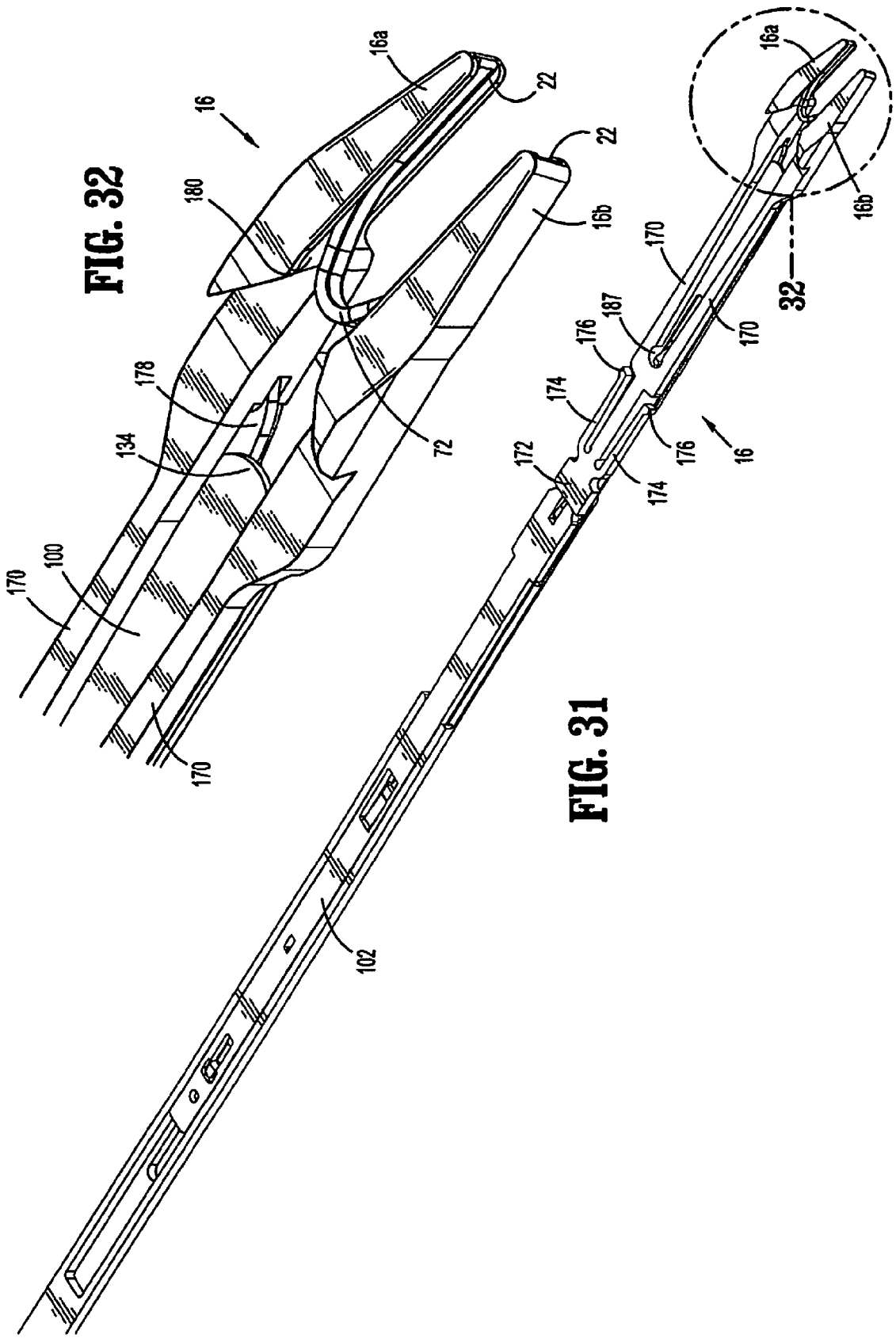

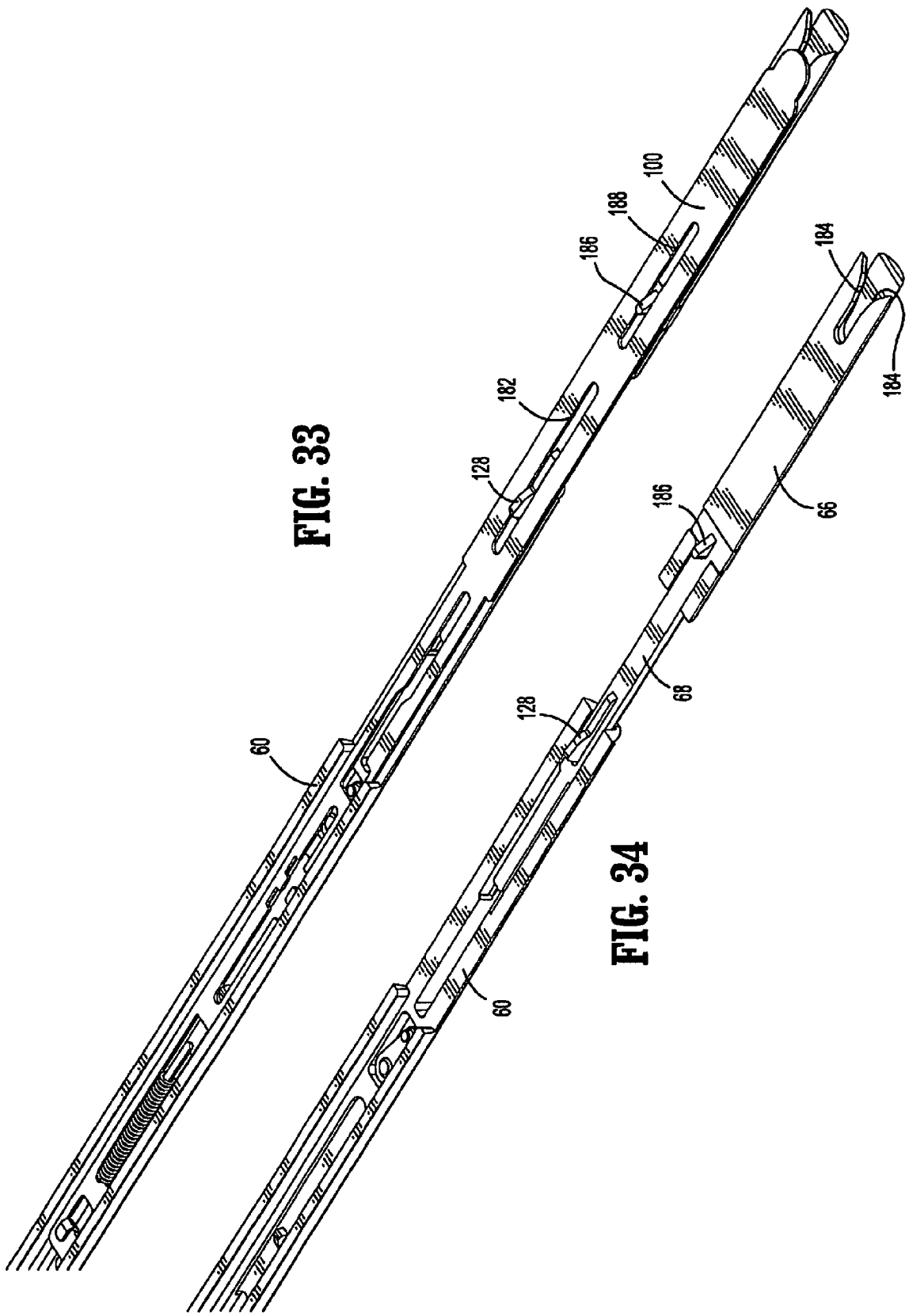

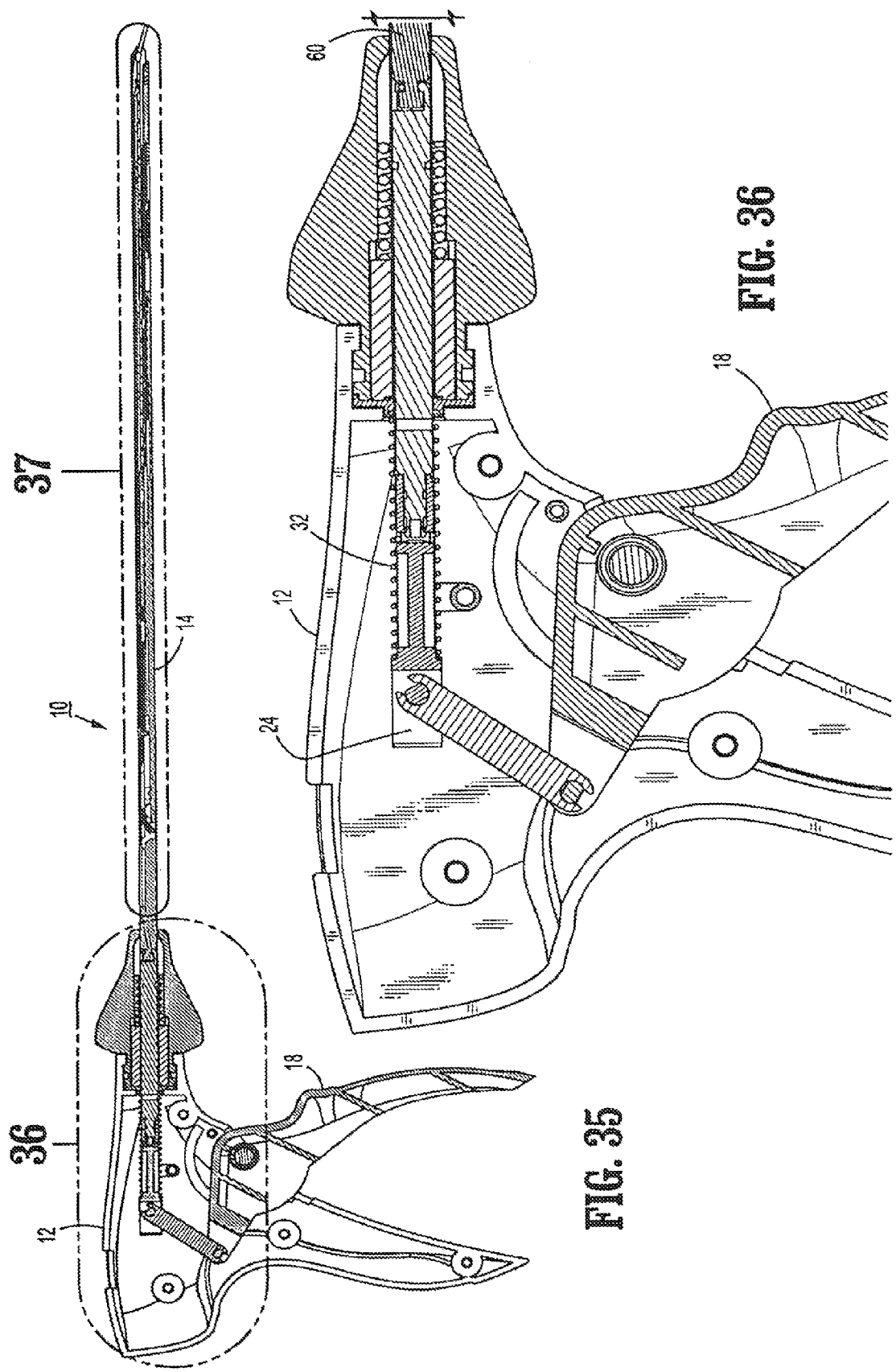

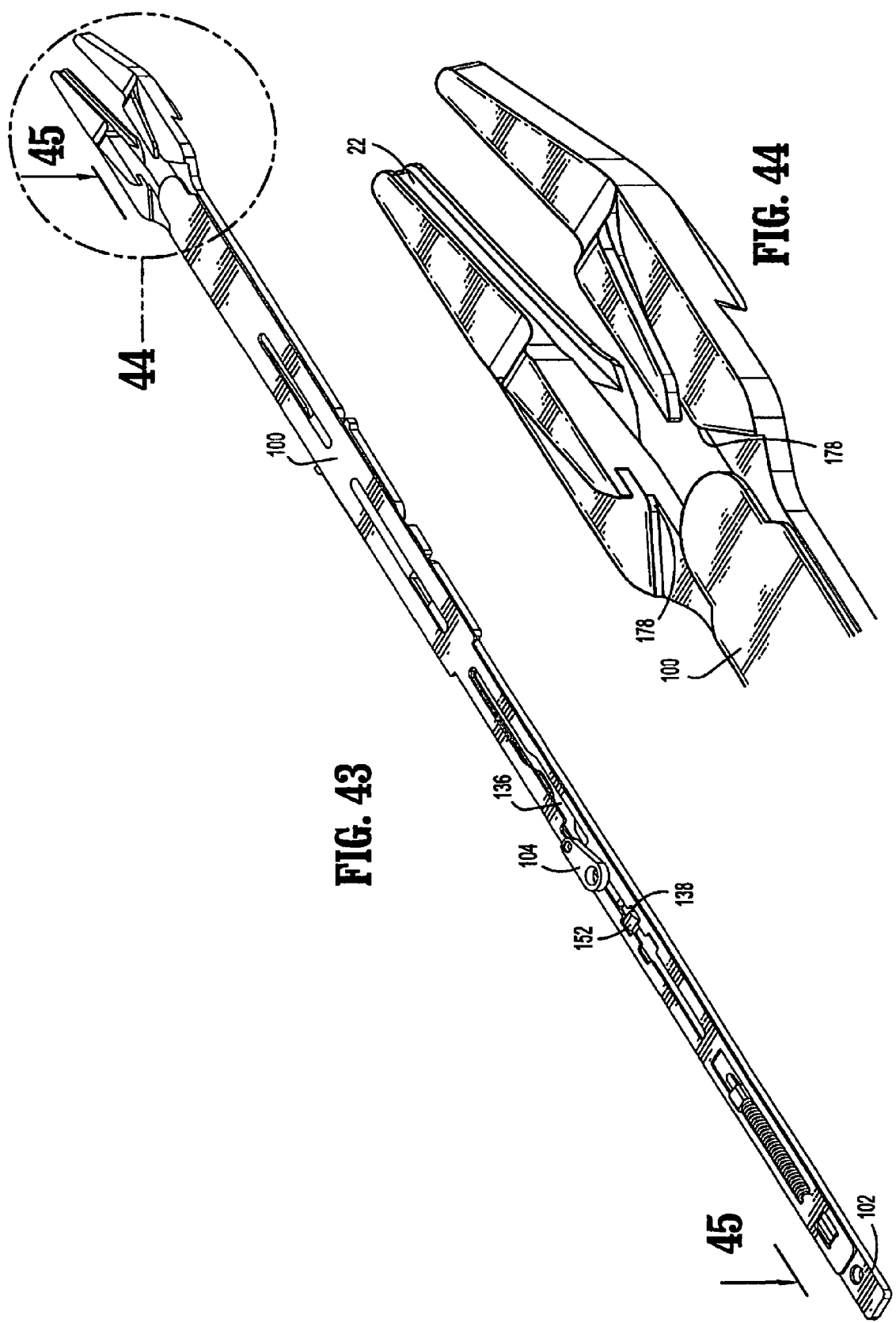

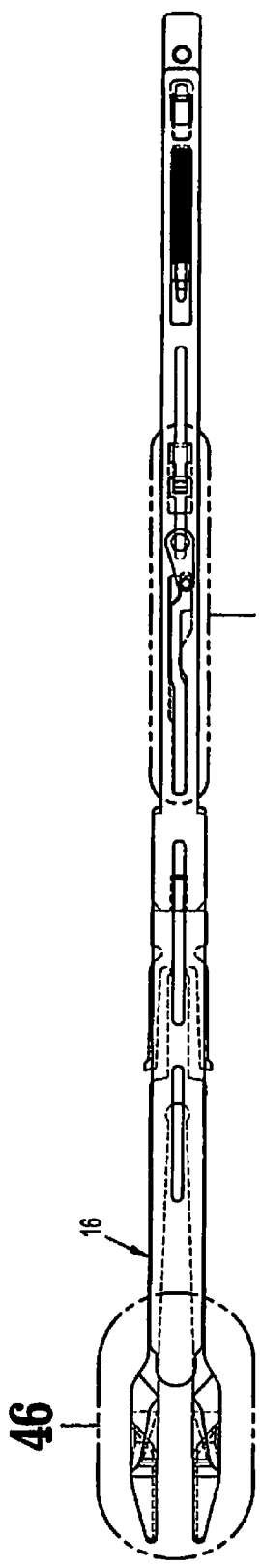
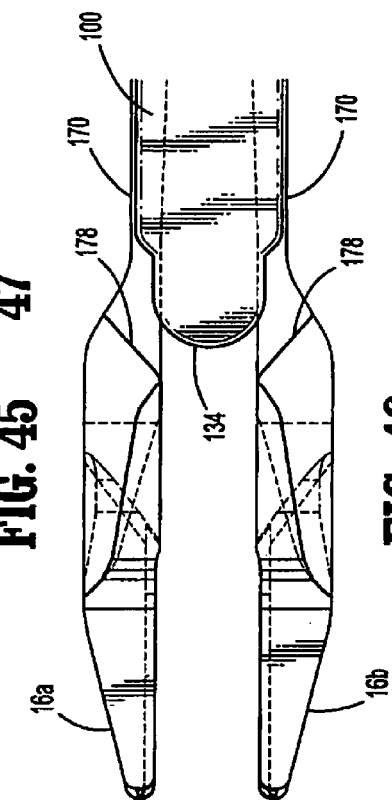
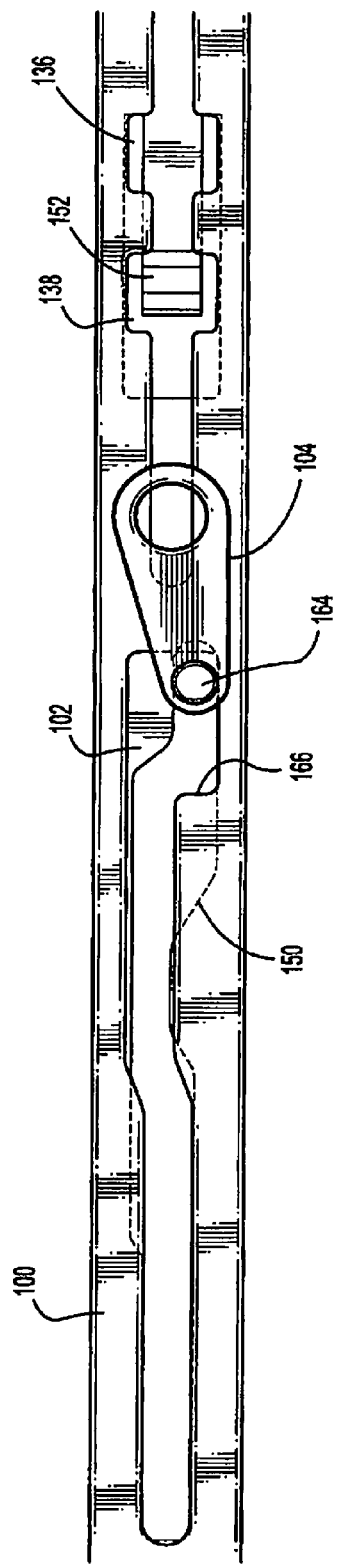
FIG. 45
FIG. 46
FIG. 47

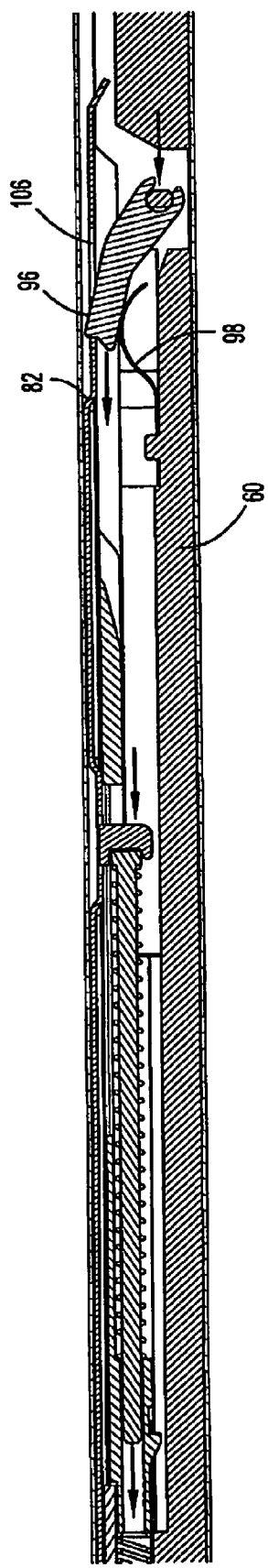
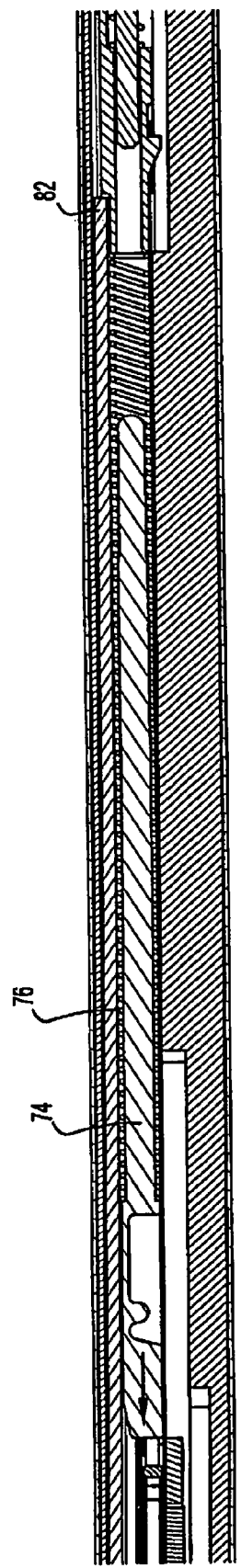
FIG. 51
FIG. 52

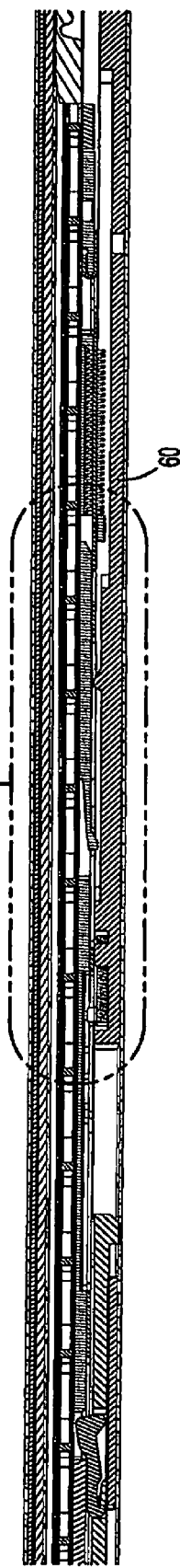
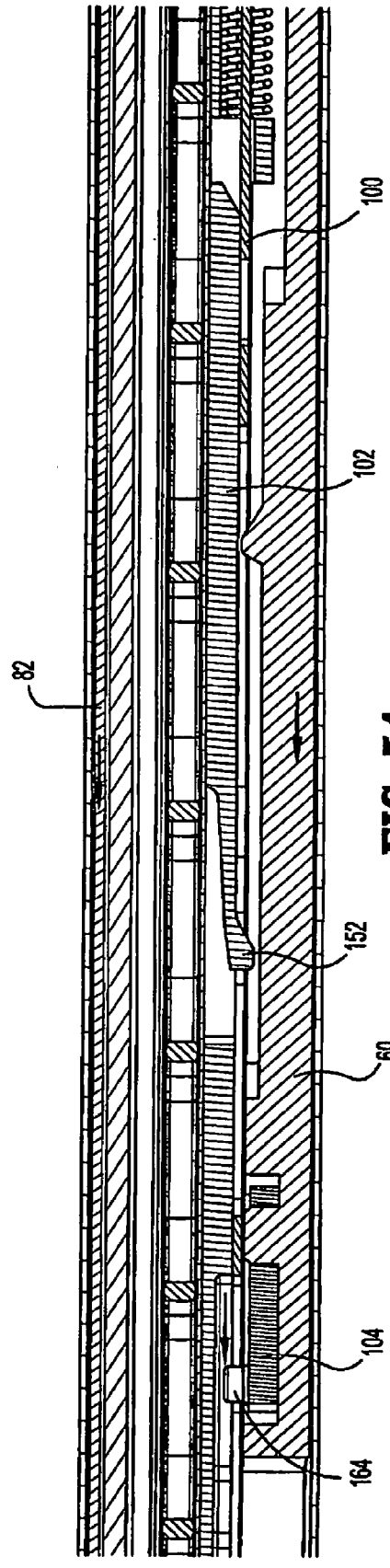

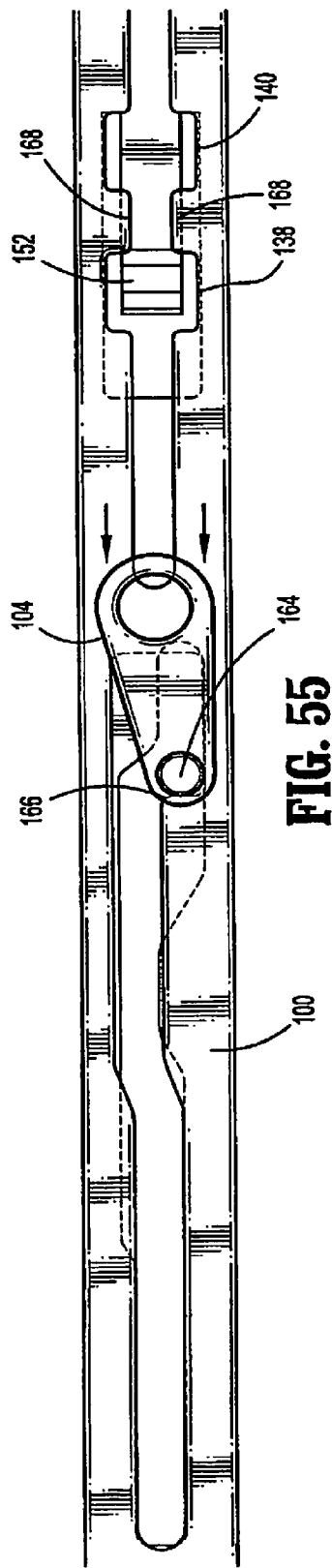

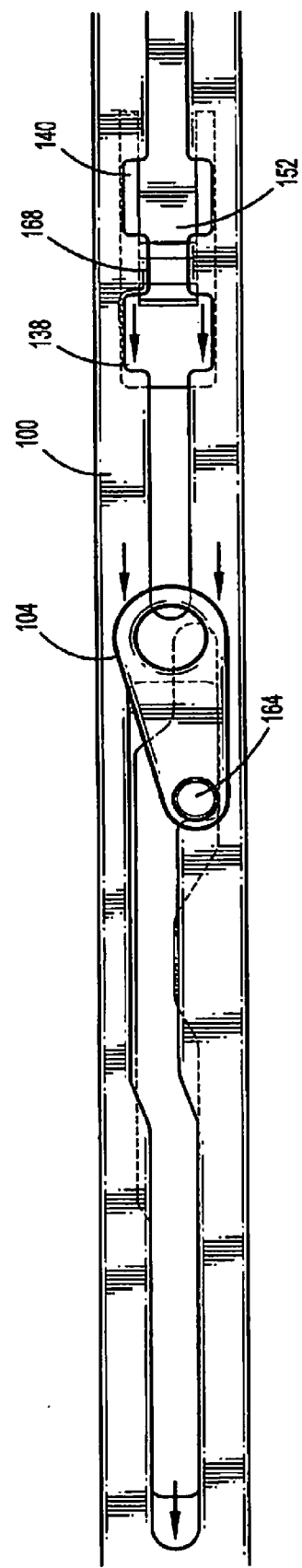
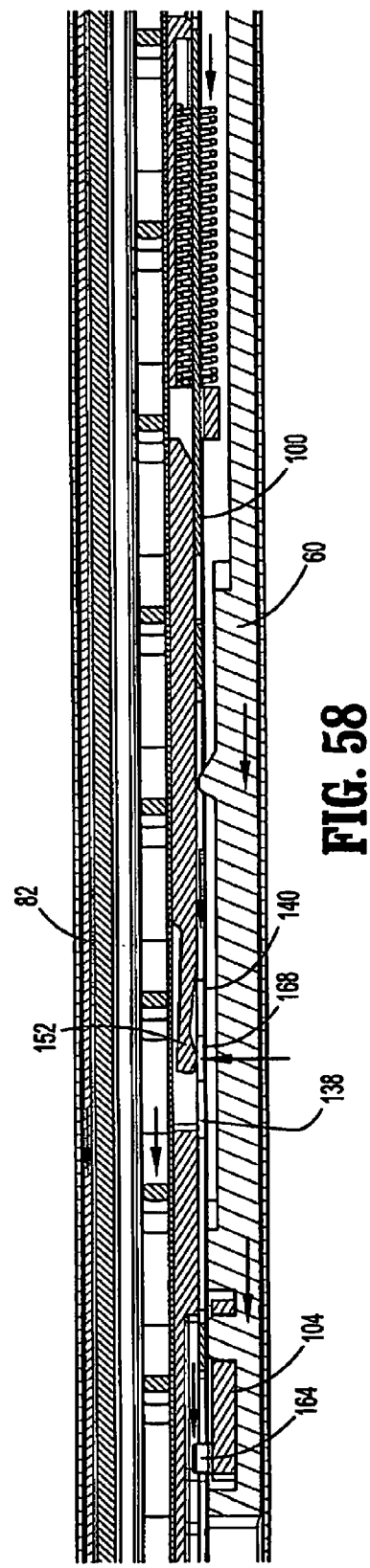
FIG. 57
FIG. 58

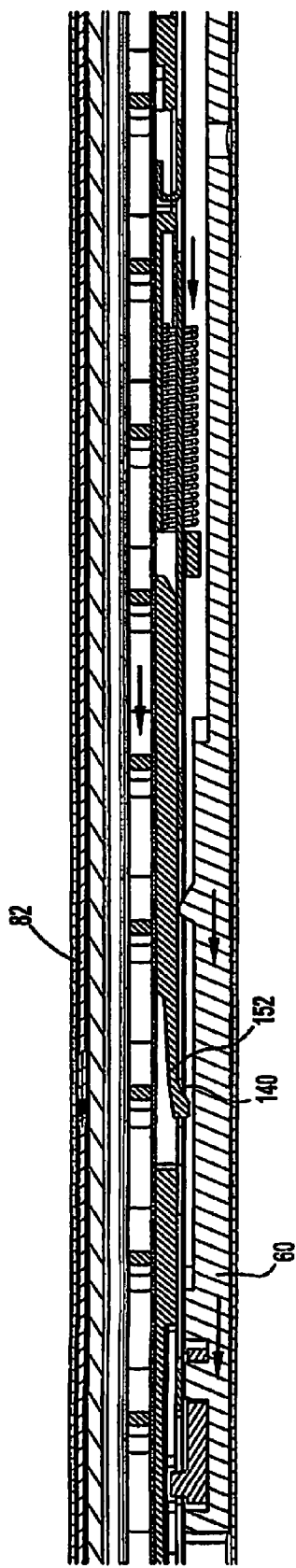
FIG. 61
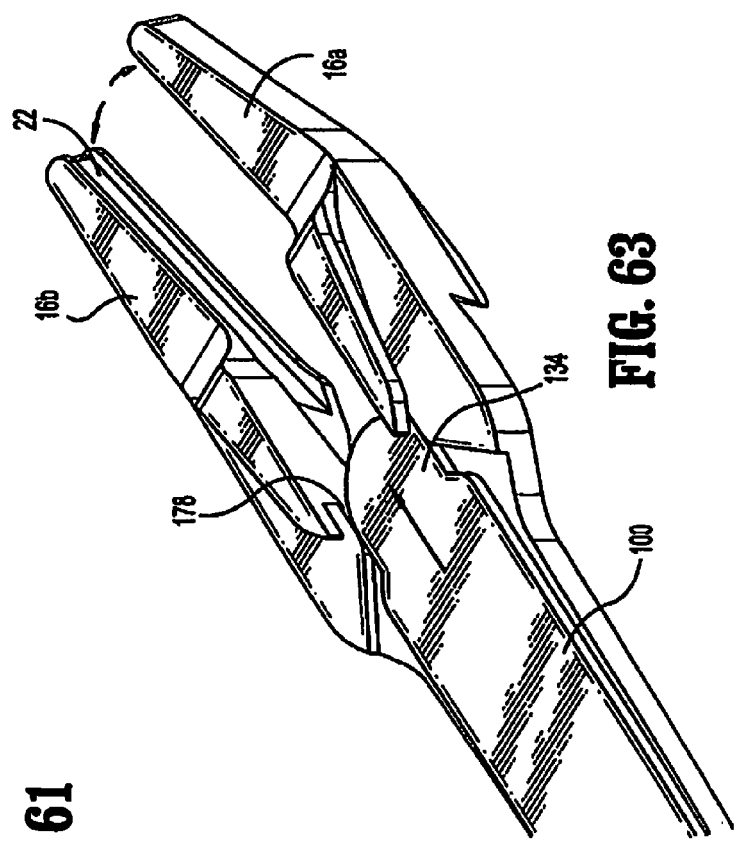
FIG. 63
FIG. 62

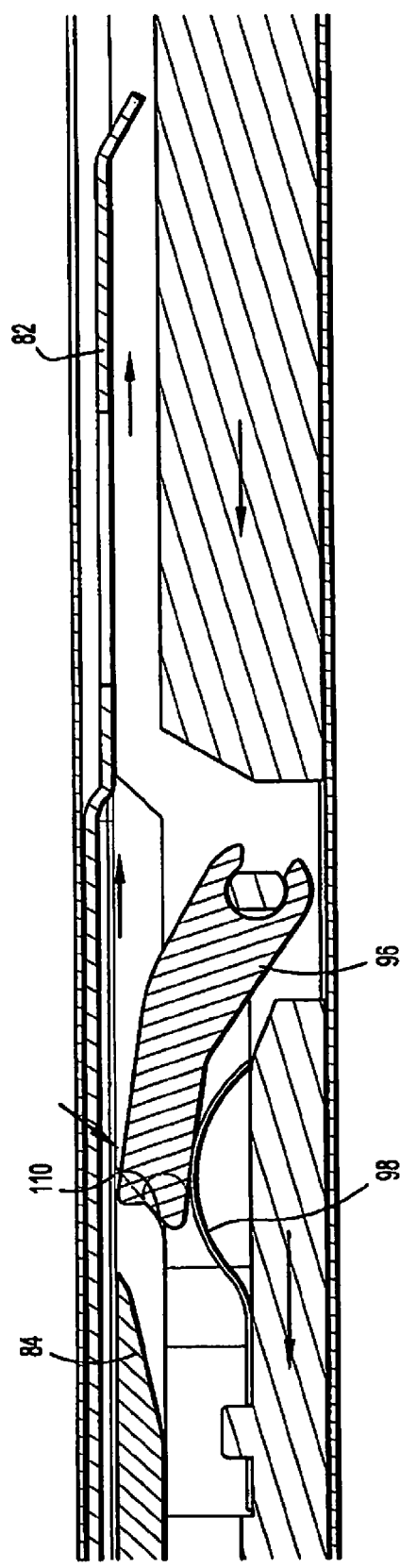
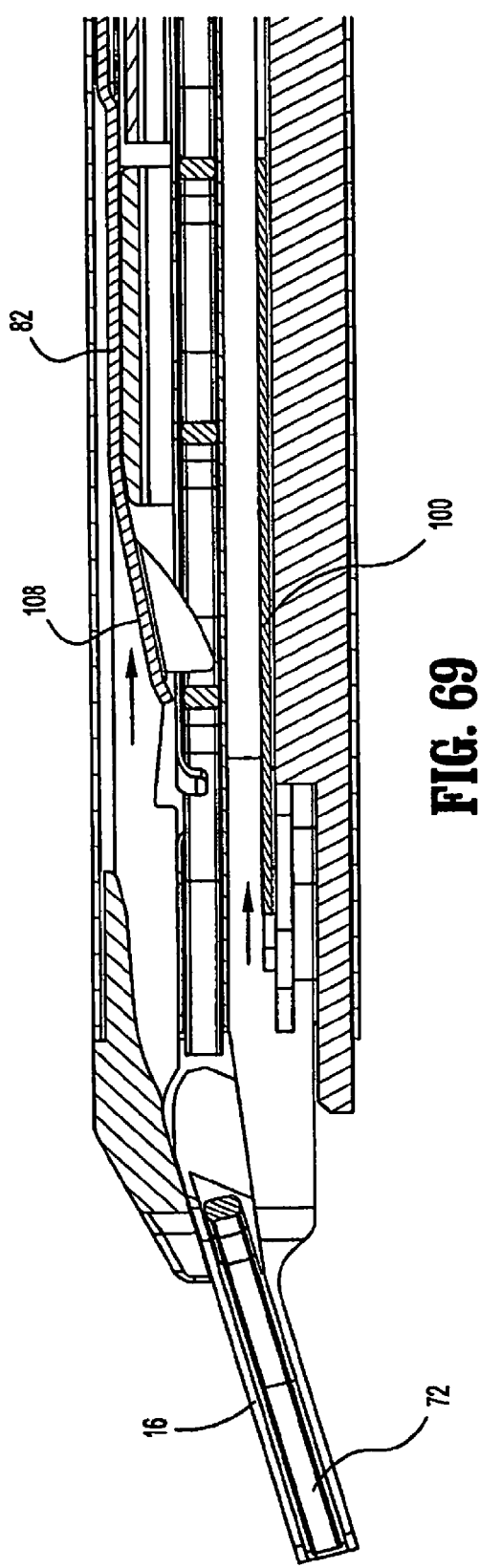

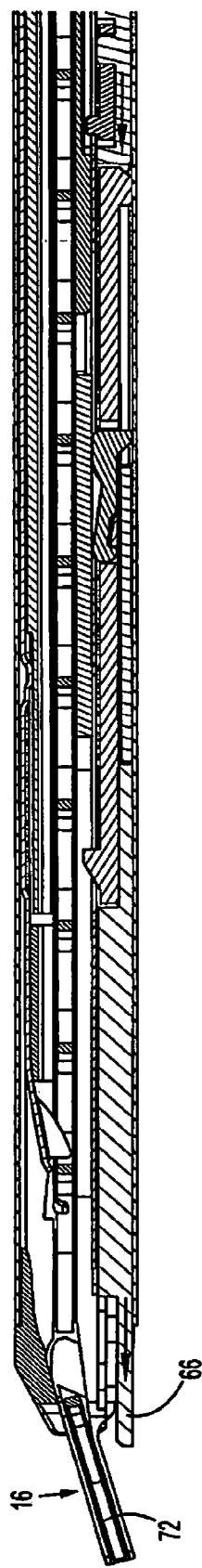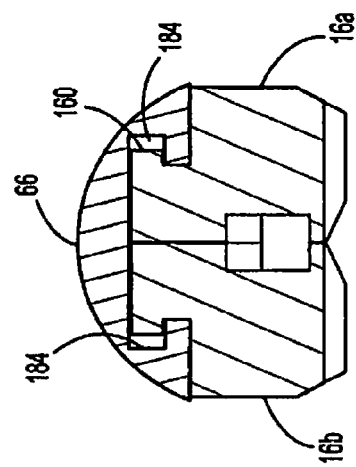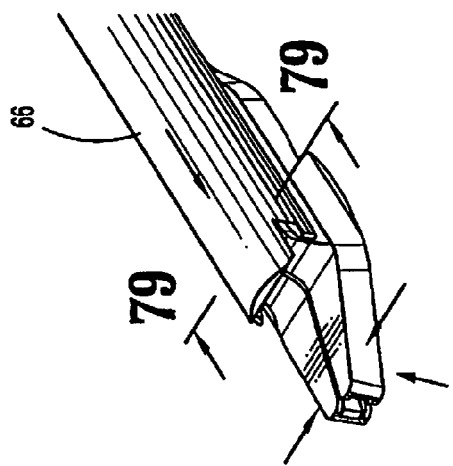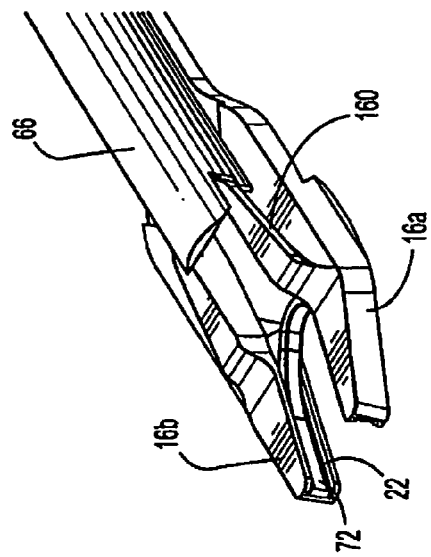
FIG. 76
FIG. 77
FIG. 78
FIG. 79

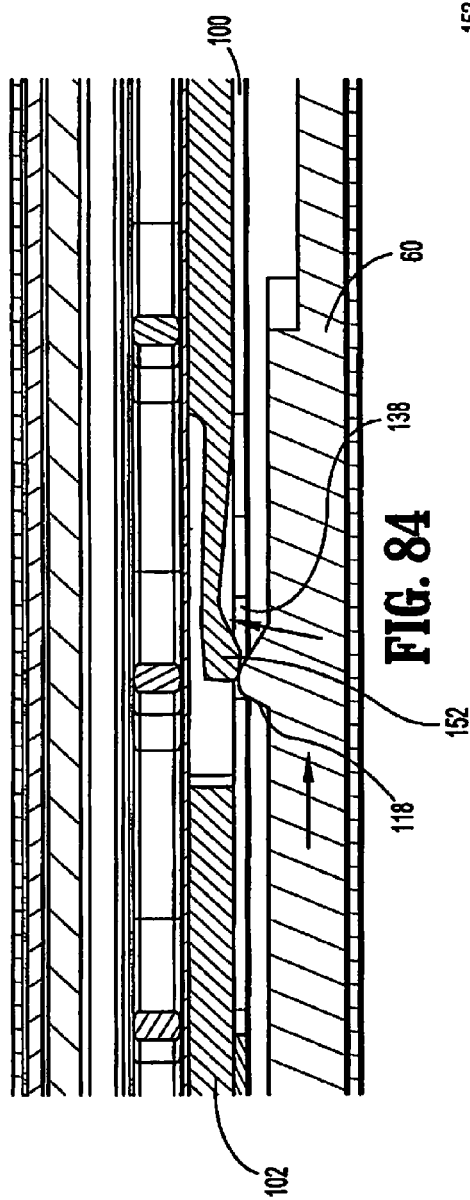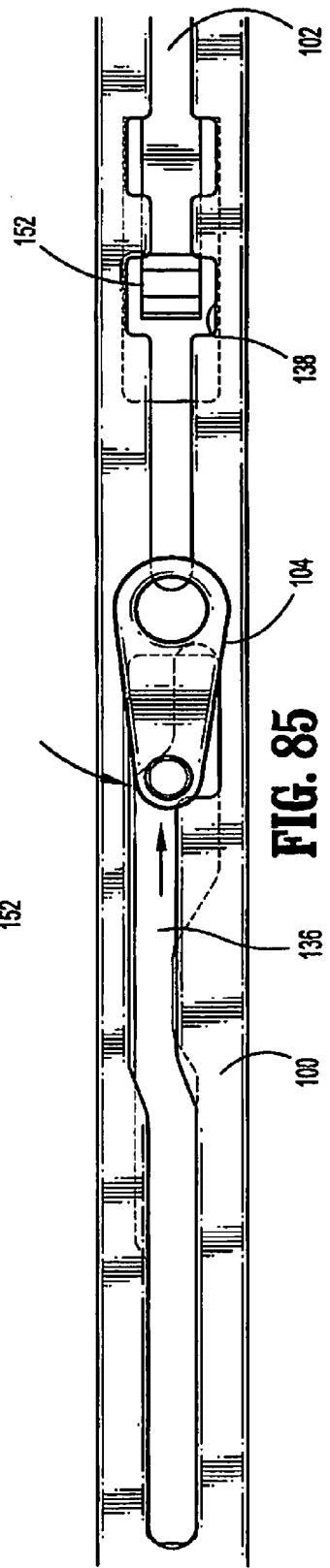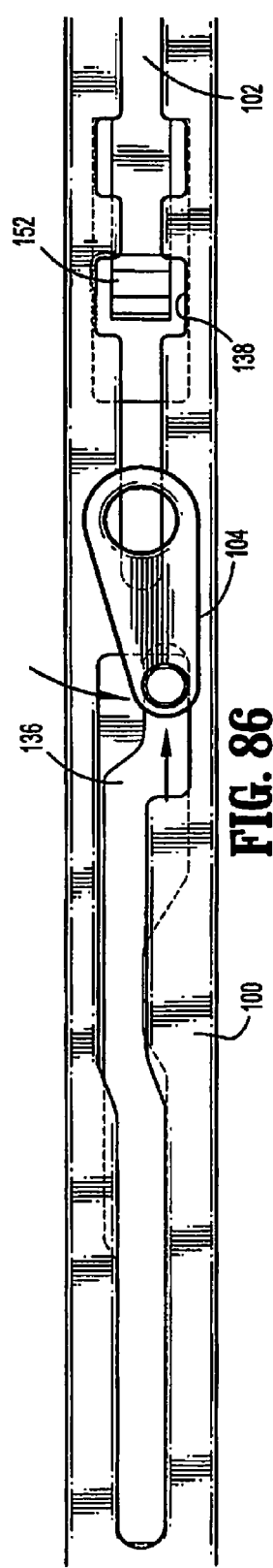

ENDOSCOPIC SURGICAL CLIP APPLIER

CROSS REFERENCE TO RELATED PATENT APPLICATIONS

The instant patent application is a Continuation of U.S. patent application Ser. No. 11/245,493, filed on Oct. 7, 2005, which is now U.S. Pat. No. 7,717,926, which claims priority to each of U.S. Provisional Patent Application Ser. No.: 60/617,104, filed on Oct. 8, 2004, and U.S. Provisional Patent Application Ser. No.: 60/617,016, filed on Oct. 8, 2004, which are both herein incorporated by reference in their entirety.

TECHNICAL FIELD

The technical field relates to surgical clip appliers and more particularly to an endoscopic surgical clip applier having a mechanism for stabilizing the jaw structure during the insertion of a surgical clip.

DESCRIPTION OF THE RELATED ART

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such single clip appliers are typically fabricated from a biocompatible material and are usually compressed over a vessel. Once applied to the vessel, the compressed clip terminates the flow of fluid therethrough.

One significant design goal is that the surgical clip be loaded between the jaws without any compression of the clip from the loading procedure. Such bending or torque of the clip during loading is disfavored and care is exercised to prevent any damage to the jaws and/or the clip or compression to the clip by a force during loading. This compression could slightly alter the alignment of the clip between the jaws, or damage the clip causing the surgeon to remove the clip from between the jaws for discarding the clip. Additionally such preloading compression may slight compress parts of the clip and change the geometry of the clip. This will cause the surgeon to remove the compressed clip from between the jaws for discarding the clip. Accordingly, there is a need for an apparatus that eliminates one or more of the aforementioned drawbacks and deficiencies of the art.

SUMMARY

According to a first aspect of the present disclosure, there is provided an apparatus for application of surgical clips to body tissue. The apparatus has a handle portion with a body extending distally from the handle portion defining a longitudinal axis and a plurality of surgical clips disposed within the body. The apparatus also has a jaw assembly mounted adjacent a distal end portion of the body with the jaw assembly including first and second jaw portions movable between a spaced-apart and an approximated position. The apparatus further has a wedge plate longitudinally movable between the first and the second jaw portions, and a clip pusher configured to individually distally advance a surgical clip to the jaw assembly while the jaw portions are in the spaced apart position with an actuator. The actuator is at least partially disposed within the body and longitudinally movable in response to actuation of the handle portion and has a cam link. The apparatus also has a jaw closure member positioned adjacent the first and second jaw portions to move the jaw portions to the approximated position. The cam link longitudinally moves wedge plate between the first and the second jaw portions.

According to another aspect of the present disclosure, the apparatus has the wedge plate biasing the first and the second jaw portions when said wedge plate is longitudinally moved between the first and the second jaw portions and the wedge plate maintains the first and the second jaw portions in a fixed predetermined relationship during loading of the clip. The fixed predetermined relationship prevents flexing of the first and the second jaw members during clip loading.

According to another aspect of the present disclosure, the apparatus has the wedge plate with a rounded distal tip.

According to another aspect of the present disclosure, the apparatus has the wedge plate with a first proximal window. The first proximal window is adapted to be engaged by a member disposed in the body with the member being configured to hold the wedge plate in a distal most position. The distal most position being between the first and the second jaw members.

According to another aspect of the present disclosure, the apparatus has the wedge plate with a second proximal window. The second proximal window is adapted to be engaged by the member and the second proximal window is configured to hold the wedge plate in a proximal most position retracted from the first and the second jaw members. The proximal most position of the wedge plate is configured to allow the first and the second jaw members to be moved to the approximated position to compress the clip.

According to another aspect of the present disclosure, the apparatus has the first proximal window connected to the second proximal window by a longitudinal slot.

According to another aspect of the present disclosure, the apparatus has the member movable from the second proximal window to first proximal window by moving the wedge plate distally.

According to still another aspect of the present disclosure, the apparatus has the cam link engageable with a cam slot in the wedge plate. The cam slot has a driving edge.

According to another aspect of the present disclosure, the member is a flexible leg.

According to another aspect of the present disclosure, the apparatus has the cam slot with a proximal side and a distal side. At the distal side, the cam link traverses past the driving edge at a demarcation line. At the demarcation line, the cam link terminates distal movement of the wedge plate.

According to another aspect of the present disclosure, the apparatus has the wedge plate further comprising a biasing device. At the demarcation line, the disengagement between the cam link and the driving edge permits the biasing device to retract the wedge plate.

According to another aspect of the present disclosure, the cam link disengages the wedge plate at the demarcation line, and the disengagement of the cam link permits retraction of the rounded distal end from between the first and the second jaw members.

According to another aspect of the present disclosure, there is provided an apparatus for application of surgical clips to body tissue. The apparatus has a handle portion and a body extending distally from the handle portion and defining a longitudinal axis with a plurality of surgical clips disposed within the body and a jaw assembly mounted adjacent a distal end portion of the body. The jaw assembly has first and second jaw portions movable between a spaced-apart and an approximated position. The apparatus also has a clip pusher configured to individually distally advance a surgical clip to the jaw assembly while the jaw portions are in the spaced apart position and an actuator at least partially disposed within the body and longitudinally movable in response to actuation of the handle portion. The actuator is biased to longitudinally move proximally. The apparatus also has a jaw closure member positioned adjacent the first and second jaw portions to move the jaw portions to the approximated position and a rack having a plurality of ratchet teeth being connected to the actuator with a pawl biased to the handle portion. The pawl has at least one tooth configured to engage the ratchet teeth. As the actuator is moved longitudinally, the plurality of ratchet teeth are passed over the pawl and the pawl is configured to prevent inadvertent return of the actuator before full actuation of the apparatus.

According to another aspect of the present disclosure, the pawl is biased by a spring and the spring is connected to the handle portion to bias the pawl into engagement with the rack.

According to another aspect of the present disclosure, the apparatus has the pawl is pivotally mounted in the handle portion.

According to another aspect of the present disclosure, when actuation of the handle portion is terminated in mid stroke, the ratchet teeth restrain the pawl against proximal motion, and any inadvertent partial actuation of the jaw assembly is prevented.

According to another aspect of the present disclosure, the apparatus has the first jaw and second portions moved to the approximated position and the ratchet teeth are advanced a predetermined distance past the pawl to permit retraction of the actuator.

According to another aspect of the present disclosure, there is provided an apparatus for application of surgical clips to body tissue. The apparatus has a handle assembly with a handle and a trigger movable relative to the handle, and a body extending distally from the handle portion and defining a longitudinal axis. The apparatus also has a plurality of surgical clips disposed within the body and a jaw assembly mounted adjacent a distal end portion of the body with the jaw assembly including first and second jaw portions movable between a spaced-apart and an approximated position. The apparatus further has a clip pusher configured to individually distally advance a surgical clip to the jaw assembly while the jaw portions are in the spaced-apart position and an actuator at least partially disposed within the body and longitudinally movable in response to actuation of the handle portion. The apparatus also has a link connected at a first end to the actuator and connected at a second end to the trigger with a jaw closure member positioned adjacent the first and second jaw portions to move the jaw portions to the approximated position.

According to another aspect of the present disclosure, the link is connected to a rack having a plurality of ratchet teeth and the ratchet teeth are connected to a pawl and are configured to prevent inadvertent return of the actuator before full actuation of the apparatus.

According to another aspect of the present disclosure, the apparatus has the pawl biased to the handle. As the trigger is actuated the link is advanced distally and the link advances the rack distally. The pawl ratchet teeth slide along the pawl.

According to another aspect of the present disclosure, the apparatus has the pawl is pivotally connected to the handle.

BRIEF DESCRIPTION OF THE DRAWINGS

A particular embodiment of a surgical clip applier is disclosed herein with reference to the drawings wherein;

FIG. 1 is a perspective view of a surgical clip applier;

FIG. 2 is another perspective view of the surgical clip applier of FIG. 1;

FIG. 3 is an enlarged perspective view of the jaw structure of the surgical clip applier;

FIG. 4 is a top view of the surgical clip applier;

FIG. 5 is a side view of the surgical clip applier;

FIG. 6 is a side view, with half of the body removed, of the handle assembly of the surgical clip applier;

FIG. 10A is a perspective view of a feed bar;

FIG. 10B is a perspective view of a follower and surgical clips;

FIGS. 10C and 10D are opposite perspective views of a trip block;

FIG. 10E is a perspective view of a spindle;

FIG. 10G is an enlarged area of detail of FIG. 10E;

FIG. 10F is an enlarged area of detail of FIG. 10E;

FIG. 11 is a perspective view of the distal end of the spindle and a driver;

FIG. 12 is a perspective view of a trip lever mechanism on the spindle;

FIGS. 14 and 15 are opposite perspective views of a filler component;

FIG. 16 is a perspective view of the rotation knob and shaft assembly;

FIG. 17 is a perspective view of the overpressure assembly;

FIG. 18 is a perspective view of the spindle and jaw assembly;

FIG. 19 is an enlarged area of detail of the spindle and jaw assembly of FIG. 18;

FIG. 20 is an enlarged area of detail of the spindle and trip lever of FIG. 18;

FIG. 22 is a perspective view of the surgical clip applier shaft assembly with parts removed;

FIG. 23 is an enlarged area at detail of FIG. 22;

FIG. 24 is an enlarged area of detail of FIG. 22;

FIG. 25 is an enlarged area of detail of FIG. 22;

FIG. 26 is a perspective view of the spindle, driver and jaw assembly;

FIG. 27 is an enlarged area of detail of FIG. 26;

FIG. 27A is a cross-sectional view taken along line 27A-27A of FIG. 27.

FIG. 28 is a perspective view of the cam link and wedge plate assembly;

FIG. 29 is an enlarged area of detail of FIG. 28;

FIG. 30 is an enlarged area of detail of FIG. 29;

FIG. 31 is a perspective view of the filler component and jaw assembly;

FIG. 32 is an enlarged perspective view of the jaw assembly of FIG. 31;

FIGS. 33 and 34 are perspective views of the distal end of the spindle including wedge plate and driver;

FIG. 35 is a side view, partially shown in section, of the surgical clip applier in a pre-fired condition;

FIG. 36 is in enlarged area of detail of FIG. 35;

FIG. 43 is a perspective view of the wedge plate and jaw assembly;

FIG. 44 is an enlarged area of detail of FIG. 43 showing the wedge plate and jaw members;

FIG. 45 is a top view of FIG. 43 taken along line 45-45;

FIG. 46 is an enlarged area of detail of FIG. 45 showing the jaw and the wedge plate;

FIG. 47 is an enlarged area of detail of FIG. 45 showing the wedge plate and cam link;

FIG. 51 is a side view, shown in section, of the feed bar and trip lever;

FIG. 52 is a side view, shown in section, of the follower;

FIG. 53 is a side view, shown in section, of the endoscopic portion of the surgical clip applier;

FIG. 54 is an enlarged area of detail of FIG. 53 illustrating the spindle movement;

FIG. 55 is a top view of the wedge plate and filler component illustrating the movement of the cam link;

FIG. 56 is a side view, shown in section, illustrating the feed bar advancing a clip;

FIG. 57 is a top view of the wedge plate and cam link moving distally;

FIG. 58 is a side view, shown in section, showing the movement of the flexible leg cammed out of a wedge plate window;

FIG. 61 is a side view, shown in section, of the flexible leg and wedge plate disengagement;

FIG. 62 is a top view of the wedge plate entering the jaw structure;

FIG. 63 is a perspective view illustrating the wedge plate camming open the jaw structure;

FIG. 68 is a side view, shown in section, illustrating the trip lever being cammed out of engagement with the feed bar by means of a trip block;

FIG. 69 is a side view, shown in section, illustrating the retraction of the wedge plate and feed bar;

FIG. 76 is a side view, shown in section, of the driver camming the jaws closed about a surgical clip;

FIGS. 77 to 79 are sequential views of the driver camming the jaws closed about a surgical clip;

FIG. 84 is a side view, shown in section, illustrating the spindle retracting; and FIGS. 85 and 86 are top views illustrating the cam link resetting within the wedge plate.

DETAILED DESCRIPTION

Figure 7:
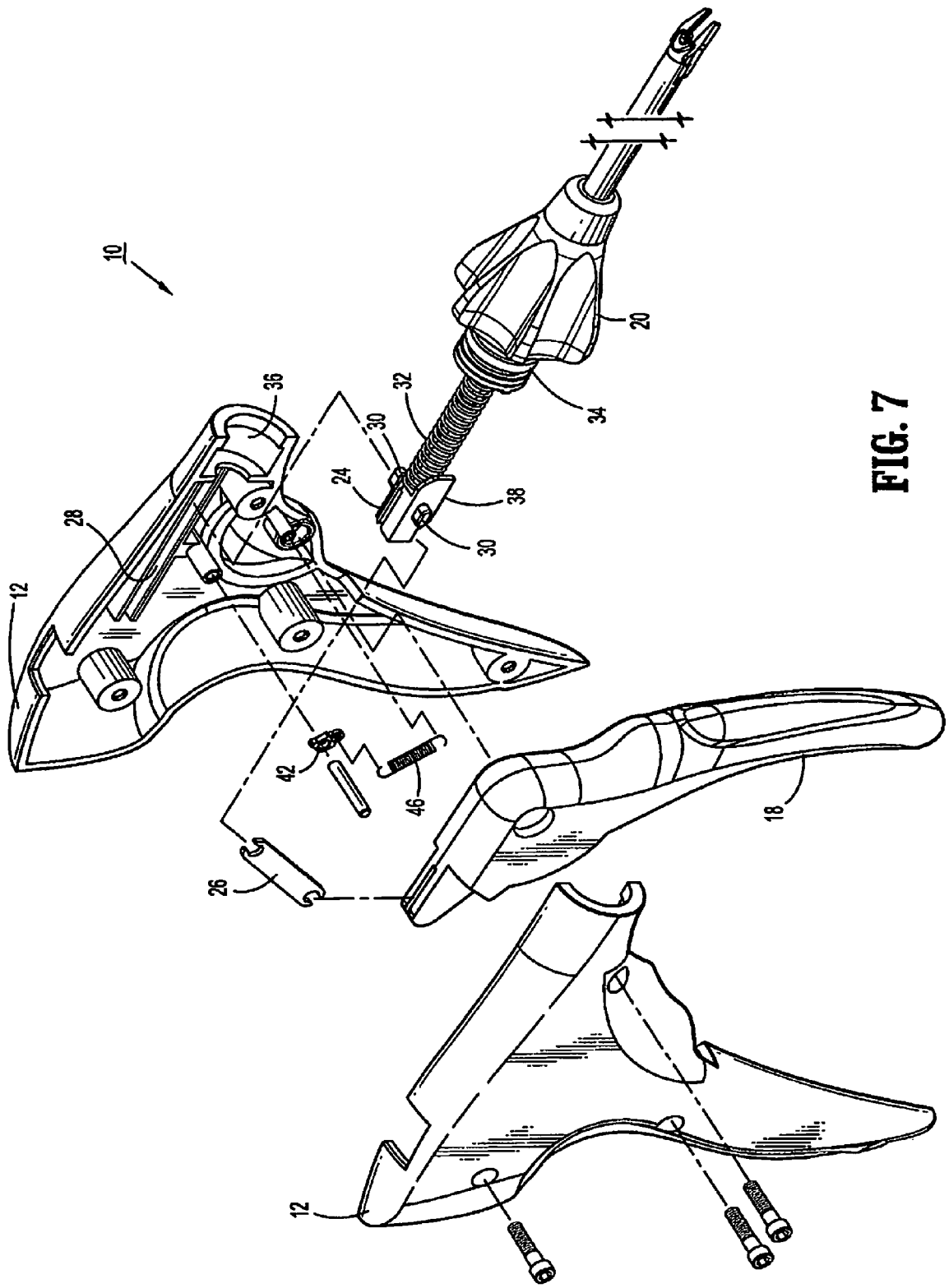
FIG. 7 is an exploded perspective view of the handle of the clip applier, with shaft assembly.
Figure 9:
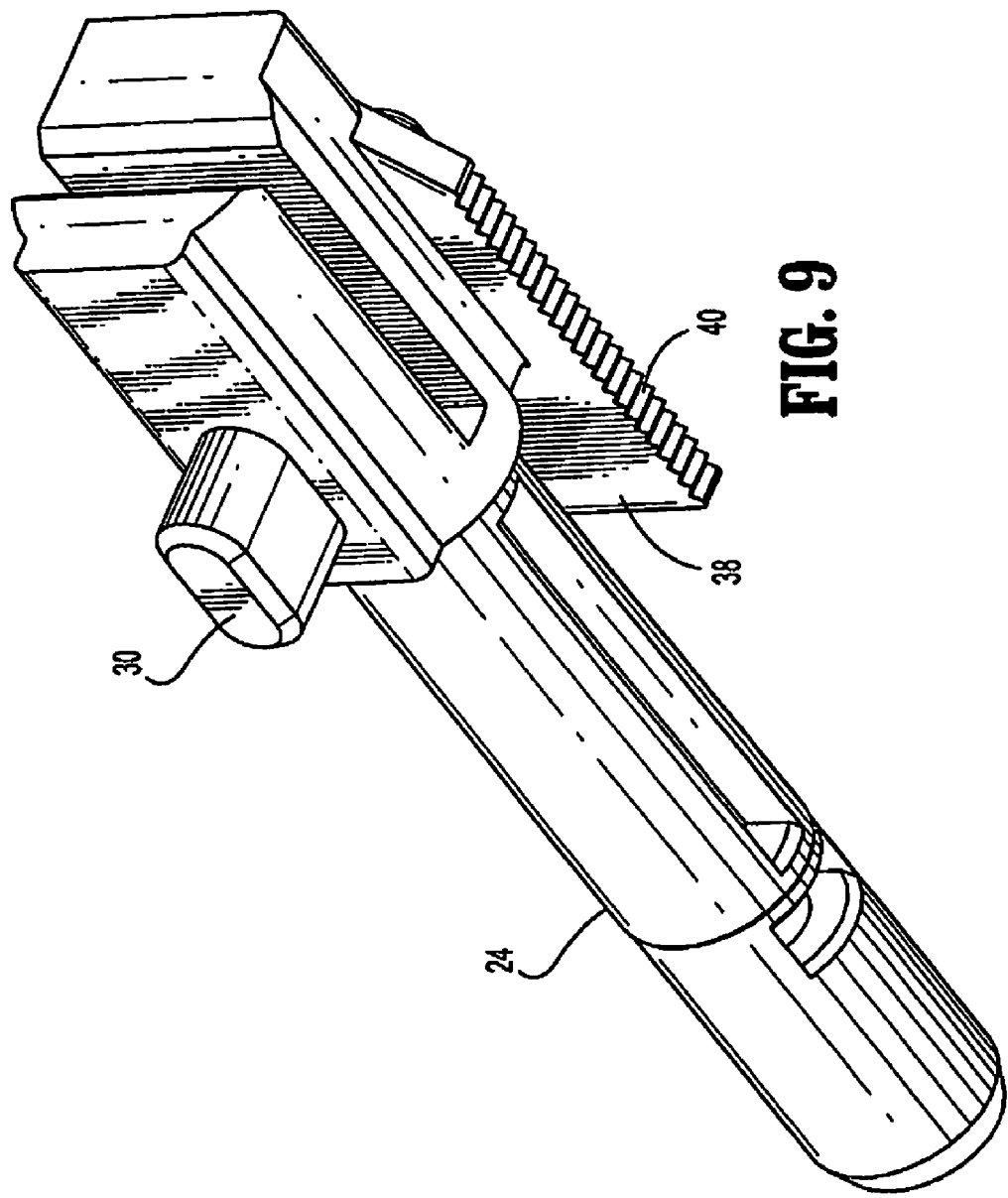
FIG. 9 is a perspective view of a yoke.
Figure 8:
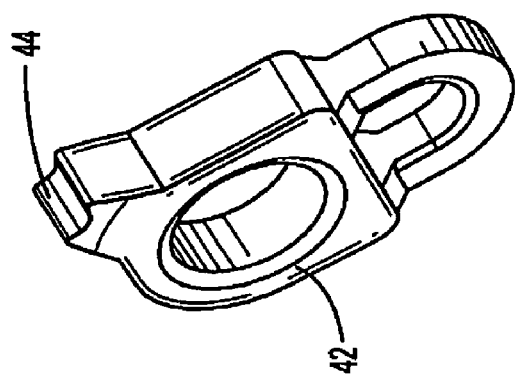
FIG. 8 is a perspective view of a pawl.

There is disclosed a novel endoscopic surgical clip applier having a jaw control mechanism configured to maintain jaws of the surgical clip applier in a spaced apart and stable position during insertion of a surgical clip. It should be noted that, while the disclosed jaw control mechanism is shown and described in an endoscopic surgical clip applier, the disclosed jaw control mechanism is applicable to any surgical clip applier or other instrument having a pair of compressible jaws.

Referring now to FIGS. 1-5, surgical clip applier 10 generally includes a handle assembly 12 and an endoscopic portion including an elongated tubular member 14 extending distally from handle assembly 12. Handle assembly 12 is formed of a plastic material while elongated tubular member 14 is formed of a biocompatible material such as stainless steel. A pair of jaws 16 are mounted on the distal end of elongated tubular member 14 and are actuated by a trigger 18 movably mounted in handle assembly 12. Jaws 16 are also formed of a biocompatible material such as stainless steel or titanium. A knob 20 is rotatably mounted on a distal end of handle assembly 12 and affixed to elongated tubular member 14 to provide 360 degree rotation of elongated tubular member 14 and jaws 16 about its longitudinal axis. Referring for the moment to FIG. 3, jaws 16 define a channel 22 for receipt of a surgical clip therein.

Referring now to FIGS. 6 and 7, handle assembly 12 of clip applier 10 is shown. Handle assembly 12 includes a longitudinally movable yoke 24 connected to trigger 18 by a link 26. Handle assembly 12 includes housing channels 28 to guide yoke wings 30 of yoke 24 within handle assembly 12 during actuation of clip applier 10. Yoke 24 is connected to the drive mechanisms and is biased to a proximal position by a return spring 32. Knob 20 includes a flange 34 which is rotatably mounted in a journal 36 in housing 12.

Referring to FIGS. 6-9, in order to prevent inadvertent return of trigger 18 and yoke 24 before full actuation of surgical instrument 10, yoke 24 includes a rack 38 having rack teeth 40. A pawl 42 is pivotally mounted in handle assembly 12 and includes pawl teeth 44 engageable with rack teeth 40. Pawl 42 is biased into engagement with rack 38 by a spring 46. Rack 38 and pawl 42 prevent release of trigger 18 before full actuation in a manner described in more detail hereinbelow.

Combinations of the various elements and mechanisms associated with clip applier 10 will now be described.

Figure 10:
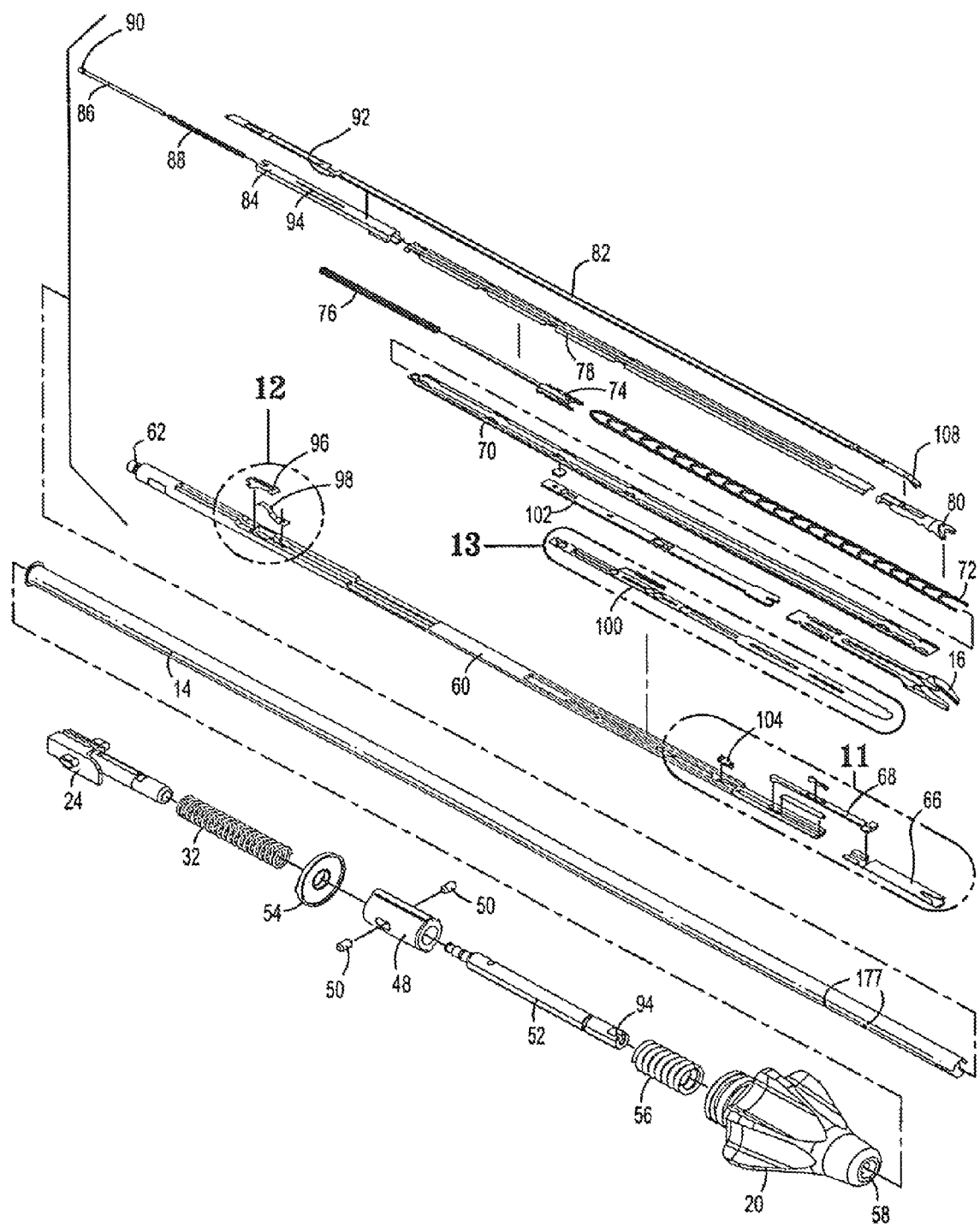
FIG. 10 is an exploded perspective view of the shaft assembly of the surgical clip applier.

Referring to FIG. 10, a bushing 48, including retention pins 50, is provided to secure the bushing 48 to the knob 20. A drive link 52 is connected, typically with a snap type connection, to yoke 24 such that a proximal end of drive link 52 engages yoke 24.

An over pressure mechanism including an impact spring 56 is provided about outer tube 14, between bushing 48 and housed in a bore of knob 20 to prevent over compression of jaws 16 during actuation of the instrument in a manner described in more detail hereinbelow. Drive link 52 extends through a bore 58 in knob 20.

A flange located at a proximal end of elongated tube member 14 abuts a proximal end of bushing 48.

In order to actuate the various components there is provided an actuation mechanism or spindle 60 mounted for longitudinal movement through elongated tubular member 14. Spindle 60 includes a boss 62 at its proximal end which is engageable with a recess 64 on the distal end of drive link 52. A camming mechanism including a driver 66 and a slider joint 68 extend from a distal end of spindle 60 to cam closed jaws 16 about a surgical clip.

Clip applier 10 is configured to retain a plurality of surgical clips for application to tissue. Clip applier 10 includes an elongated channel member 70 configured to retain a plurality of surgical clips 72 and convey surgical clips 72 to jaws 16. It should be noted that channel member 70 and jaws 16 do not move longitudinally relative to elongated tubular member 14. A follower 74 is biased by a spring 76 to urge surgical clips 72 distally within channel member 70. A channel cover 78 overlies channel 70 to retain and guide spring 76 and surgical clips 72 therein. A nose 80 is provided at a distal end of channel cover 78 to assist in directing surgical clips 72 into jaws 16.

Figure 38:
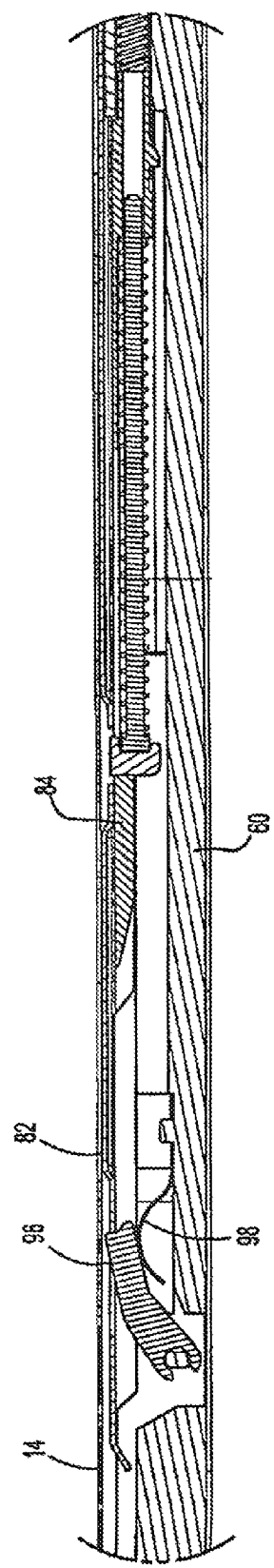
FIG. 38 is in enlarged area of detail of FIG. 37 showing the trip lever.

A feeder mechanism including a feed bar 82 is provided for longitudinal movement relative to channel cover 78 in order to advance individual clips 72 into jaws 16. A trip block 84 having a guide pin 86 and a feed bar spring 88 are provided adjacent the proximal end of channel cover 78 to bias feed bar 82 in a proximal direction. Specifically, a proximal end 90 of guide pin 86 is interconnected with a hook 92 on an underside of feed bar 82 (FIGS. 38A & B) and through slot 94 in trip block 84. (See also FIGS. 10 A, C, & D) In order for spindle 60 to move feed bar 82, spindle 60 is provided with a trip lever 96 and a biasing spring 98. Trip lever 96 is engageable with a proximal end of feed bar 82 in a manner described in more detail herein below.

A notable advantage of presently disclosed clip applier 10 is that it is provided with a wedge plate 100 which is configured to advance into jaws 16 during actuation of surgical clip applier 10 and maintain jaws 16 in a spaced apart condition while receiving a surgical clip 72. Cam slot 136 (FIG. 13), described in detail hereinbelow, formed through wedge plate 100 and a filler component 102 mounted within elongated tubular member 14, cooperate in connection with a cam link 104, provided on spindle 60, to move wedge plate 100 relative to filler component 102 and jaws 16. Filler component 102 is positioned directly behind jaws 16 and does not move relative to elongated tubular member 14.

Turning to FIG. 10A, and as noted above, feed bar 82 is provided to move surgical clips 72 into jaws 16. Feed bar 82 is driven by trip lever 96 on spindle 60. (See FIG. 10.) Specifically, feed bar 82 is provided with an elongated window 106 which is configured to be engaged by trip lever 96 as spindle 60 is driven distally. To facilitate insertion of the clip into jaws 16, feed bar 82 is provided with a pusher 108 at its distal end which is configured to advance an individual clip 72 out of the line of clips 72 and into jaws 16. As shown in FIG. 10B, follower 74 is positioned behind the line of clips to advance clips 72 through surgical clip applier 10.

Referring to FIG. 10C, as noted above, trip block 84 includes a slot 94 to receive hook 92 of feed bar 82. In order to disengage trip lever 96 from window 106 and thus feed bar 82, trip block 84 is provided with an angled surfaces 110 which is configured to engage trip lever 96 and disengage it from window 106 of feed bar 82 as best shown in FIG. 10D.

Referring now to FIGS. 10E-10G, various features of spindle 60 will now be described. A perspective view of spindle 60, isolated from other components is shown in FIG. 10E. With specific reference to FIG. 10F, at a proximal end, spindle 60 includes a pivot point 112 for attachment of trip lever 96 at its proximal end. Additionally, a boss 114 is provided in spindle 60 for attachment of biasing spring 98 to bias trip lever 96 into engagement with window 106 of feed bar 82. Similarly, with respect to FIG. 10G, at a distal end, spindle 60 is provided with a boss 116 for mounting cam link 104. Spindle 60 is additionally provided with a raised feature 118 which functions to disengage filler component 102 from wedge plate 100 in a manner described in hereinbelow.

Referring to FIG. 11, spindle 60 is provided to advance driver 66 into engagement with jaws 16 to close jaws 16 about a surgical clip after the surgical clip has been positioned within jaws 16. A distal end 120 of slider joint 68 resides in a recess 122 in driver 66. A proximal projection 124 of slider joint 68 rides within a longitudinal slot 126 in the distal end of spindle 60. The length of longitudinal slot 126 allows spindle 60 to move a predetermined longitudinal distance before engaging and moving driver 66 longitudinally to close jaws 16 about a clip 72. A latch retractor 128 is provided within a slot 130 in slider joint 68 so as to allow driver 66 to be driven distally after wedge plate 100 has been allowed to retract proximally in a manner described in more detail hereinbelow. A spindle guard 132 is provided between latch retractor 128 and the surface of spindle 60 to prevent damage to the plastic surface of spindle 60 by the surface of latch retractor 128.

Figure 13:
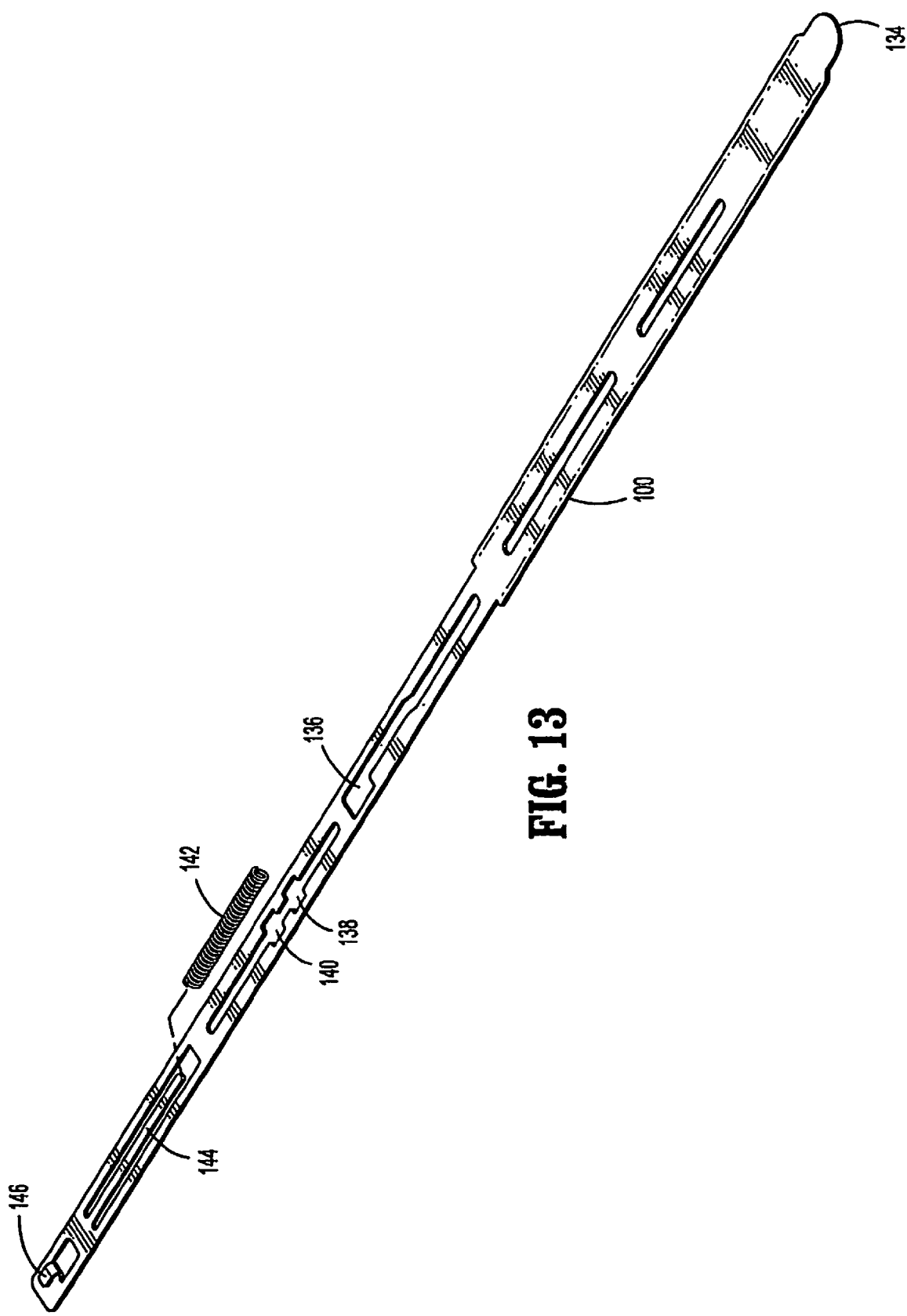
FIG. 13 is a perspective view of a wedge plate and biasing spring.

Referring now to FIG. 13, wedge plate 100 will be described in more detail. As noted above, wedge plate 100 is provided to maintain jaws 16 in a spaced apart condition during loading of a surgical clip 72 within jaws 16. Additionally, the presence of wedge plate 100 provides stability to jaws 16 to prevent them from flexing during loading of surgical clip 72. As shown, wedge plate 100 includes a distal tip 134 which is configured to engage and cam jaws 16 open and maintain them in a spaced condition. Additionally, wedge plate 100 includes a cam slot 136 which is configured to cooperate with cam link 104 mounted on spindle 60 to control the motions of wedge plate 100 as discussed in more detail below. Further, distal and proximal windows 138 and 140, respectively, are provided to engage flexible structure on the filler component 102. A biasing spring 142 is provided on a mount 144 to bias wedge plate 100 generally proximally within elongated tubular member 14. Finally, a stop 146 is configured to engage corresponding structure on filler component 102.

Referring now to FIGS. 14 and 15, various aspects of filler component 102 will now be described. Filler component 102 includes a flexible leg 152 which is configured to engage distal and proximal windows 138 and 140 in wedge plate 100. Filler component 102 also includes an elongated cam slot 148 configured to receive part of cam link 104. A disengaging edge 150 is provided within cam slot 148 to facilitate disengaging cam link 104 from within cam slot 136 in wedge plate 100. Filler component 102 additionally includes a recess 154 for engagement with stop 146 on wedge plate 100 (FIG. 13), to limit the proximal retraction of wedge plate 100, as well as a longitudinal recess 156 to accommodate the length of return spring 142 of wedge plate 100.

FIGS. 16 and 17 illustrate the position of impact spring 56 relative to rotation knob 20. As noted above, impact spring 56 is provided as an over pressure mechanism to prevent over compression of jaws 16 during the crimping of a surgical clip 72 as described in more detail below with respect to the operation of surgical clip applier 10. The over pressure mechanism is designed to prevent overstroke of trigger 18 applied by the surgeon and ultimately prevent damage to jaws 16.

Referring to FIGS. 18-20, spindle 60 and related drive components are shown with elongated tubular member 14 removed. Specifically, with regard to FIG. 19, pusher 108 of feed bar 82 extends through a slot 158 in nose 80 to engage a surgical clip 72. Similarly, as shown in FIG. 20, at a proximal end of spindle 60, trip lever 96 extends through window 106 in feed bar 82. In this position, trip lever 96 can engage an edge of slot 106 to drive feed bar 82 distally along with spindle 60 through elongated tubular member 14.

Figure 21:
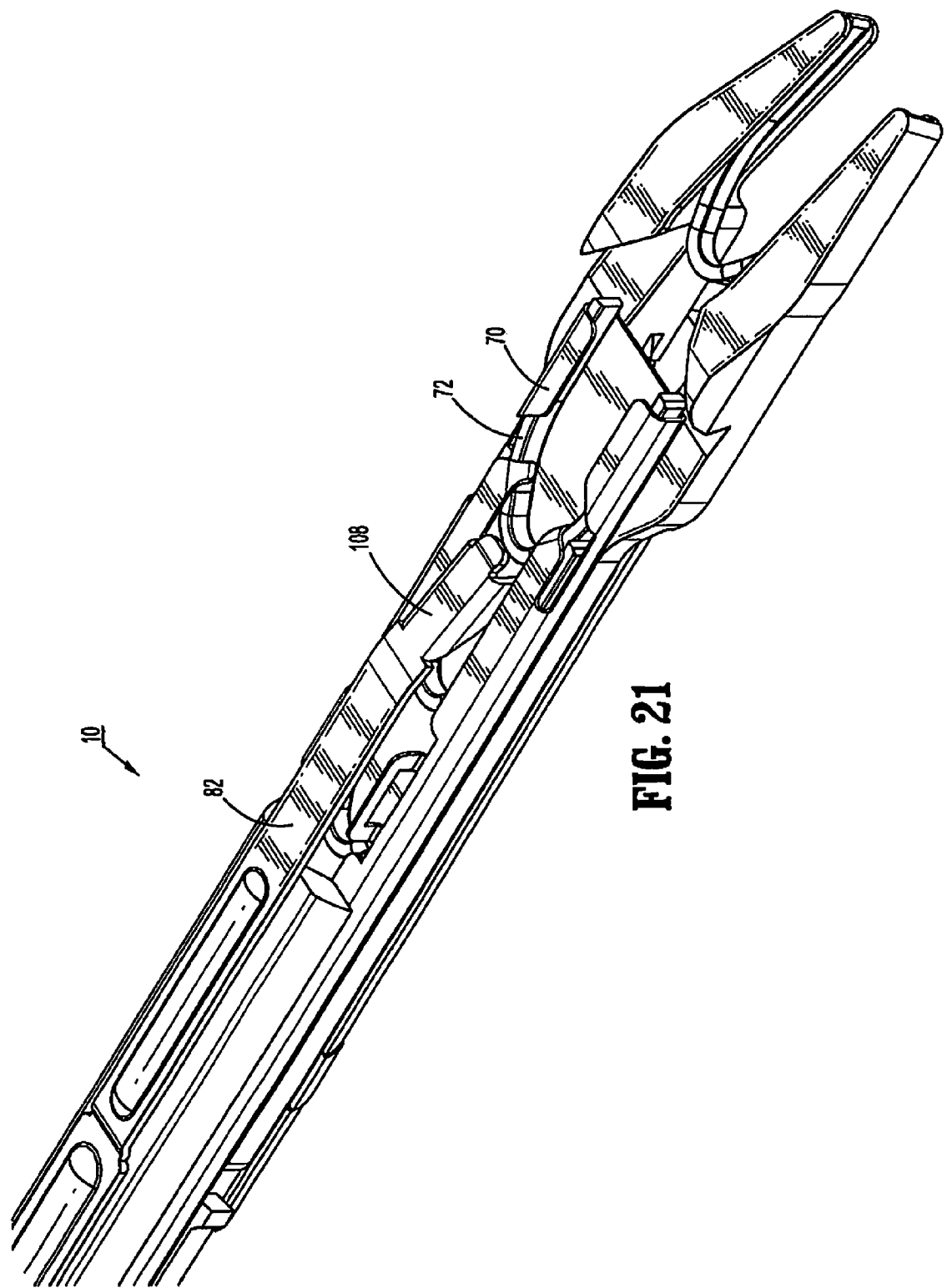
FIG. 21 is an enlarged view of the distal end of the surgical clip applier with outer tube removed.
Figure 37:
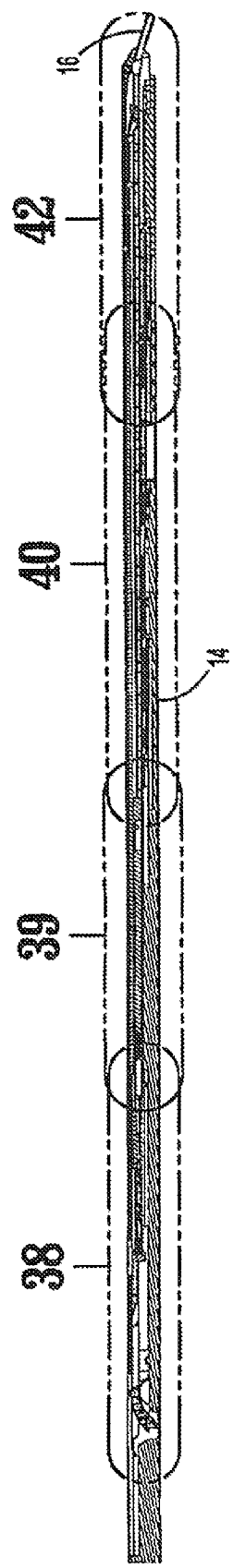
FIG. 37 is an enlarged area of detail of FIG. 35.

Referring to FIG. 21, there is a view similar to FIG. 19, however, nose 80 has been removed to illustrate pusher 108 engaging a surgical clip 72 located in channel 70.

Referring now to FIG. 22, spindle 60 and associated components are shown with feed bar 82 removed.

Referring to FIG. 23, there are illustrated multiple clips 72 positioned within channel 70 for supply to jaws 16 at a distal end of spindle 60. Clips 72 are arranged in longitudinal alignment within channel 70. Retention fingers 71 are provided at a distal end of channel 70 to restrain a stack of clips 72 within channel 70 until advanced into jaws 16 by feed bar 82.

Referring to FIG. 24, there is illustrated an intermediate section of spindle 60 assembled with follower 74 and follower spring 76. As noted, spring 76 biases follower 74 distally relative to spindle 60.

With reference to FIG. 25, there is illustrated spindle 60 assembled with trip lever 96 and biasing spring 98, with trip lever 96 being biased into a upward most position by biasing spring 98.

Referring to FIGS. 26 and 27, an opposed side of spindle 60 assembled with driver 66 about jaws 16 is illustrated. As noted above, driver 66 is configured to cam jaws 16 closed about a surgical clip. Thus, jaws 16 include angled camming surfaces 160 for receipt of corresponding camming surfaces 184 (FIG. 34) of driver 66. A pocket 187 (FIG. 31) in the proximal end of jaws 16 limits the retraction of driver 66. Specifically, protrusion 186 of slider joint 68 engages pocket 187 of jaws 16. (See FIGS. 31 & 34).

Referring for the moment to FIG. 27A, camming surfaces 160 on jaws 16 and corresponding camming surfaces 184 of driver 66 are smoothly rounded, curved or radiused. By forming these camming surfaces in this manner, the friction between camming surfaces 160 and 184 is greatly reduced providing an improved smooth closure of jaws 16 about clip 72.

Referring to FIGS. 28-30, the relative assembled positions of channel 70, trip lock 84, wedge plate 100 and filler component 102 will now be described. Referring initially to FIGS. 29 and 30, filler component 102 is positioned on channel 70. Proximal end of filler component 102 abuts a stop 162 positioned on channel 70. The wedge plate 100 lies over filler component 102 in the manner shown. As best shown in FIG. 30, filler component 102 includes a cam slot 148 having a disengaging edge 150 formed within cam slot 148. Similarly, wedge plate 100 includes a cam slot 136. As noted above, a cam link 104 is provided attached to spindle 60 (not shown) in order to drive wedge plate 100 distally. To facilitate driving wedge plate 100, cam link 104 is provided with a cam link boss 164 which rides in cam slots 136 and 148 of wedge plate 100 and filler component 102 respectively. As cam link 104 is advanced distally relative to wedge plate 100 cam link boss 164 engages a driving edge 166 of wedge plate 100 to drive wedge plate 100 distally. In the manner described hereinafter, once cam link 104, and in particular cam link boss 164, engages disengaging edge 150 of filler component 102 cam link boss 164 is cammed out of engagement of driving edge 166.

Referring to FIG. 30, filler component 102 is provided with a flexible leg 152 which is movable between distal and proximal windows 138, 140, respectively, of wedge plate 100. In order to cam flexible leg 152 out of one of the proximal or distal windows, there is provided a cam surface 168 on flexible leg 152 which cams flexible leg 152 out of the windows in response to relative movement of wedge plate 100 relative to filler component 102.

As noted hereinabove, jaws 16 are provided to receive and crimp surgical clips 72 positioned therein. Referring to FIGS. 31 and 32, jaws 16 generally include a pair of flexible legs 170 fixed to a base 172. Jaw members 16A and 16B are located at a distal end of flexible legs 170. A pair of locking arms 174 extend distally from base 172 and terminate in tabs 176. Tabs 176 are configured to engage corresponding holes 177 on elongated tube 14 (FIG. 10) to secure jaws 16 to elongated tube 14. Jaws 16 include channel 22 for receipt of surgical clips 72. As shown, filler component 102 is positioned directly behind jaws 16 and, as with jaws 16, does not move longitudinally relative to outer tubular member 14.

Referring for the moment to FIG. 32, jaws 16 are configured to receive wedge plate 100 such that the distal tip 134 of wedge plate 100 is used to initially separate jaws section 16a and 16b and maintain them in a separated and aligned configuration during insertion of a surgical clip into jaws 16. As noted, this prevents any torquing or flexing of jaw 16a relative to jaw 16b while a surgical clip 72 is being loaded therein. Each of flexible legs 170 includes a cam edge 178 (see FIGS. 44 & 63) to guide distal tip 134 of wedge plate 100 within jaws 16.

Referring to FIG. 33, wedge plate 100 is illustrated positioned on spindle 60 such that latch retractor 128 extends through a slot 182 in wedge plate 100. As best shown in FIG. 34, with wedge plate 100 removed, it can be seen that a distal end of driver 60 is provided with camming surfaces 184. Camming surfaces 184 cooperate with cam surfaces 160 on jaws 16, (see FIG. 27), to cam jaws 16 together in response to longitudinal movement of driver 60 relative to jaws 16. Protrusion 186 on slider joint 68 extends through a slot 188 in wedge plate 100 to limit retraction of slider joint 68 relative to jaws 16.

The operation of surgical clip applier 10 to crimp a surgical clip around a target tissue, such as, for example, a vessel, will now be described. With reference to FIGS. 35 and 36, trigger 18 is in a generally uncompressed state with yoke 24 biased to a proximal-most position by return spring 32. As best shown in FIGS. 37-42, and with initial reference to FIG. 38, in an unfired state, trip lever 96 carried by spindle 60, biased upwardly by biasing spring 98, is positioned adjacent to, and in contact with, a slot in feed bar 82. Trip block 84 is in a distal position relative to trip lever 96.

Figure 39:
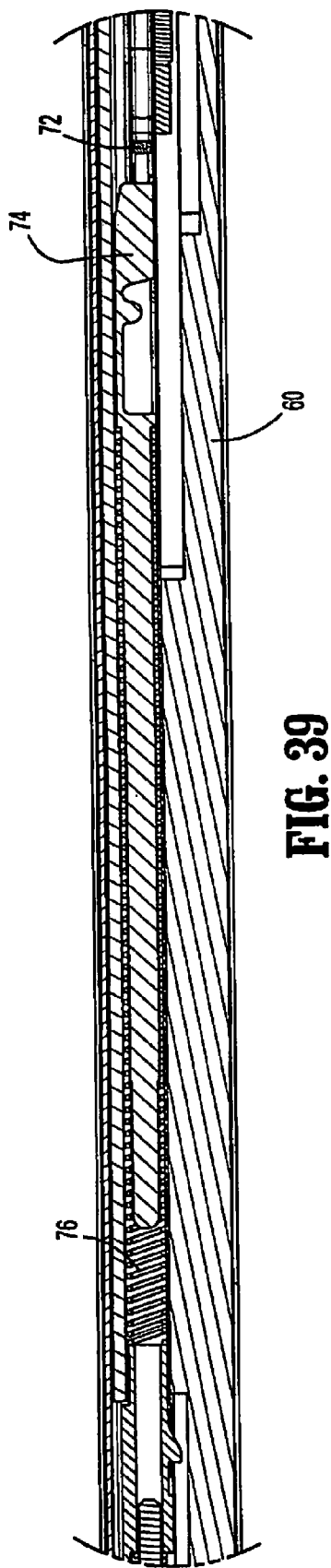
FIG. 39 is an enlarged area of detail of FIG. 37 showing the follower.

Referring to FIG. 39, follower 74 is biased distally by a spring 76 such that clips 72 are biased in a distal direction.

Figure 40:
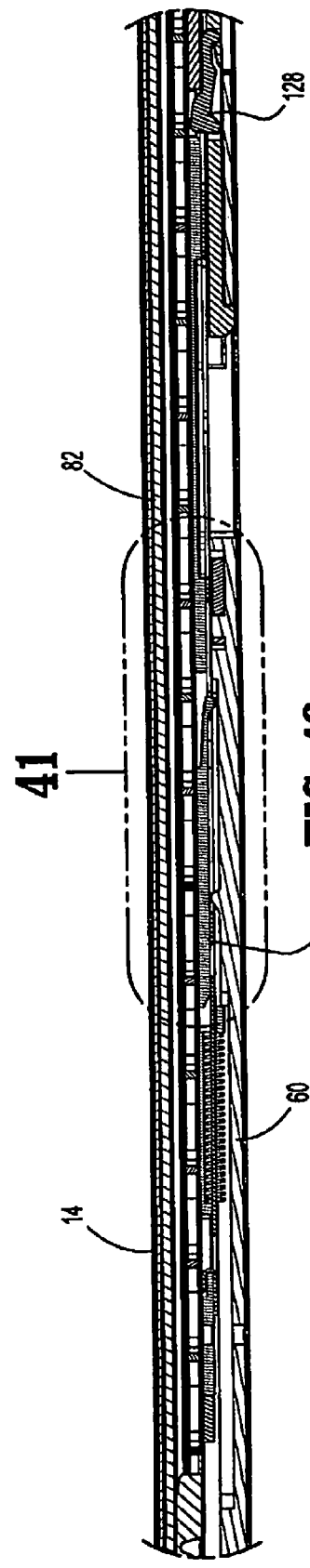
FIG. 40 is an enlarged the area of detail of FIG. 37.

Referring to FIG. 40, spindle 60 and feed bar 82 are stationery with latch retractor 128 biased to an upward position.

Figure 41:
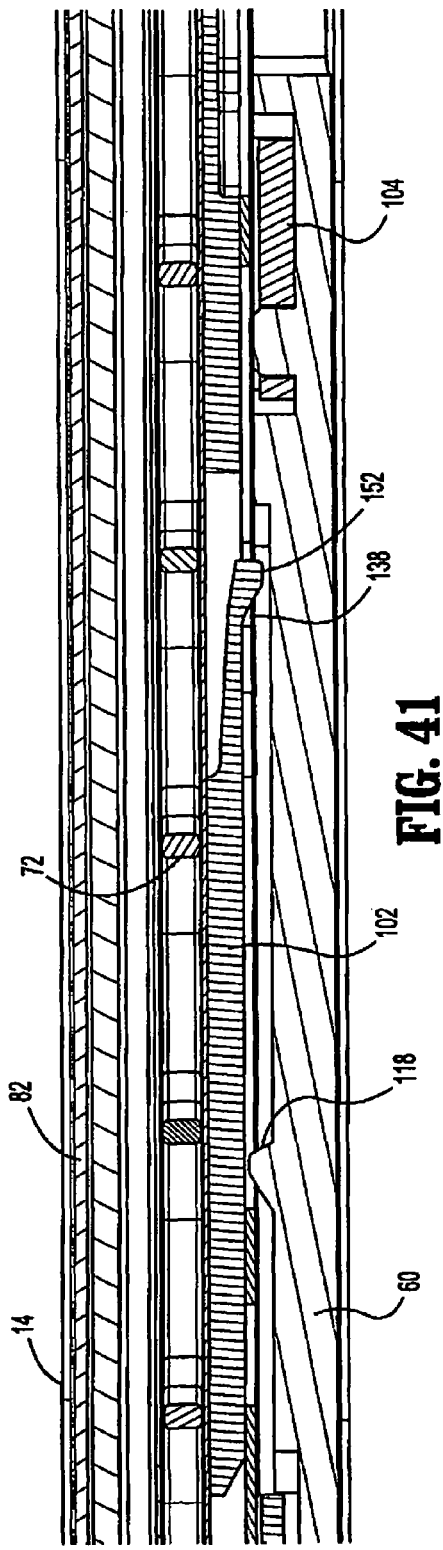
FIG. 41 is enlarged area of detail of FIG. 40.

Referring to FIG. 41, flexible leg 152 of filler component 102 is in the distal window 138 of wedge plate 100. Raised feature 118 on spindle 60 is proximal of flexible leg 152.

Figure 42:
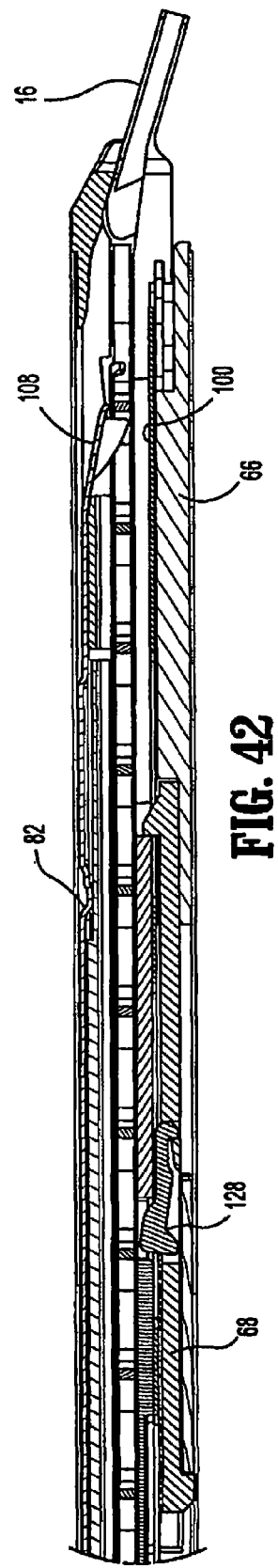
FIG. 42 is a side view, shown in section, of the distal end of the surgical clip applier of FIG. 37.

As best shown in FIG. 42, at the distal end of surgical clip applier 10, when at rest in an unfired state, wedge plate 100 and feed bar 82 are in a proximal-most position relative to jaws 16.

FIGS. 43-47 illustrate the initial at rest position of the wedge plate 100, jaws 16 and filler component 102.

Referring initially to FIGS. 43 and 44, as shown, wedge plate 100 is in a proximal-most position relative to jaws 16. As shown in FIG. 43, flexible leg 152 is in distal window 138 of wedge plate 100, while cam link 104 is in a proximal-most position relative to cam slot 136 in wedge plate 100.

As best shown in FIGS. 45 and 46, wedge plate 100 is in a proximal most position relative to jaws 16 with distal tip 134 proximal of cam edges 178 of jaws 16.

Referring to FIG. 47, wedge plate 100 is in a proximal-most position relative to filler component 102, such that driving edge 166 of wedge plate 100 is proximal of disengaging edge 150 of filler component 102.

Figure 48:
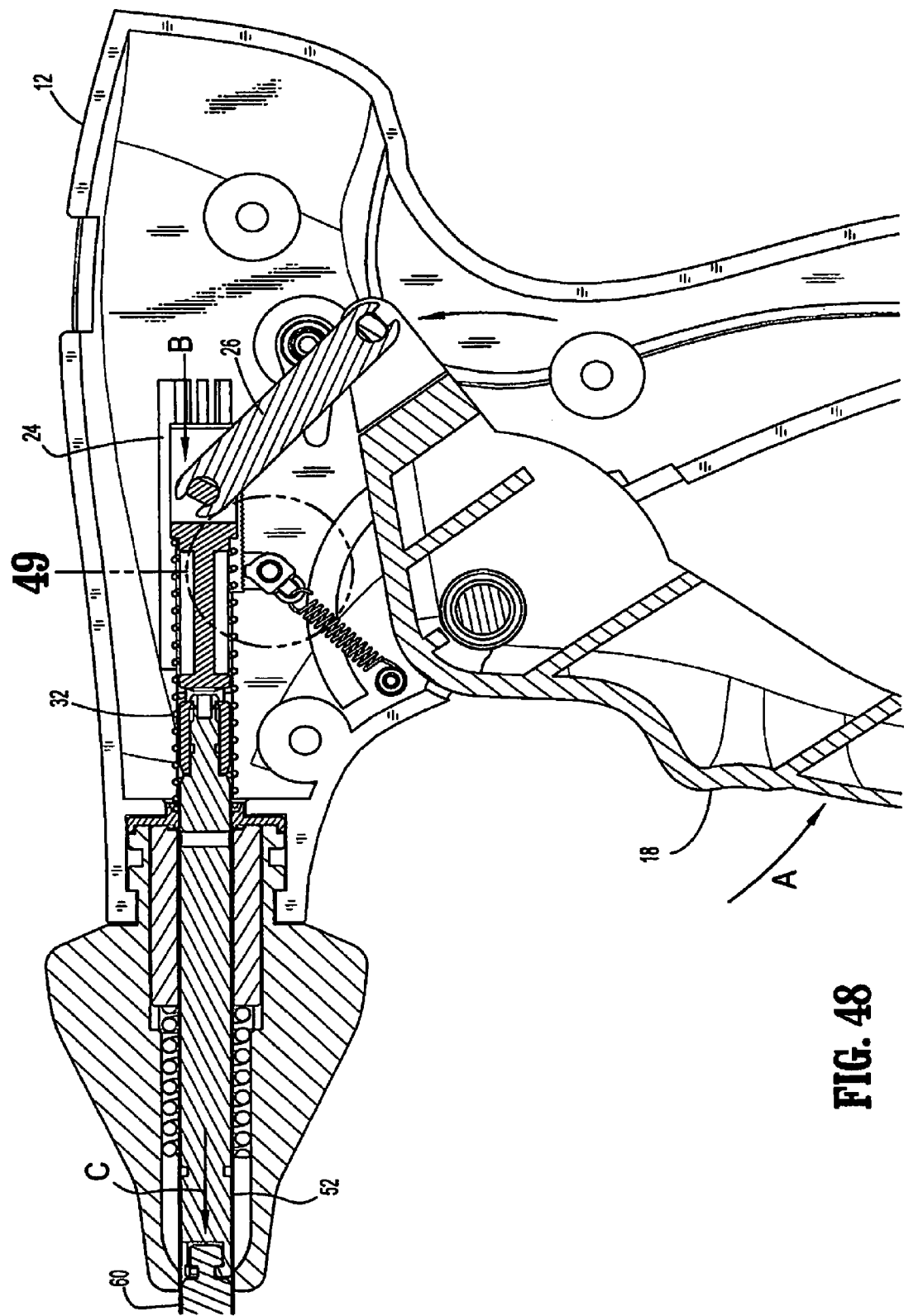
FIG. 48 is a side view, shown in section, of the handle housing at the beginning of an initial stroke.
Figure 49:
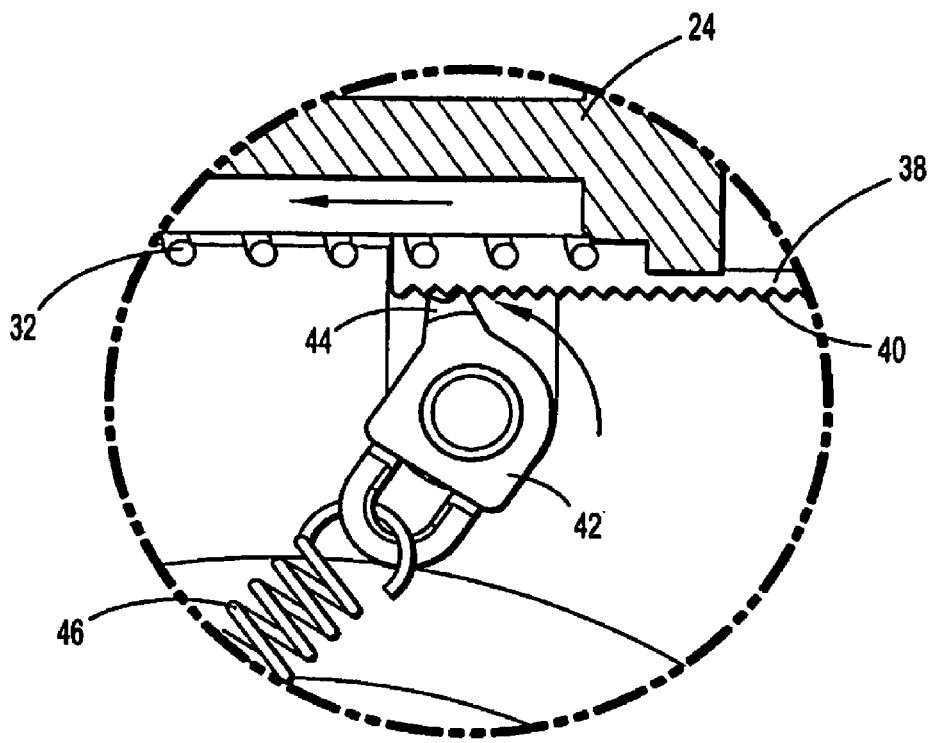
FIG. 49 is an enlarged area of detail of FIG. 48 showing the rack and pawl.
Figure 50:
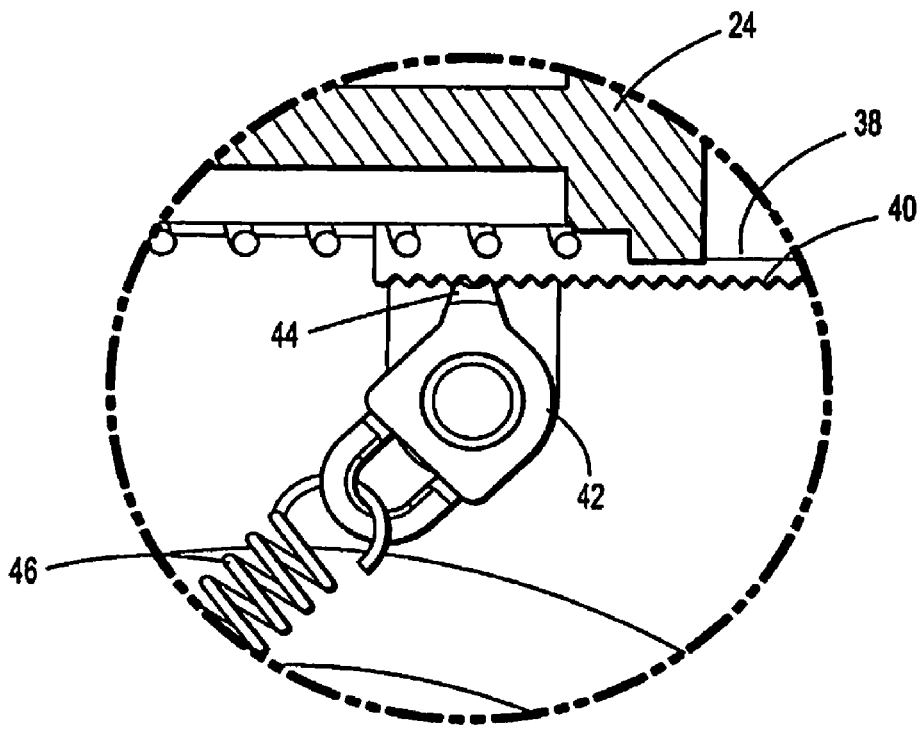
FIG. 50 is an enlarged area of detail of FIG. 48 similar to FIG. 49.

Referring to FIG. 48, to initiate actuation of clip applier 10, trigger 18 is moved through an initial swing as shown by arrow A such that link 26 drives yoke 24 distally as shown by arrow B. As best shown in FIG. 49, as yoke 24 is driven distally in the direction of arrow C, rack teeth 40 on rack 38 slide over pawl teeth 44 on pawl 42. With reference for the moment to FIG. 50, if the trigger 18 is released at this point, rack teeth 40 would restrain pawl teeth 44 against proximal motion, preventing release of trigger 18 and partial or inadvertent partial actuation of surgical clip applier 10.

During the initial stroke, spindle 60 moves a predetermined distance. With regard to FIG. 51, as spindle 60 is driven an initial distal distance, trip lever 96 engages elongated window 106 feed bar 82 and moves feed bar 82 distally a similar distance. As shown in FIGS. 42 & 51, as feed bar 82 is driven distally and a clip 72 is driven into jaws 16, follower 74 moves distally (FIG. 52) due to the bias of spring 76 to urge the stack of surgical clips 72 distally.

Referring to FIGS. 53 and 54, as spindle 60 and feed bar 82 move distally, spindle 60 drives cam link 104 distally an initial distance such that cam link boss 164 on cam link 104 engages wedge plate 100. As shown, flexible leg 152 of filler component 102 is positioned in distal-most window 138 of wedge plate 100.

As shown in FIG. 55, as cam link 104 moves distally with spindle 60, cam link boss 164 engages driving edge 166 on wedge plate 100 to urge wedge plate 100 distally relative to filler component 102.

Referring to FIG. 56, as feed bar 82 moves distally, pusher 108 at the distal end of feed bar 82 engages a clip 72 and begins to urge clip 72 into jaws 16. Notably, at this point, spindle 60 has not yet contacted driver 66, thereby preventing compression of jaws 16 prior to full insertion of surgical clip 72.

Turning again to FIG. 55, as surgical clip applier 10 is actuated through a further second predetermined distance, cam boss 164 on cam link 104 continues to drive wedge plate 100 distally and flexible leg 152 is cammed out of distal window 138 and into proximal window 140 by cam surface 168 to engage wedge plate 100 with filler component 102. As shown in FIGS. 57 & 58, at this point, feed bar 82, wedge plate 100, spindle 60, clips 72 and follower 74 (FIG. 52) are all moving in a distal-most direction.

Figure 59:
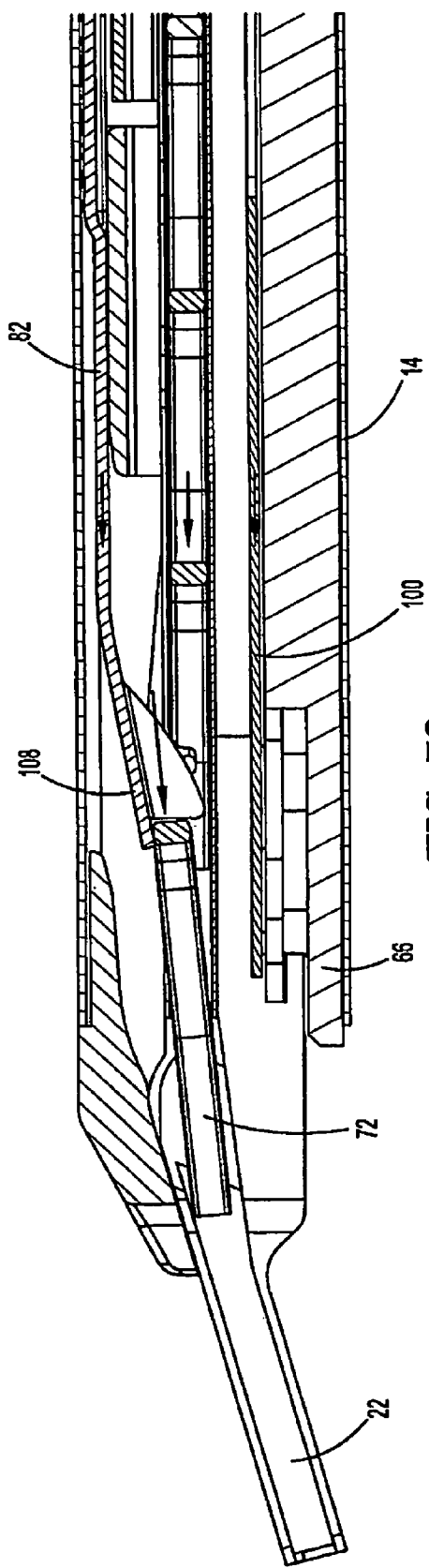
FIG. 59 is a side view, shown in section, illustrating a clip entering the jaws.

Referring to FIG. 59, feed bar 82 continues to urge pusher 108 at the distal end of feed bar 82 against a surgical clip 72 to urge clip 72 into channel 22 in jaws 16. Surgical clips 72 contained in channel 70 are biased in a distal direction by follower 74 (FIG. 52) and wedge plate 100 (FIG. 54) continues to move distally while driver 66 remains stationery relative to elongated tubular member 14.

Figure 60:
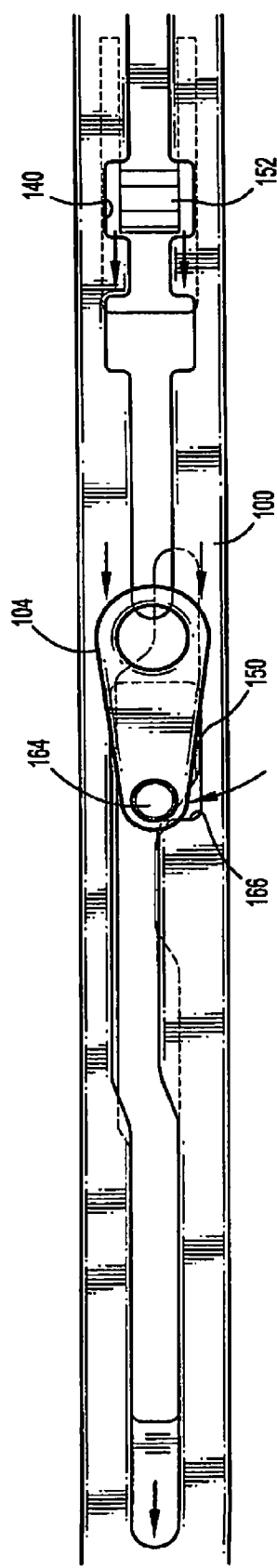
FIG. 60 is a further top view of the cam link and wedge plate movement.

Referring to FIG. 60, as spindle 60 is moved further, cam boss 164 of cam link 104 is cammed out of engagement with driving edge 166 of wedge plate 100 by means of disengaging edge 150 formed in filler component 102 as best shown by the arrows in FIG. 60. During this further stroke of a predetermined distance, flexible leg 152 of filler component 102 snaps into proximal window 140 of wedge plate 100, thereby preventing retraction of wedge plate 100 from its distal-most position.

As shown in FIG. 61, flexible leg 152 is positioned within proximal window 140 of wedge plate 100, thereby restraining wedge plate 100 against retraction, while feed bar 82 and spindle 60 continue to move in a distal direction as shown by the arrows.

As shown in FIGS. 62-63, distal tip 134 of wedge plate 100 urges jaw members 16a and 16b apart by engaging cam surfaces 178 in jaw members 16a and 16b. As noted above, by positioning wedge plate 100 in cam surfaces 178 of jaw members 16a and 16b, wedge plate 100 not only spreads the jaws 16 apart to properly receive surgical slip 72, but additionally restrains each individual jaw member 16a and 16b from flexing with respect to each other, thereby preventing any torque of clip 72 as it is being inserted into jaws 16.

Figure 64:
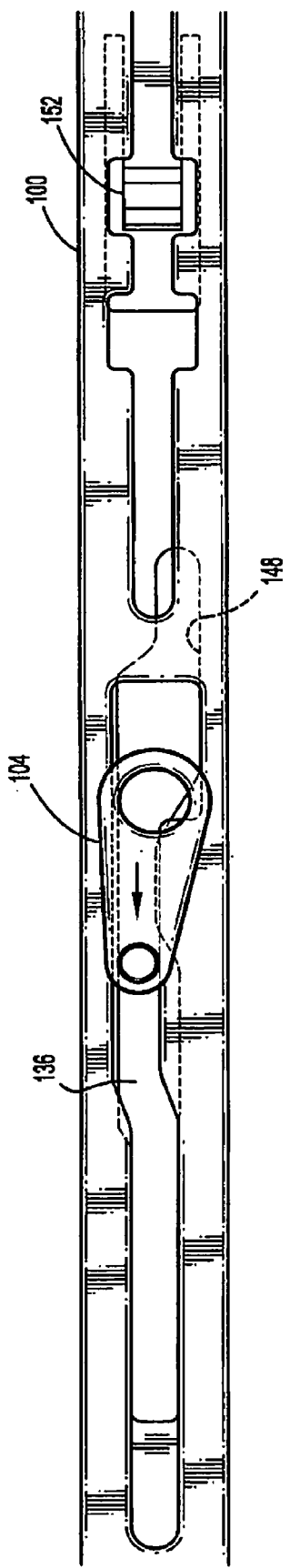
FIG. 64 is a top view illustrating further advancement of the cam link in the wedge plate.

Referring to FIG. 64, as noted above, flexible leg 152 restrains wedge plate 100 from proximal retraction while cam link 104 continues to advance through slots 148 and 136 in filler component 102 (FIG. 64) and wedge plate 100.

Figure 65:
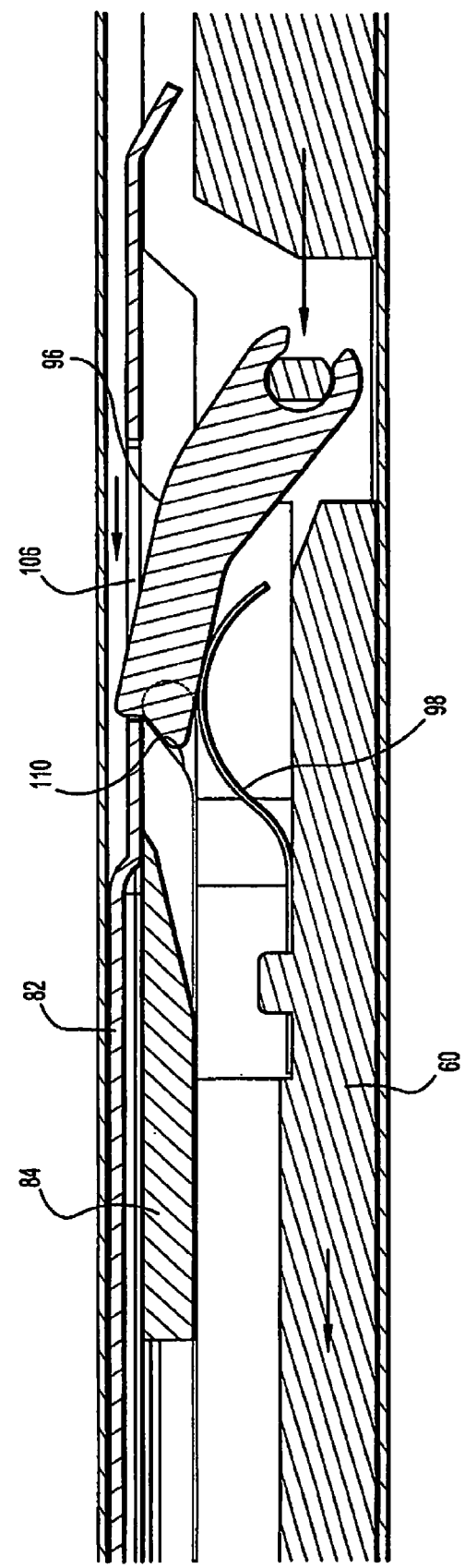
FIG. 65 is a side view, shown in section, illustrating the trip lever engaged with the feed bar.

As best shown in FIG. 65, as spindle 60 continues to move distally through the stroke, trip lever 96 is urged distally with spindle 60 until trip lever 96 engages camming surface 110 (See FIG. 10D) of trip block 84. As camming surface 110 of trip block 84 is urged against trip lever 96, trip lever 96 will be cammed out of engagement with elongated window 106 of feed bar 82 allowing feed bar 82 to return to a proximal position due to the bias of feed bar spring 88 (see FIG. 10).

Figure 66:
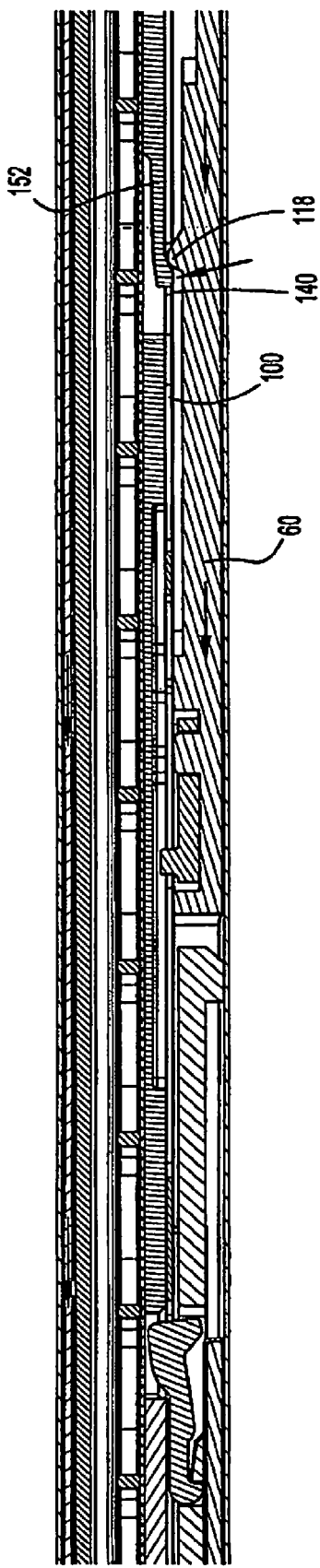
FIG. 66 is a side view, shown in section, illustrating the spindle camming the flexible leg out of engagement with the wedge plate.
Figure 67:
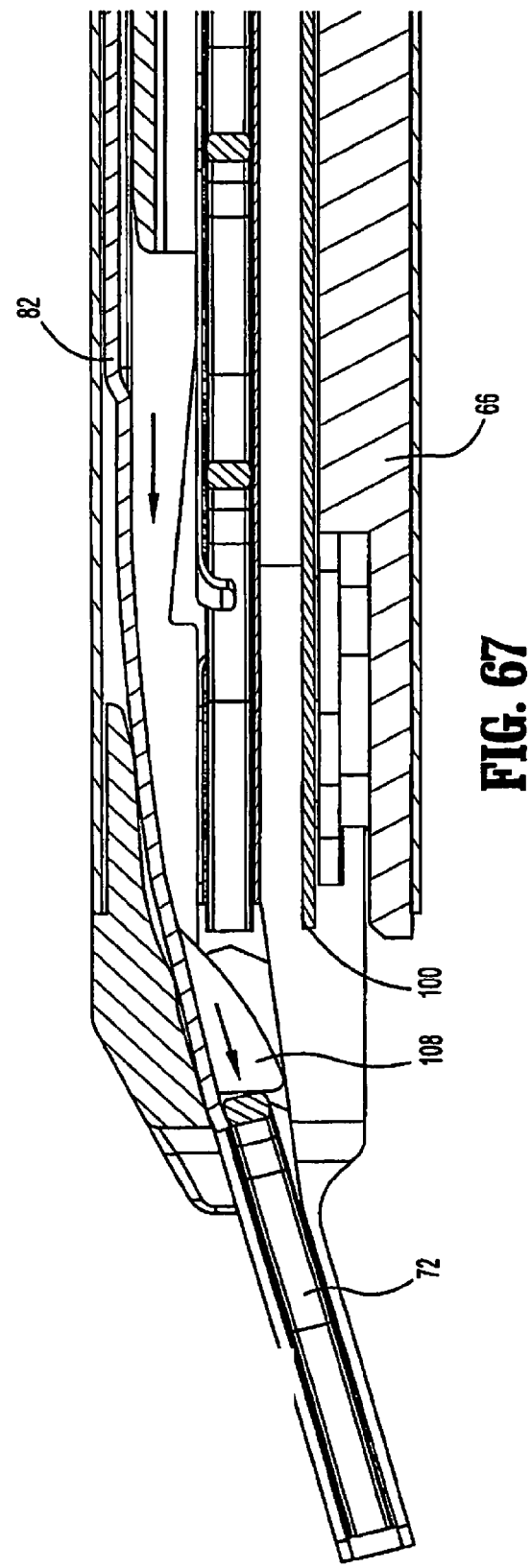
FIG. 67 is a side view, shown in section, illustrating the feed bar loading a clip into the jaw structure.

Referring for the moment to FIG. 66, as spindle 60 continues to move through its stroke, raised feature 118 on spindle 60 begins to cam flexible leg 152 out of proximal window 140 of wedge plate 100, so that the wedge plate 100 will be able to retract prior to, and so that, surgical clip 72 is crimped between jaws 16. This is best illustrated in FIG. 67 where feed bar 82 has fully inserted clip 72 within jaws 16 and wedge plate 100 has retracted to a proximal-most position.

FIG. 68 illustrates trip lever 96 being cammed out of engagement with feed bar 82 by camming surface 110 of trip block 84 and against the bias of biasing spring 98 such that feed bar 82 is disengaged from trip lever 96 and feed bar 82 can start to retract proximally. As shown, in FIG. 69, pusher 108 of feed bar 82 is retracted to a proximal position behind the next distal most clip 72 as wedge plate 100 retracts leaving clip 72 inserted into jaws 16.

Figure 70:
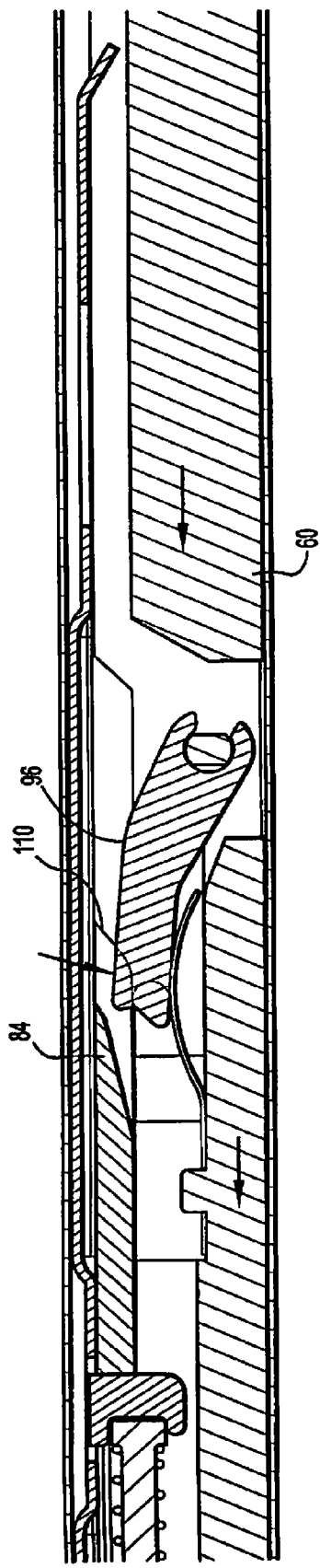
FIG. 70 is a side view, shown in section, illustrating further advancement of the spindle.

Referring to FIG. 70, trip lever 96 is completely cammed down by cam surface 110 on trip block 84 and spindle 60 continues to move distally through a further predetermined stroke.

Figure 71:
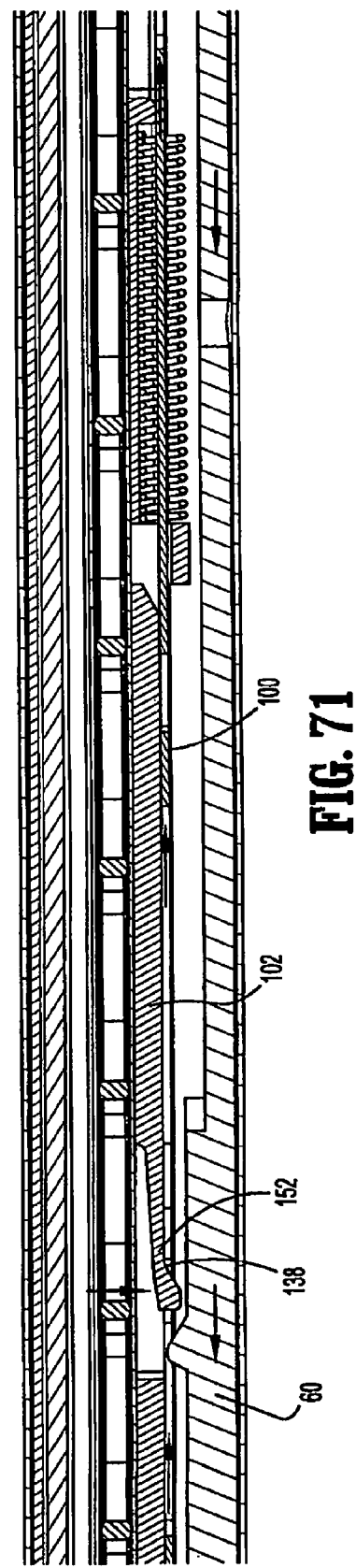
FIG. 71 is a side view, shown in section, illustrating the retraction of the wedge plate and further advancement of the spindle.
Figure 72:
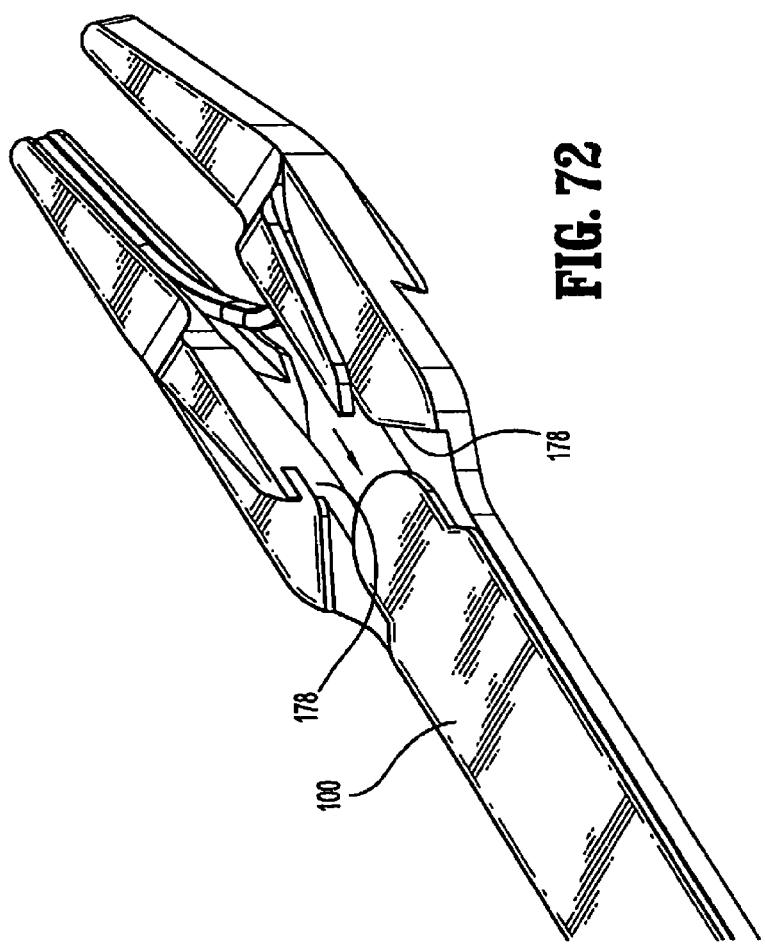
FIG. 72 is a perspective view of the wedge plate retracting from the jaw structure.

Referring for the moment to FIG. 71, as wedge plate 100 retracts proximally while spindle 60 continues to move distally, flexible leg 152 on filler component 102 snaps into distal window 138 of wedge plate 100. As shown in FIG. 72, wedge plate 100 is retracted to a proximal position relative to jaws 16.

Figure 73:
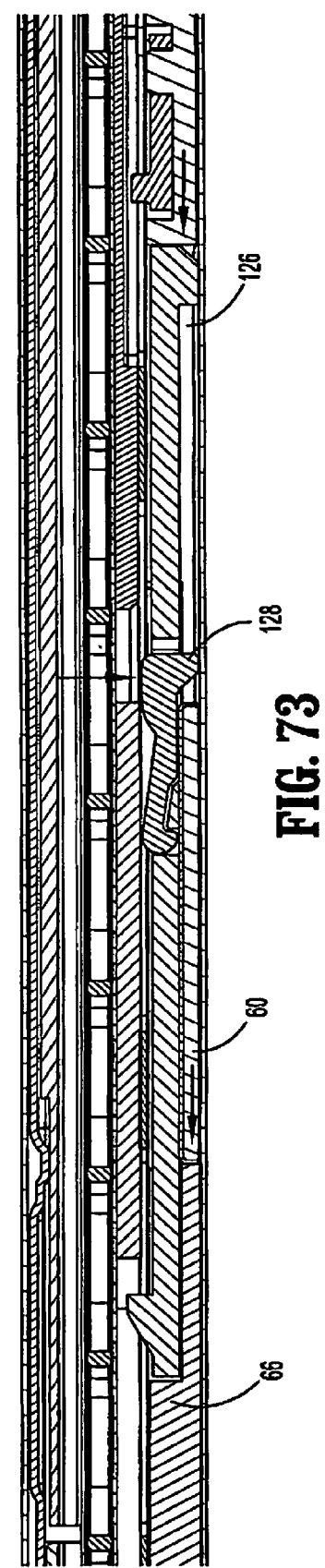
FIG. 73 is a side view, shown in section, with the spindle engaging the driver and a latch retractor engaging the spindle.

Referring to FIG. 73, when latch retractor 128 is cammed downwardly relative to spindle 60, spindle 60 has moved distally to a predetermined distance. The action of spindle 60, now engaging driver 66, pushes driver 66 distally. Driver 66 draws slider joint 68 and simultaneously slider joint 68 drags latch retractor 128 distally mechanically forcing cam surface no. of latch retractor 128 downward to underside of jaw pad 172 and engaging latch retractor 128 with slot 126 of spindle 60.

Figure 74:
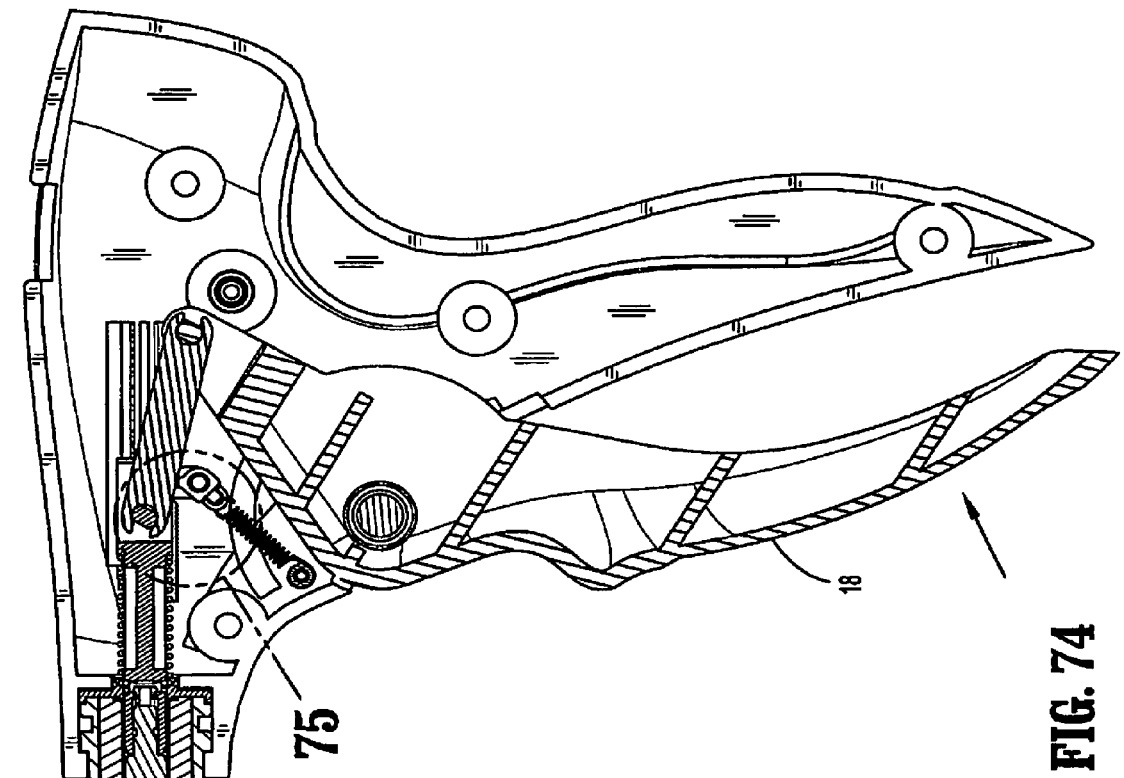
FIG. 74 is a side view of the handle housing with the trigger at full stroke.
Figure 75:
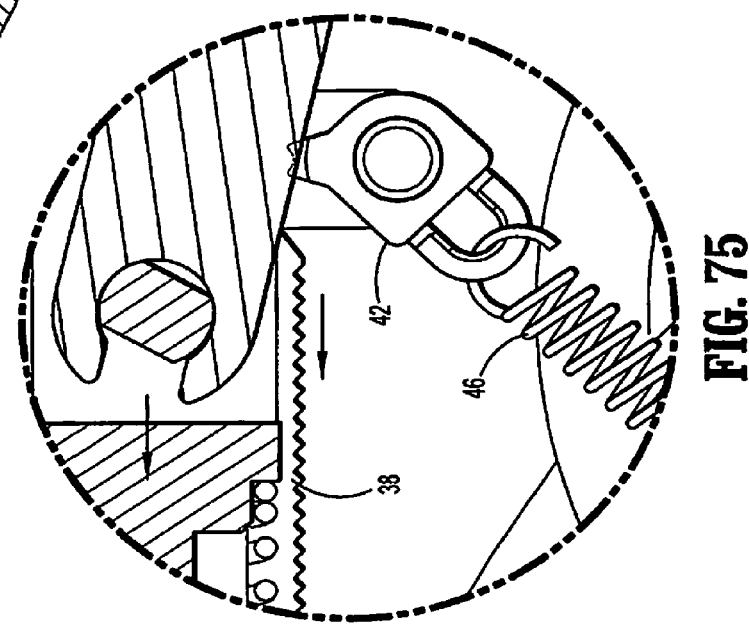
FIG. 75 is an enlarged area of detail of FIG. 74 with the pawl clearing the ratchet rack.

Referring to FIGS. 74-75, as trigger 18 is fully compressed to drive spindle 60 to a distal-most position, rack 38 clears pawl 42 so that the entire drive assembly can retract when the trigger is released. Notably, a full stroke of the spindle 60 is required to take a clip 72 from an initial position to a fully inserted position in the jaws 16. As spindle 60 moves through its distal-most position, it moves driver 66 in the manner described hereinabove to crimp a surgical clip 72. For example, referring to FIGS. 76-79, driver 66 advances distally relative to camming surfaces 160 on jaws 16a and 16b, such that camming surfaces 184 on driver 66 cam jaws 16a and 16b closed thereby closing surgical clip 72 contained therebetween.

Figure 80:
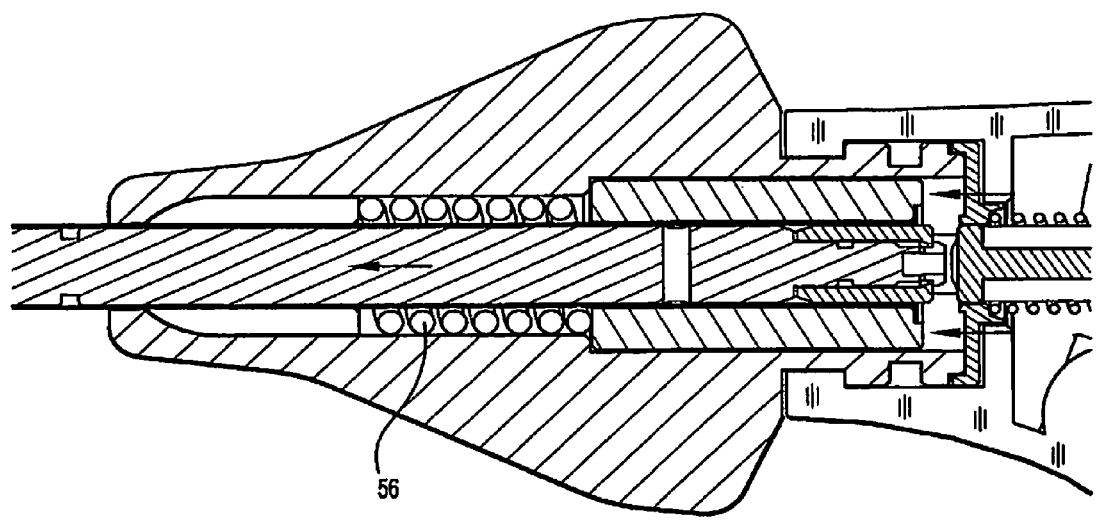
FIG. 80 is a view, shown in section, of the overpressure mechanism including the impact spring.

Referring for the moment to FIG. 80, a security mechanism is provided to prevent an overstroke condition and thereby excessive compression of clip 72 from damaging tissue, jaws 16 or driver 66. If trigger 18 is continued to be squeezed past a stroke required for a full forming of clip 72 impact spring 56 compresses within the space defined between knob 20 and bushing 48 thereby preventing any further distal movement of spindle 60.

Figure 81:
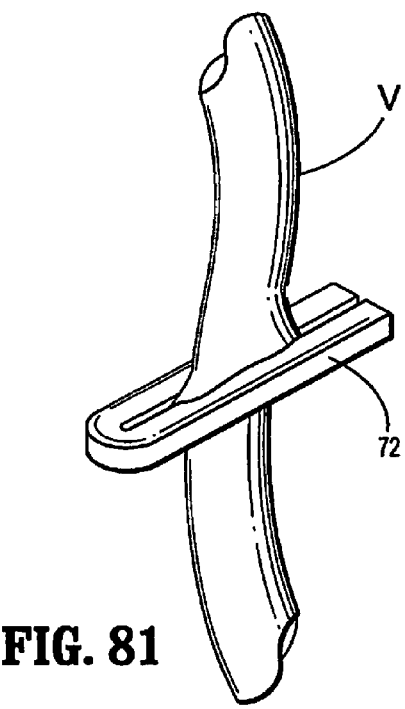
FIG. 81 is a perspective view of a surgical clip formed on a vessel.

A fully formed clip formed about vessel V is illustrated in FIG. 81.

Figure 82:
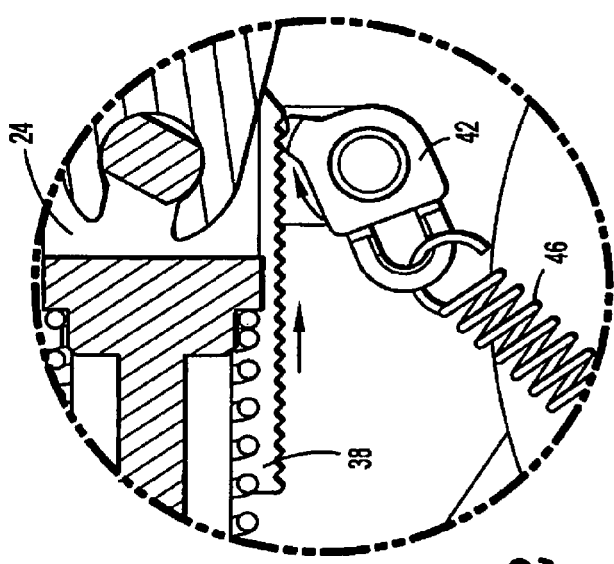
FIG. 82 is an enlarged area of detail of the ratchet mechanism resetting.
Figure 83:
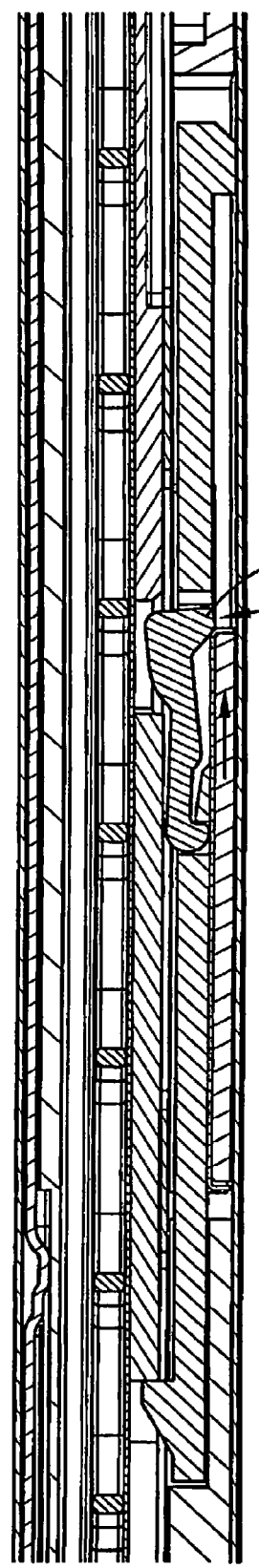
FIG. 83 is a side view, shown in section, illustrating the latch retractor resetting.

Referring to FIG. 82, as trigger 18 is released (not shown), pawl 42 rotates against the bias of pawl spring 46 such that pawl teeth 44 ride along rack teeth 40 to reset the handle assembly. As shown in FIG. 83, when driver 66 retracts, latch retractor 128 is again biased up into its upper-most position, thereby, resetting the drive mechanism.

Referring to FIGS. 84-86, as spindle 60 retracts, raised feature 118 of spindle 60 moves past flexible leg 152 in filler component 102. It should be noted that wedge plate 100 does not move as it has already fully retracted. As spindle 60 retracts, it draws cam link 104 proximally within slots 136 and 148 of wedge plate 100 and filler component 102 to its initial position. As best seen in FIG. 86, in this position, clip applier 10 is again in an initial position to be refired and thus to attach another clip to a vessel.

What is claimed is:

1. An apparatus for application of surgical clips to body tissue, which comprises:
    a) a handle portion;
    b) a body extending distally from the handle portion and defining a longitudinal axis a member disposed inside said body;
    c) at least one surgical clip disposed within the body;
    d) a jaw assembly mounted adjacent a distal end portion of the body, the jaw assembly including first and second jaw portions movable between a spaced-apart and an approximated position;
    e) a wedge plate having a distalmost end longitudinally movable between the first and second jaw portions, said wedge plate has a first proximal window and a second proximal window, the first proximal window being adapted to be engaged by said member disposed in said body, said member being configured to hold said distalmost end of said wedge plate in a distal most position being between said first and second jaw members; the second proximal window being adapted to be engaged by said member to hold said distalmost end of said wedge plate in a proximal most position being retracted from between said first and second jaw members, wherein when said distalmost end of said wedge plate is in said proximal most position the first and second jaw members are free to be moved to the approximated position to compress said clip; and
    f) an actuator at least partially disposed within the body and longitudinally movable in response to actuation of the handle portion to move the first and second jaw portions to the approximated position when said distalmost end of wedge plate is in said proximal most position.

2. The apparatus of claim 1, wherein said distalmost end of said wedge plate biases the first and second jaw portions when said wedge plate is longitudinally moved between the first and second jaw portions and maintains said first and second jaw portions in a fixed predetermined relationship during loading of said clip, said fixed predetermined relationship preventing flexing of the first and second jaw members during clip loading.

3. The apparatus of claim 1, wherein said distalmost end of said wedge plate has a rounded distal tip.

4. The apparatus of claim 1, wherein said first proximal window is connected to said second proximal window by a longitudinal slot.

5. The apparatus of claim 1, wherein said member is moved from said second proximal window to said first proximal window when said wedge plate is moved distally.

6. The apparatus of claim 1, wherein said member is a flexible leg.

7. An apparatus for application of surgical clips to body tissue, which comprises:
    a) a handle portion;
    b) a body extending distally from the handle portion and defining a longitudinal axis;
    c) at least one surgical clip disposed within the body;
    d) a jaw assembly mounted adjacent a distal end portion of the body, the jaw assembly including first and second jaw portions movable between a spaced-apart and an approximated position;
    e) a wedge plate being longitudinally movable with respect to the body, the wedge plate defining a cam slot therethrough, wherein said cam slot of the wedge plate has a proximal side and a distal side, wherein said wedge plate further comprises a biasing device;
    f) an actuator at least partially disposed within the body and longitudinally movable in response to actuation of the handle portion to move the first and second jaw portions to the approximated position, the actuator having a cam link mounted thereto and being engageable with a driving edge of the cam slot in the wedge plate to provide proximal movement of the wedge plate in response to proximal movement of the actuator, and wherein at said distal side of side cam slot, said cam link traverses past said driving edge of said cam slot at a line of demarcation, wherein said cam link terminates distal movement of said wedge plate at said demarcation line, and wherein at said line of demarcation said cam link disengages from said driving edge to permit said biasing device to retract said wedge plate; and g) a filler component at least partially disposed within the body along the wedge plate, the filler component defining a cam slot, the cam link being engageable with a disengaging edge of the cam slot in the filler component to allow distal movement of the wedge plate.

8. The apparatus of claim 7, wherein said wedge plate is selectively advanceable between said first and second jaw members to maintain said first and second jaw members separated.

9. The apparatus of claim 7, wherein said cam link disengages said wedge plate at said demarcation line, and wherein the disengagement of said cam link permits retraction of a distal end of the wedge plate from between said first and second jaw members.

\* \* \* \* \*